US012767726B2

(12) United States Patent
Miyake et al.

(10) Patent No.: US 12,767,726 B2
(45) **Date of Patent: *Oct. 20, 2026**

(54) ANTI-HUMAN TLR7 ANTIBODY

(71) Applicants: Daiichi Sankyo Company, Limited, Tokyo (JP); The University of Tokyo, Tokyo (JP)

(72) Inventors: Kensuke Miyake, Tokyo (JP); Yusuke Murakami, Tokyo (JP); Yuji Motoi, Tokyo (JP); Atsuo Kanno, Tokyo (JP); Toshiyuki Shimizu, Tokyo (JP); Umeharu Ohto, Tokyo (JP); Takaichi Shimozato, Tokyo (JP); Atsushi Manno, Tokyo (JP); Takashi Kagari, Tokyo (JP); Jun Ishiguro, Tokyo (JP); Kensuke Nakamura, Tokyo (JP); Takashi Isobe, Tokyo (JP)

(73) Assignees: Daiichi Sankyo Company, Limited, Tokyo (JP); The University of Tokyo, Tokyo (JP)

( * ) Notice: Subject to any disclaimer, the term of this patent is extended or adjusted under 35 U.S.C. 154(b) by 814 days.

This patent is subject to a terminal disclaimer.

(21) Appl. No.: 18/146,817

(22) Filed: Dec. 27, 2022

(65) Prior Publication Data

US 2023/0212306 A1 Jul. 6, 2023

Related U.S. Application Data

(63) Continuation of application No. 17/366,820, filed on Jul. 2, 2021, now Pat. No. 11,578,138, which is a continuation of application No. 17/069,760, filed on Oct. 13, 2020, now Pat. No. 11,091,560, which is a continuation-in-part of application No. PCT/JP2019/021466, filed on May 30, 2019.

(30) Foreign Application Priority Data

May 31, 2018 (JP) ................................ 2018-104676

(51) Int. Cl.

| | |
|---|---|
| ***C07K 16/28*** | (2006.01) |
| ***A61K 39/395*** | (2006.01) |
| ***A61K 45/06*** | (2006.01) |
| *A61K 39/00* | (2006.01) |

(52) U.S. Cl.

CPC ...... *C07K 16/2896* (2013.01); *A61K 39/3955* (2013.01); *A61K 45/06* (2013.01); *A61K 2039/505* (2013.01); *C07K 2317/24* (2013.01); *C07K 2317/52* (2013.01); *C07K 2317/565* (2013.01); *C07K 2317/76* (2013.01)

(58) Field of Classification Search

CPC ............ C07K 16/2896; C07K 2317/24; C07K 2317/52; C07K 2317/565; C07K 2317/76; C07K 16/28; C07K 16/46; A61K 39/3955; A61K 45/06; A61K 2039/505; A61K 39/39541; A61K 39/395; A61P 29/00; A61P 31/00; A61P 35/00; A61P 37/00; A61P 19/00; A61P 19/02; A61P 21/00; C12N 5/10; C12N 15/63

See application file for complete search history.

(56) References Cited

U.S. PATENT DOCUMENTS

| | | | | |
|---|---|---|---|---|
| 10,370,451 | B2 * | 8/2019 | Miyake .................. | A61P 37/06 |
| 11,091,560 | B2 | 8/2021 | Miyake et al. | |
| 11,578,138 | B2 * | 2/2023 | Miyake .............. | C07K 16/2896 |
| 2003/0032090 | A1 | 2/2003 | Hardiman et al. | |
| 2016/0185871 | A1 | 6/2016 | Miyake et al. | |
| 2016/0361360 | A1 * | 12/2016 | Chang .................... | A61P 17/06 |
| 2018/0025818 | A1 | 1/2018 | Yamamichi et al. | |
| 2018/0258184 | A1 | 9/2018 | Satoh et al. | |

FOREIGN PATENT DOCUMENTS

| | | | |
|---|---|---|---|
| EP | 2409991 | A1 | 1/2012 |
| EP | 2990419 | | 3/2016 |
| JP | 2003533996 | | 11/2003 |
| TW | 201718643 | A | 6/2017 |
| WO | 03080672 | | 10/2003 |
| WO | 2010054288 | | 5/2010 |
| WO | 2014174704 | | 10/2014 |
| WO | 2016201300 | | 12/2016 |
| WO | 2016210108 | | 12/2016 |
| WO | 2017004144 | | 1/2017 |

OTHER PUBLICATIONS

Janeway, C. A. Jr. et al., Immunobiology: The Immune System in Health and Disease. Chapter 3: Structure of the Antibody Molecule and Immunoglobulin Genes. 3rd Edition, 1997 Garland Publishing Inc., pp. 3:1-3:11 (Year: 1997).*

Edwards, B. M. et al. The Remarkable Flexibility of the Human Antibody Repertoire; Isolation of Over One Thousand Different Antibodies to a Single Protein, BLyS. J Mol Biol 2003; 334:103-118. (Year: 2003).*

Brown et al. "TLR7 gain-of-function genetic variation causes human lupus." 2022. Nature. 605, 349-356. (Year: 2022).*

Kuhn et al. "The Diagnosis and Treatment of Systemic Lupus Erythematosus." Dtsch Arztebl Int. 112: 423â32. (Year: 2015).*

Perez De La Lastra, J.M. et al., "Epitope mapping of 10 monoclonal antibodies against the pig analogue of human membrane cofactor protein (MCP)," Immunology 1999, vol. 96, No. 4, pp. 663-670.

(Continued)

*Primary Examiner* — Misook Yu
*Assistant Examiner* — Grace H Lunde
(74) *Attorney, Agent, or Firm* — Christensen O'Connor Johnson Kindness PLLC

(57) ABSTRACT

The present invention provides a pharmaceutical composition comprising an antibody which binds specifically to human TLR7 or monkey TLR7 and does not bind to mouse TLR7 or rat TLR7, and has an activity of inhibiting a function of human TLR7 or monkey TLR7, and the like.

18 Claims, 26 Drawing Sheets

Specification includes a Sequence Listing.

(56) References Cited

OTHER PUBLICATIONS

Office Action mailed Oct. 28, 2024, issued in corresponding European Application No. EP 19811934.9, filed May 30, 2019, 12 pages.
Christensen, S.R., et al., "Toll-Like Receptor 7 and TLR9 Dictate Autoantibody Specificity and Have Opposing Inflammatory and Regulatory Roles in a Murine Model of Lupus," Immunity 25:417-428, Sep. 2006.
Chuang, T-H. and R.J. Ulevitch, "Cloning and Characterization of a Sub-Family of Human Toll-Like Receptors: hTLR7, hTLR8 and hTLR9," European Cytokine Network 11(3):372-378, Sep. 2000.
International Search Report mailed Aug. 27, 2019, issued in corresponding Application No. PCT/JP2019/021466, filed May 30, 2019, 3 pages.
Kanno, A., et al., "Essential Role for Toll-Like Receptor 7 (TLR7)-Unique Cysteines in an Intramolecular Disulfide Bond, Proteolytic Cleavage and RNA Sensing," International Immunology 25 (7):413-422, 2013.
Lyn-Cook, B.D., et al., "Increased Expression of Toll-Like Receptors (TLRs) 7 and 9 and Other Cytokines in Systemic Lupus Erythematosus (SLE) Patients: Ethnic Differences and Potential New Targets for Therapeutic Drugs," Molecular Immunology 61:38-43, 2014.
Takeuchi, O., and S. Akira, "Pattern Recognition Receptors and Inflammation," Cell 140:805-820, Mar. 2010.
Rudikoff Stuart, et al., "Single amino acid substitution altering antigen-binding specificity," Proc. Natl. Acad. Sci. USA, Mar. 1982, vol. 79, pp. 1979-1983.
Kussie, Paul H. et al., "A Single Engineered Amino Acid Substitution Changes Antibody Fine Specificity," Journal of Immunology, 1994, vol. 152, pp. 146-152.
Chen, Ching, et al., "Enhancement and destruction of antibody function by somatic mutation: unequal occurrence is controlled by V gene combinatorial associations," The EMBO Journal, 1995, vol. 14, No. 12, pp. 2784-2794.
D'Angelo, Sara, et al., "Many Many Routes to an Antibody Heavy-Chain CDR3: Necessary, Yet Insufficient, for Specific Binding," Frontiers in Immunology, Mar. 2018, vol. 9, Article 395, pp. 1-13.
Piche-Nicholas, Nicole M. et al., Changes in complementarity-determining regions significantly after IgG binding to the neonatal Fc receptor (FcRn) and pharmacokinetics, MABS, 2018, vol. 10, No. 1, pp. 81-94.
Hennessy, Elizabeth J. et al., "Targeting Toll-like Receptors: Emerging Therapeutics?," Nature Reviews / Drug Discovery, Apr. 2010, vol. 9, pp. 293-307.
Tamura, M., et al., "Structural Correlates of An Anticarcinoma Antibody: Identification of Specificity-Determining Residues (SDRs) and Development of a Minimally Immunogenic Antibody Variant by Retention of SDRs Only," The Journal of Immunology 164:1432-1441, Feb. 2000.
Office Action mailed Dec. 9, 2021, issued in corresponding Canadian Application No. 3,099,900, filed Nov. 10, 2020, 7 pages.
Written Opinion mailed Aug. 27, 2019, issued in corresponding International Patent Application No. PCT/JP2019/021466, filed May 30, 2019, 12 pages.
Extended European Search Report mailed Feb. 18, 2022, issued in corresponding European Patent Application No. 19811934.9, filed May 30, 2019, 13 pages.
N.N.: "Human TLR7 Antibody: Monoclonal Mouse IgG2A Clone #533707," R&D Systems Product Catalogue No. MAB5875. Oct. 13, 2015 <https://resources.rndsystems.com/pdfs/datasheets/mab5875.pdf> [Retrieved Nov. 30, 2016], whole document.
N.N.:"Idera Pharmaceuticals Announces Positive Top-Line Results From Phase 2 Trial of IMO-3100 in Patients With Moderate-to-Severe Plaque Psoriasis," Idera Press Release. Dec. 19, 2012, <http://ir.iderapharma.com/phoenix.zhtml?c=208904&p=irol-newsArticle_print&ID=1768483> [Retrieved Dec. 1, 2016], whole document.
Wu, Y-W., et al., "Toll-Like Receptors: Potential Targets for Lupus Treatment," Acta Pharmacologica Sinica 36(12):1395-1407, Dec. 1, 2015.
Search Report and Written Opinion mailed May 19, 2022, issued in corresponding Singaporean Application No. 11202010939W, filed May 30, 2019, 8 pages.
"Anti-TLR7 Antibody (4F4): sc-57463," Santa Cruz Biotechnology Inc., 2015, <https://www.scbt.com/p/tlr7-antibody-4f4>, 11 pages.
"Recombinant Anti-TLR7 antibody [EPR2088(2)] (ab124928)," Abcam plc., 2015, <https://www.abcam.com/tlr7-antibody-epr20882-ab124928.html>, 4 pages.
Filippovich Yu.B.et al., Biochemical foundations of human life, M. Vlados, 2005, p. 49-50, 70.
Yarilin A. A, Fundamentals of Immunology, M. Medicine, 1999, p. 172-173.
Data base GenBank acc. No. BC033651.1, "*Homo sapiens* toll-like receptor 7, mRNA (cDNA clone MGC:45096 Image:5582912), complete cds," Jul. 15, 2006, 3 pages.
Liu, Hongcheng, et al. "In vitro and in vivo modifications of recombinant and human IgG antibodies." MAbs. Vol. 6., No. 5. Taylor & Francis, 2014, pp. 1145-1154.
Office Action mailed Apr. 22, 2022, issued in corresponding Russian Application No. RU2020140526, filed May 30, 2019, 27 pages.
Colman, P.M., "Effects of amino acid sequence changes on antibody-antigen interactions," Research in Immunology, 1994, vol. 145, pp. 33-36.
Office Action mailed May 30, 2023, issued in corresponding Taiwanese Application No. 108118694, filed May 30, 2019, 18 pages.
Office Action mailed Mar. 10, 2023, issued in corresponding Japanese Application No. 2020-182120, filed Oct. 30, 2020, 11 pages.
Mitterreiter, J.G. et al., "Satellite glial cells in human trigeminal ganglia have a broad expression of functional Toll-like receptors," European Journal of Immunology, Allergy and Inflammation, 47:1181-1187, 2017.
Kanno, et al., "Targeting cell surface TLR7 for therapeutic intervention in autoimmune diseases," Nature Communications, 2015, vol. 6, No. 6119, pp. 1-12.
Office Action mailed Sep. 18, 2025, issued in corresponding Indian Application No. 202017050437 filed Nov. 19, 2020, 7 pages.

* cited by examiner

Figure 1

Amino acid sequence (SEQ ID NO: 2) of human TLR7 (variant 1)

mvfpmwtlkrqililfniiliskllgarwfpktlpcdvtldvpknhvivdctdkhlt
eipggiptnttnltltinhipdispasfhrldhlveidfrcncvpiplgsknnmcik
rlqikprsfsgltylkslyldgnqlleipqglppslqllsleannifsirkenltel
anieilylgqncyyrnpcyvsysiekdaflnltklkvlslkdnnvtavptvlpstlt
elylynnmiakiqeddfnnlnqlqildlsgncprcynapfpcapcknnsplqipvna
fdaltelkvlrlhsnslqhvpprwfkninklqeldlsqnflakeigdakflhflpsl
iqldlsfnfelqvyrasmnlsqafsslkslkilrirgyvfkelksfnlsplhnlqnl
evldlgtnfikianlsmfkqfkrlkvidlsvnkispsgdssevgfcsnartsvesye
pqvleqlhyfrydkyarscrfknkeasfmsvnescykygqtldlsknsiffvkssdf
qhlsflkclnlsgnlisqtlngsefqplaelryldfsnnrldllhstafeelhklev
ldissnshyfqsegithmlnftknlkvlqklmmndndissstsrtmeseslrtlefr
gnhldvlwregdnrylqlfknllkleeldisknslsflpsgvfdgmppnlknlslak
nglksfswkklqclknletldlshnqlttvperlsncsrslknlilknnqirsltky
flqdafqlryldlssnkiqmiqktsfpenvlnnlkmlllhhnrflctcdavwfvwwv
nhtevtipylatdvtcvgpgahkgqsvisldlytceldltnlilfslsisvslflmv
mmtashlyfwdvwyiyhfckakikgyqrlispdccydafivydtkdpavtewvlael
vakledprekhfnlcleerdwlpgqpvlenlsqsiqlskktvfvmtdkyaktenfki
afylshqrlmdekvdviiliflekpfqkskflqlrkrlcgssvlewptnpqahpyfw
qclknalatdnhvaysqvfketv

Figure 2

Amino acid sequence (SEQ ID NO: 4) of human TLR7 (variant 2)

mvfpmwtlkrqililfniiliskllgarwfpktlpcdvtldvpknhvivdctdkhlt
eipggiptnttnltltinhipdispasfhrldhlveidfrcncvpiplgsknnmcik
rlqikprsfsgltylkslyldgnqlleipqglppslqllsleannifsirkenltel
anieilylgqncyyrnpcyvsysiekdaflnltklkvlslkdnnvtavptvlpstlt
elylynnmiakiqeddfnnlnqlqildlsgncprcynapfpcapcknnsplqipvna
fdaltelkvlrlhsnslqhvpprwfkninklqeldlsqnflakeigdakflhflpsl
iqldlsfnfelqvyrasmnlsqafsslkslkilrirgyvfkelksfnlsplhnlqnl
evldlgtnfikianlsmfkqfkrlkvidlsvnkispsgdssevgfcsnartsvesye
pqvleqlhyfrydkyarscrfknkeasfmsvnescykygqtldlsknsiffvkssdf
qhlsflkclnlsgnlisqtlngsefqplaelryldfsnnrldllhstafeelhklev
ldissnshyfqsegithmlnftknlkvlqklmmndndissstsrtmeseslrtlefr
gnhldvlwregdnrylqlfknllkleeldisknslsflpsgvfdgmppnlknlslak
nglksfswkklqclknletldlshnqlttvperlsncsrshknlilknnqirsptky
flqdafqlryldlssnkiqmiqktsfpenvlnnlkmlllhhnrflctcdavwfvwwv
nhtevtipylatdvtcvgpgahkgqsvisldlytceldltnlilfslsisvslflmv
mmtashlyfwdvwyiyhfckakikgyqrlispdccydafivydtkdpavtewvlael
vakledprekhfnlcleerdwlpgqpvlenlsqsiqlskktvfvmtdkyaktenfki
afylshqrlmdekvdviiliflekpfqkskflqlrkrlcgssvlewptnpqahpyfw
qclknalatdnhvaysqvfketv

Figure 3

Amino acid sequence (SEQ ID NO: 83) of mouse TLR7 mvfsmwtrkrqiliflnmllvsrvfgfrwfpktlpcevkvnipeahvivdctdkhlt
eipegiptnttnltltinhipsispdsfrrlnhleeidlrcncvpvllgskanvctk
rlqirpgsfsglsdlkalyldgnqlleipqdlpsslhllsleannifsitkenltel
vnietlylgqncyyrnpcnvsysiekdaflvmrnlkvlslkdnnvtavpttlppnll
elylynniikkiqendfnnlnelqvldlsgncprcynvpypctpcennsplqihdna
fnsltelkvlrlhsnslqhvpptwfknmrnlqeldlsqnylareieeakflhflpnl
veldfsfnyelqvyhasitlphslsslenlkilrvkgyvfkelknsslsvlhklprl
evldlgtnfikiadlnifkhfenlklidlsvnkispseesrevgfcpnaqtsvdrhg
pqvlealhyfrydeyarscrfknkeppsflplnadchiygqtldlsrnniffikpsd
fqhlsflkclnlsgntiggtlngselwplrelryldfsnnrldllystafeelqsle
vldlssnshyfqaegithmlnftkklrlldklmmndndistsasrtmesdslrilef
rgnhldvlwragdnryldffknlfnlevldisrnslnslppevfegmppnlknlsla
knglksffwdrlqllkhleildlshnqltkvperlancskslttlilkhnqirqltk
yfledalqlryldissnkiqviqktsfpenvlnnlemlvlhhnrflcncdavwfvww
vnhtdvtipylatdvtcvgpgahkgqsvisldlytceldltnlilfsvsissvlflm
vvmttshlffwdmwyiyyfwkakikgyqhlqsmescydafivydtknsavtewvlqe
lvakledprekhfnlcleerdwlpgqpvlenlsqsiqlskktvfvmtqkyaktesfk
mafylshqrlldekvdviiliflekplqkskflqlrkrlcrssvlewpanpqahpyf
wqclknalttdnhvaysqmfketv

Figure 4

Amino acid sequence (SEQ ID NO: 84) of rat TLR7 mvfpmwtlkrqsfiflnmilvsrvlgfrwypktlpcdvsldstnthvivdctdkhlt
eipegiptnttnltltinhipsispdsfhrlkhleeldlrcncvpillgskanvctk
rlqirpgsfsglsdlkslyldgnqlleipqdlpsslqllsleannifsitkenlsel
vnieslylgqncyyrnpcnvsysiekdaflvmknlkvlslkdnnvtavptilppnll
elylynniikriqehdfnklsqlqvldlsgncprcynvpypctpcennsplqihdna
fdsltelkvlrlhsnslqhvpaewfknmsnlqeldlsqnylareieeakflnslpnl
vqldlsfnyelqvyhasitlphslssltklknlyikgyvfkelkdsslsvlhnlsnl
evldlgtnfikiadlnifqqfenlkfidlsvnkispseesrevglcpnaqtsvdwhg
pqvlealhyfrydeyarscrfknkepptflplnadchtygktldlsrnniffikpsd
fkhlsflkclnlsgnaiggtlngselqplrelryldfsnnrldllystafeelqnle
ildlssnshyfqaegithmlnftkklrhleklmmndndistsasrtmeseslrvlef
rgnhldvlwrdgdnryldffknllnleeldisrnslnsvppgvfegmppnlttlsla
knglrsfswgrlqllkhlknldlshnqlttvparlancsksltklilnhnqirqltk
yfledalqlryldissnkiqviqktsfpenvlnnlnmlllhhnrflcncdavwfvww
vnhtdvtipylatdvtcagpgahkgqsvisldlytceldltnlilfsvsissvlflm
ivmttshlffwdmwyiyyfwkakikgyqhlqsmescydafivydtknsavtewvlqe
lvvkledprekhfnlcleerdwlpgqpvlenlsqsiqlsrktvfvmtqkyaktesfk
mafylshqrlmdekvdviiliflekplqkskflqlrkrlcsssvlewptnpqahpyf
wqclknalttdnhvaysqmfketv

Figure 5

Amino acid sequence (SEQ ID NO: 85) of monkey TLR7 mmfpvwtlkrqililfniiliskllgarwfpktlpcdvtldvsknhvivdctdkhlt eipggiptnttnltltinhipdispasfhrlvhlveidfrcncvpirlgsksnmcpr rlqikprsfsgltylkslyldgnqlleipqglppslqllsleannifsirkenltel anieilylgqncyyrnpcyvsysiekdaflnltklkvlslkdnnvttvptvlpstlt elylynnmiaeiqeddfnnlnqlqildlsgncprcynapfpctpcknnsplqipvna fdaltelkvlrlhsnslqhvpprwfkninnlqeldlsqnflakeigdakflhflpnl iqldlsfnfelqvyrasmnlsqafsslkslkilrirgyvfkelksfnlsplhnlqnl evldlgtnfikianlsmfkqfkrlkvidlsvnkispsgdssevgfcsnartsvesye pqvleqlyyfrydkyarscrfknkeasftsvnescykygqtldlsknsiffikssdf qhlsflkclnlsgnlisqtlngsefqplaelryldfsnnrldllhstafeelrklev ldissnshyfqsegithmlnftknlkvlqklmmndndissstsrtmeseslrtlefr gnhldvlwrdgdnrylqlfknllkleeldisknslsflpsgvfdgmppnlknlslak nglksfiweklrylknletldlshnqlttvperlsncsrslknlilknnqirsltky flqdafqlryldlssnkiqmiqktsfpenvlnnlkmlllhhnrflctcdavwfvwwv nhtevtipylatdvtcvgpgahkgqsvisldlytceldltnlilfslsisvslflmv mmtashlyfwdvwyiyhfckakikgyqrlispdccydafivydtkdpavtewvlael vakledprekhfnlcleerdwlpgqpvlenlsqsiqlskktvfvmtdkyaktenfki afylshqrlmdekvdviiliflekpfqkskflqlrkrlcgssvlewptnpqahpyfw qclknalatdnhvaysqvfketv

Figure 7

Amino acid sequence (SEQ ID NO: 35) of heavy chain (including signal sequence thereof) of cAT01 antibody and amino acid sequence (SEQ ID NO: 36) of light chain (including signal sequence thereof)

MKHLWFFLLLVAAPRWVLSQVQLQQPGAELVKPGASVNLSCKASGYTFTNNWLHWVK
QRPGRGLEWIGDIYPSNGRTNYNEQFKTKATLTVDKSSSTAYMQLSSLTSEDSAVYF
CARERGYFDYWGQGTALTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTK
VDKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQ
KSLSLSPGK (SEQ ID NO: 35)

MVLQTQVFISLLLWISGAYGDIQMTQSPSSLSTSLGGKVTITCKASQDINKYIAWYQ
HKPGKGPRLLIHYTSTLQPGIPSRFSGSGSGRDYSFSISNLEPEDIATYYCLQYDYL
LTFGAGTKLELKRAVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC (SEQ ID NO: 36)

Figure 8

Amino acid sequence (SEQ ID NO: 37) of heavy chain (including signal sequence thereof) of cNB7 antibody and amino acid sequence (SEQ ID NO: 38) of light chain (including signal sequence thereof)

MKHLWFFLLLVAAPRWVLSDVQLQESGPGLVKPSQSLSLTCTVTGYSITSDYAWNWI
RQFPGNKLEWMGHISYRGNTNYNPSLKSRISITRDTSKNQFFLQLNSVTTEDTATYY
CASWNYYGYVDYAMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTYICNVNH
KPSNTKVDKRVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEAL
HNHYTQKSLSLSPGK (SEQ ID NO: 37)

MVLQTQVFISLLLWISGAYGDIQMTQTPSSLSASLGDRVTISCRASQDISNYLNWYQ
QKPDGTVKLLIYYTSRLHSGVPSRFSGSGSGTDYSLTINNLEQEDIATYFCQQGDTF
PTFGGGTKLEIKRAVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC (SEQ ID NO: 38)

Figure 9

Amino acid sequence (SEQ ID NO: 39) of heavy chain (including signal sequence thereof) of cFAN2 antibody and amino acid sequence (SEQ ID NO: 40) of light chain (including signal sequence thereof)

MKHLWFFLLLVAAPRWVLSQVQLKESGPGLVAPSQSLSITCTVSGFSLTGYGVNWVR
QPPGKGLEWLGMIWGDGSTDYNSALKSRLSIRKDNSKSQVFLKMNSLQTDDTARYYC
ARDKGYDGYYYAMDYWGQGTSVTVSSASTKGPSVFPLAPSSKSTSGGTAALGCLVKD
YFPEPVTVSWNSGALTSGVHTFPAVLQSSGLYSLSSVVTVPSSSLGTQTYICNVNHK
PSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALH
NHYTQKSLSLSPGK (SEQ ID NO: 39)

MVLQTQVFISLLLWISGAYGDIQMTQSPASLSASVGETVTITCRASENIYSYLAWYQ
QKQGKSPQLLVYDAKTLAEGVPSRFSGSGSGTQFSLKINSLQPEDFGSYYCQHHYGI
PYTFGGGTKLEIKRAVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKS
FNRGEC (SEQ ID NO: 40)

Figure 11

Amino acid sequence (SEQ ID NO: 45) (including signal sequence) of humanized heavy chain huAT01_H1_IgG1LALA MKHLWFFLLLVAAPRWVLSQVQLVQSGAEVKKPGASVKVSCKASGYTFTNNWLHWVR
QAPGQGLEWMGDIYPSNGRTNYAQKFQGRVTITADKSTSTAYMELSSLRSEDTAVYY
CARERGYFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTK
VDKRVEPKSCDKTHTCPPCPAPEAAGGPSVFLFPPKPKDTLMISRTPEVTCVVVDVS
HEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQ
KSLSLSPGK

Figure 12

Amino acid sequence (SEQ ID NO: 46) (including signal sequence) of humanized heavy chain huAT01_H3_IgG1LALA MKHLWFFLLLVAAPRWVLSQVQLVQSGAEVKKPGASVKVSCKASGYTFTNNWLHWVR
QAPGQGLEWMGDIYPSNGRTNYAQKFQGRVTLTVDKSTSTAYMELSSLRSEDTAVYF
CARERGYFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTK
VDKRVEPKSCDKTHTCPPCPAPEAAGGPSVFLFPPKPKDTLMISRTPEVTCVVVDVS
HEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQ
KSLSLSPGK

Figure 13

Amino acid sequence (SEQ ID NO: 47) (including signal sequence) of humanized heavy chain huAT01_H3_IgG4Pro MKHLWFFLLLVAAPRWVLSQVQLVQSGAEVKKPGASVKVSCKASGYTFTNNWLHWVR
QAPGQGLEWMGDIYPSNGRTNYAQKFQGRVTLTVDKSTSTAYMELSSLRSEDTAVYF
CARERGYFDYWGQGTLVTVSSASTKGPSVFPLAPCSRSTSESTAALGCLVKDYFPEP
VTVSWNSGALTSGVHTFPAVLQSSGLYSLSSVVTVPSSSLGTKTYTCNVDHKPSNTK
VDKRVESKYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSL
SLSLGK

Figure 14

```
cbAT01_H     1 QVQLQQPGAELVKPGASVNLSCKASGYTFTNNWLHWVKQRPGRGLEWIGDIYPSNGRTNY 60
huAT01_H1    1 ....V.S...VK......KV.................R.A..Q....M............ 60
huAT01_H3    1 ....V.S...VK......KV.................R.A..Q....M............ 60

cbAT01_H    61 NEQFKTKATLTVDKSSSTAYMQLSSLTSEDSAVYFCARERGYFDYWGQGTALTVSS     116
huAT01_H1   61 AQK.QGRV.I.A...T.....E....R...T...Y...............LV....     116
huAT01_H3   61 AQK.QGRV.......T.....E....R...T...................LV....     116
```

Figure 15

Amino acid sequence (SEQ ID NO: 48) (including signal sequence) of humanized light chain huAT01_L1

MVLQTQVFISLLLWISGAYGDIQMTQSPSSLSASVGDRVTITCKASQDINKYIAWYQ
QKPGKAPKLLIHYTSTLQPGVPSRFSGSGSGRDFTLTISSLQPEDFATYYCLQYDYL
LTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC

Figure 16

Amino acid sequence (SEQ ID NO: 49) (including signal sequence) of humanized light chain huAT01_L2

MVLQTQVFISLLLWISGAYGDIQMTQSPSSLSASVGDRVTITCKASQDINKYIAWYQ
QKPGKAPKLLIHYTSTLQPGIPSRFSGSGSGRDYTLTISSLQPEDFATYYCLQYDYL
LTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC

Figure 17

```
chAT01_L     1 DIQMTQSPSSLSTSLGGKVTITCKASQDINKYIAWYQHKPGKGPRLLIHYTSTLQPGIPS 60
huAT01_L1    1 ............A.V.DR...................Q....A.K............V.. 60
huAT01_L2    1 ............A.V.DR...................Q....A.K............... 60

chAT01_L    61 RFSGSGSGRDYSFSISNLEPEDIATYYCLQYDYLLTFGAGTKLELK               106
huAT01_L1   61 ..........FTLT..S.Q...F...............Q...V.I.               106
huAT01_L2   61 ...........TLT..S.Q...F...............Q...V.I.               106
```

Figure 18

Amino acid sequence (SEQ ID NO: 52) (including signal sequence) of humanized heavy chain huNB7_H3_IgG1LALA MKHLWFFLLLVAAPRWVLSDVQLQESGPGLVKPSDTLSLTCTVTGYSITSDYAWNWI
RQPPGNKLEWIGHISYRGNTNYNPSLKSRVTISRDTSKNQFSLKLSSVTAADTAVYY
CASWNYYGYVDYAMDYWGQGTTVTVSSASTKGPSVFPLAPSSKSTSGGTAALGCLVK
DYFPEPVTVSWNSGALTSGVHTFPAVLQSSGLYSLSSVVTVPSSSLGTQTYICNVNH
KPSNTKVDKRVEPKSCDKTHTCPPCPAPEAAGGPSVFLFPPKPKDTLMISRTPEVTC
VVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEAL
HNHYTQKSLSLSPGK

Figure 19

Amino acid sequence (SEQ ID NO: 54) (including signal sequence) of humanized heavy chain huNB7_H3_IgG4Pro MKHLWFFLLLVAAPRWVLSDVQLQESGPGLVKPSDTLSLTCTVTGYSITSDYAWNWI
RQPPGNKLEWIGHISYRGNTNYNPSLKSRVTISRDTSKNQFSLKLSSVTAADTAVYY
CASWNYYGYVDYAMDYWGQGTTVTVSSASTKGPSVFPLAPCSRSTSESTAALGCLVK
DYFPEPVTVSWNSGALTSGVHTFPAVLQSSGLYSLSSVVTVPSSSLGTKTYTCNVDH
KPSNTKVDKRVESKYGPPCPPCPAPEFLGGPSVFLFPPKPKDTLMISRTPEVTCVVV
DVSQEDPEVQFNWYVDGVEVHNAKTKPREEQFNSTYRVVSVLTVLHQDWLNGKEYKC
KVSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEALHNH
YTQKSLSLSLGK

Figure 20

```
chNB7_H     1 DVQLQESGPGLVKPSQSLSLTCTVTGYSITSDYAWNWIRQFPGNKLEWMGHISYRGNTNY 60
huNB7_H3    1 ...............DT.......................P......I............ 60

chNB7_H    61 NPSLKSRISITRDTSKNQFFLQLNSVTTEDTATYYCASWNYYGYVDYAMDYWGQGTSVTV 120
huNB7_H3   61 .......VT.S........S.K.S...AA..V........................T... 120

chNB7_H   121 SS                                                           122
huNB7_H3  121 ..                                                           122
```

Figure 21

Amino acid sequence (SEQ ID NO: 53) (including signal sequence) of humanized light chain huNB7_L3

MVLQTQVFISLLLWISGAYGDIQMTQSPSSLSASVGDRVTITCRASQDISNYLNWYQ
QKPGKAVKLLIYYTSRLHSGVPSRFSGSGSGTDYTLTISSLQPEDFATYFCQQGDTF
PTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC

Figure 22

```
chNB7_L    1 DIQMTQTPSSLSASLGDRVTISCRASQDISNYLNWYQQKPDGTVKLLIYYTSRLHSGVPS 60
huNB7_L3   1 ......S.......V......T..................GKA................. 60

chNB7_L   61 RFSGSGSGTDYSLTINNLEQEDIATYFCQQGDTFPTFGGGTKLEIK               106
huNB7_L3  61 ...........T...SS.QP..F...............Q...V...               106
```

Figure 24

Figure 24-1

Amino acid sequence of CDRs of the AT01 antibody

Amino acid sequence (SEQ ID NO: 17) of CDRH1: GYTFTNNWLH

Amino acid sequence (SEQ ID NO: 18) of CDRH2: DIYPSNGRTN

Amino acid sequence (SEQ ID NO: 19) of CDRH3: ERGYFDY

Amino acid sequence (SEQ ID NO: 20) of CDRL1: KASQDINKYIA

Amino acid sequence (SEQ ID NO: 21) of CDRL2: YTSTLQP

Amino acid sequence (SEQ ID NO: 22) of CDRL3: LQYDYLLT

Figure 24-2

Amino acid sequence of CDRs of the NB7 antibody

Amino acid sequence (SEQ ID NO: 23) of CDRH1: GYSITSDYAWN

Amino acid sequence (SEQ ID NO: 24) of CDRH2: HISYRGNTN

Amino acid sequence (SEQ ID NO: 25) of CDRH3:

WNYYGYVDYAMDY

Amino acid sequence (SEQ ID NO: 26) of CDRL1: RASQDISNYLN

Amino acid sequence (SEQ ID NO: 27) of CDRL2: YTSRLHS

Amino acid sequence (SEQ ID NO: 28) of CDRL3: QQGDTFPT

Figure 24-3

Amino acid sequence of CDRs of the FAN2 antibody

Amino acid sequence (SEQ ID NO: 29) of CDRH1: GFSLTGYGVN

Amino acid sequence (SEQ ID NO: 30) of CDRH2: MIWGDGSTD

Amino acid sequence (SEQ ID NO: 31) of CDRH3:

DKGYDGYYYAMDY

Amino acid sequence (SEQ ID NO: 32) of CDRL1: RASENIYSYLA

Amino acid sequence (SEQ ID NO: 33) of CDRL2: DAKTLAE

Amino acid sequence (SEQ ID NO: 34) of CDRL3: QHHYGIPYT

SEQUENCE LISTING

```
Sequence total quantity: 87
SEQ ID NO: 1            moltype = DNA  length = 3150
FEATURE                 Location/Qualifiers
source                  1..3150
                        mol_type = other DNA
                        organism = Homo sapiens
SEQUENCE: 1
atggtgtttc caatgtggac actgaagaga caaattctta tcctttttaa cataatccta  60
atttccaaac tccttggggc tagatggttt cctaaaactc tgccctgtga tgtcactctg  120
gatgttccaa agaaccatgt gatcgtggac tgcacagaca agcatttgac agaaattcct  180
ggaggtattc ccacgaacac cacgaacctc accctcacca ttaaccacat accagacatc  240
tccccagcgt cctttcacag actggaccat ctggtagaga tcgatttcag atgcaactgt  300
gtacctattc cactggggtc aaaaaacaac atgtgcatca agaggctgca gattaaaccc  360
agaagcttta gtggactcac ttatttaaaa tccctttacc tggatggaaa ccagctacta  420
gagataccgc agggcctccc gcctagctta cagcttctca gccttgaggc caacaacatc  480
ttttccatca gaaaagagaa tctaacagaa ctggccaaca tagaaatact ctacctgggc  540
caaaactgtt attatcgaaa tccttgttat gtttcatatt caatagagaa agatgccttc  600
ctaaacttga caaagttaaa agtgctctcc ctgaaagata acaatgtcac agccgtccct  660
actgttttgc catctacttt aacagaacta tatctctaca acaacatgat tgcaaaaatc  720
caagaagatg attttaataa cctcaaccaa ttacaaattc ttgacctaag tggaaattgc  780
cctcgttgtt ataatgcccc atttccttgt gcgccgtgta aaaataattc tcccctacag  840
atccctgtaa atgcttttga tgcgctgaca gaattaaaag ttttacgtct acacagtaac  900
tctcttcagc atgtgccccc aagatggttt aagaacatca acaaactcca ggaactggat  960
ctgtcccaaa acttcttggc caaagaaatt ggggatgcta aatttctgca ttttctcccc  1020
agcctcatcc aattggatct gtctttcaat tttgaacttc aggtctatcg tgcatctatg  1080
aatctatcac aagcattttc ttcactgaaa agcctgaaaa ttctgcggat cagaggatat  1140
```

-continued

```
gtctttaaag agttgaaaag ctttaacctc tcgccattac ataatcttca aaatcttgaa  1200
gttcttgatc ttggcactaa ctttataaaa attgctaacc tcagcatgtt taaacaattt  1260
aaaagactga aagtcataga tctttcagtg aataaaatat caccttcagg agattcaagt  1320
gaagttggct tctgctcaaa tgccagaact tctgtagaaa gttatgaacc ccaggtcctg  1380
gaacaattac attatttcag atatgataag tatgcaagga gttgcagatt caaaaacaaa  1440
gaggcttctt tcatgtctgt taatgaaagc tgctacaagt atgggcagac cttggatcta  1500
agtaaaaata gtatattttt tgtcaagtcc tctgattttc agcatctttc tttcctcaaa  1560
tgcctgaatc tgtcaggaaa tctcattagc caaactctta atggcagtga attccaacct  1620
ttagcagagc tgagatattt ggacttctcc aacaaccggc ttgatttact ccattcaaca  1680
gcatttgaag agcttcacaa actggaagtt ctggatataa gcagtaatag ccattatttt  1740
caatcagaag gaattactca tatgctaaac tttaccaaga acctaaaggt tctgcagaaa  1800
ctgatgatga acgacaatga catctcttcc tccaccagca ggaccatgga gagtgagtct  1860
cttagaactc tggaattcag aggaaatcac ttagatgttt tatggagaga aggtgataac  1920
agatacttac aattattcaa gaatctgcta aaattagagg aattagacat ctctaaaaat  1980
tccctaagtt tcttgccttc tggagttttt gatggtatgc ctccaaatct aaagaatctc  2040
tctttggcca aaaatgggct caaatctttc agttggaaga aactccagtg tctaaagaac  2100
ctggaaactt tggacctcag ccacaaccaa ctgaccactg tccctgagag attatccaac  2160
tgttccagaa gcctcaagaa tctgattctt aagaataatc aaatcaggag tctgacgaag  2220
tattttctac aagatgcctt ccagttgcga tatctggatc tcagctcaaa taaaatccag  2280
atgatccaaa agaccagctt cccagaaaat gtcctcaaca atctgaagat gttgcttttg  2340
catcataatc ggtttctgtg cacctgtgat gctgtgtggt ttgtctggtg ggttaaccat  2400
acggaggtga ctattcctta cctggccaca gatgtgactt gtgtggggcc aggagcacac  2460
aagggccaaa gtgtgatctc cctggatctg tacacctgtg agttagatct gactaacctg  2520
attctgttct cactttccat atctgtatct ctctttctca tggtgatgat gacagcaagt  2580
cacctctatt tctgggatgt gtggtatatt taccatttct gtaaggccaa gataaagggg  2640
tatcagcgtc taatatcacc agactgttgc tatgatgctt ttattgtgta tgacactaaa  2700
gacccagctg tgaccgagtg ggttttggct gagctggtgg ccaaactgga agacccaaga  2760
gagaaacatt ttaatttatg tctcgaggaa agggactggt taccagggca gccagttctg  2820
gaaaaccttt cccagagcat acagcttagc aaaaagacag tgtttgtgat gacagacaag  2880
tatgcaaaga ctgaaaattt taagatagca ttttacttgt cccatcagag gctcatggat  2940
gaaaaagttg atgtgattat cttgatattt cttgagaagc cctttcagaa gtccaagttc  3000
ctccagctcc ggaaaaggct ctgtgggagt tctgtccttg agtggccaac aaacccgcaa  3060
gctcacccat acttctggca gtgtctaaag aacgccctgg ccacagacaa tcatgtggcc  3120
tatagtcagg tgttcaagga aacggtctag                                    3150

SEQ ID NO: 2           moltype = AA  length = 1049
FEATURE                Location/Qualifiers
source                 1..1049
                       mol_type = protein
                       organism = Homo sapiens
SEQUENCE: 2
MVFPMWTLKR QILILFNIIL ISKLLGARWF PKTLPCDVTL DVPKNHVIVD CTDKHLTEIP  60
GGIPTNTTNL TLTINHIPDI SPASFHRLDH LVEIDFRCNC VPIPLGSKNN MCIKRLQIKP  120
RSFSGLTYLK SLYLDGNQLL EIPQGLPPSL QLLSLEANNI FSIRKENLTE LANIEILYLG  180
QNCYYRNPCY VSYSIEKDAF LNLTKLKVLS LKDNNVTAVP TVLPSTLTEL YLYNNMIAKI  240
QEDDFNNLNQ LQILDLSGNC PRCYNAPFPC APCKNNSPLQ IPVNAFDALT ELKVLRLHSN  300
SLQHVPPRWF KNINKLQELD LSQNFLAKEI GDAKFLHFLP SLIQLDLSFN FELQVYRASM  360
NLSQAFSSLK SLKILRIRGY VFKELKSFNL SPLHNLQNLE VLDLGTNFIK IANLSMFKQF  420
KRLKVIDLSV NKISPSGDSS EVGFCSNART SVESYEPQVL EQLHYFRYDK YARSCRFKNK  480
EASFMSVNES CYKYGQTLDL SKNSIFFVKS SDFQHLSFLK CLNLSGNLIS QTLNGSEFQP  540
LAELRYLDFS NNRLDLLHST AFEELHKLEV LDISSNSHYF QSEGITHMLN FTKNLKVLQK  600
LMMNDNDISS STSRTMESES LRTLEFRGNH LDVLWREGDN RYLQLFKNLL KLEELDISKN  660
SLSFLPSGVF DGMPPNLKNL SLAKNGLKSF SWKKLQCLKN LETLDLSHNQ LTTVPERLSN  720
CSRSLKNLIL KNNQIRSLTK YFLQDAFQLR YLDLSSNKIQ MIQKTSFPEN VLNNLKMLLL  780
HHNRFLCTCD AVWFVWWVNH TEVTIPYLAT DVTCVGPGAH KGQSVISLDL YTCELDLTNL  840
ILFSLSISVS LFLMVMMTAS HLYFWDVWYI YHFCKAKIKG YQRLISPDCC YDAFIVYDTK  900
DPAVTEWVLA ELVAKLEDPR EKHFNLCLEE RDWLPGQPVL ENLSQSIQLS KKTVFVMTDK  960
YAKTENFKIA FYLSHQRLMD EKVDVIILIF LEKPFQKSKF LQLRKRLCGS SVLEWPTNPQ  1020
AHPYFWQCLK NALATDNHVA YSQVFKETV                                     1049

SEQ ID NO: 3           moltype = DNA  length = 3150
FEATURE                Location/Qualifiers
source                 1..3150
                       mol_type = other DNA
                       organism = Homo sapiens
SEQUENCE: 3
atggtgtttc caatgtggac actgaagaga caaattctta tcctttttaa cataatccta  60
atttccaaac tccttggggc tagatggttt cctaaaactc tgccctgtga tgtcactctg  120
gatgttccaa agaaccatgt gatcgtggac tgcacagaca agcatttgac agaaattcct  180
ggaggtattc ccacgaacac cacgaacctc accctcacca ttaaccacat accagacatc  240
tccccagcgt cctttcacag actggaccat ctggtagaga tcgatttcag atgcaactgt  300
gtacctattc cactggggtc aaaaaacaac atgtgcatca agaggctgca gattaaaccc  360
agaagcttta gtggactcac ttatttaaaa tccctttacc tggatggaaa ccagctacta  420
gagataccgc agggcctccc gcctagctta cagcttctca gccttgaggc caacaacatc  480
ttttccatca gaaaagagaa tctaacagaa ctggccaaca tagaaatact ctacctgggc  540
caaaactgtt attatcgaaa tccttgttat gtttcatatt caatagagaa agatgccttc  600
ctaaacttga caaagttaaa agtgctctcc ctgaaagata acaatgtcac agccgtccct  660
actgttttgc catctacttt aacagaacta tatctctaca acaacatgat tgcaaaaatc  720
caagaagatg attttaataa cctcaaccaa ttacaaattc ttgacctaag tggaaattgc  780
```

```
cctcgttgtt ataatgcccc atttccttgt gcgccgtgta aaaataattc tcccctacag  840
atccctgtaa atgcttttga tgcgctgaca gaattaaaag ttttacgtct acacagtaac  900
tctcttcagc atgtgccccc aagatggttt aagaacatca acaaactcca ggaactggat  960
ctgtcccaaa acttcttggc caaagaaatt ggggatgcta aatttctgca ttttctcccc  1020
agcctcatcc aattggatct gtctttcaat tttgaacttc aggtctatcg tgcatctatg  1080
aatctatcac aagcattttc ttcactgaaa agcctgaaaa ttctgcggat cagaggatat  1140
gtctttaaag agttgaaaag ctttaacctc tcgccattac ataatcttca aaatcttgaa  1200
gttcttgatc ttggcactaa ctttataaaa attgctaacc tcagcatgtt taaacaattt  1260
aaaagactga aagtcataga tctttcagtg aataaaatat caccttcagg agattcaagt  1320
gaagttggct tctgctcaaa tgccagaact tctgtagaaa gttatgaacc ccaggtcctg  1380
gaacaattac attatttcag atatgataag tatgcaagga gttgcagatt caaaaacaaa  1440
gaggcttctt tcatgtctgt taatgaaagc tgctacaagt atgggcagac cttggatcta  1500
agtaaaaata gtatattttt tgtcaagtcc tctgattttc agcatctttc tttcctcaaa  1560
tgcctgaatc tgtcaggaaa tctcattagc caaactctta atggcagtga attccaacct  1620
ttagcagagt tgagatattt ggacttctcc aacaaccggc ttgatttact ccattcaaca  1680
gcatttgaag agcttcacaa actggaagtt ctggatataa gcagtaatag ccattatttt  1740
caatcagaag gaattactca tatgctaaac tttaccaaga acctaaaggt tctgcagaaa  1800
ctgatgatga acgacaatga catctcttcc tccaccagca ggaccatgga gagtgagtct  1860
cttagaactc tggaattcag aggaaatcac ttagatgttt tatggagaga aggtgataac  1920
agatacttac aattattcaa gaatctgcta aaattagagg aattagacat ctctaaaaat  1980
tccctaagtt tcttgccttc tggagttttt gatggtatgc ctccaaatct aaagaatctc  2040
tctttggcca aaaatgggct caaatctttc agttggaaga aactccagtg tctaaagaac  2100
ctggaaactt tggacctcag ccacaaccaa ctgaccactg tccctgagag attatccaac  2160
tgttccagaa gccacaagaa tctgattctt aagaataatc aaatcaggag tccgacgaag  2220
tattttctac aagatgcctt ccagttgcga tatctggatc tcagctcaaa taaaatccag  2280
atgatccaaa agaccagctt cccagaaaat gtcctcaaca atctgaagat gttgcttttg  2340
catcataatc ggtttctgtg cacctgtgat gctgtgtggt ttgtctggtg ggttaaccat  2400
acggaggtga ctattcctta cctggccaca gatgtgactt gtgtggggcc aggagcacac  2460
aagggccaaa gtgtgatctc cctggatctg tacacctgtg agttagatct gactaacctg  2520
attctgttct cactttccat atctgtatct ctctttctca tggtgatgat gacagcaagt  2580
cacctctatt tctgggatgt gtggtatatt taccatttct gtaaggccaa gataaagggg  2640
tatcagcgtc taatatcacc agactgttgc tatgatgctt ttattgtgta tgacactaaa  2700
gacccagctg tgaccgagtg ggttttggct gagctggtgg ccaaactgga agacccaaga  2760
gagaaacatt ttaatttatg tctcgaggaa agggactggt taccagggca gccagttctg  2820
gaaaaccttt cccagagcat acagcttagc aaaaagacag tgtttgtgat gacagacaag  2880
tatgcaaaga ctgaaaattt taagatagca ttttacttgt cccatcagag gctcatggat  2940
gaaaaagttg atgtgattat cttgatattt cttgagaagc cctttcagaa gtccaagttc  3000
ctccagctcc ggaaaaggct ctgtgggagt tctgtccttg agtggccaac aaacccgcaa  3060
gctcacccat acttctggca gtgtctaaag aacgccctgg ccacagacaa tcatgtggcc  3120
tatagtcagg tgttcaagga aacggtctag                                   3150

SEQ ID NO: 4            moltype = AA  length = 1049
FEATURE                 Location/Qualifiers
source                  1..1049
                        mol_type = protein
                        organism = Homo sapiens
SEQUENCE: 4
MVFPMWTLKR QILILFNIIL ISKLLGARWF PKTLPCDVTL DVPKNHVIVD CTDKHLTEIP  60
GGIPTNTTNL TLTINHIPDI SPASFHRLDH LVEIDFRCNC VPIPLGSKNN MCIKRLQIKP  120
RSFSGLTYLK SLYLDGNQLL EIPQGLPPSL QLLSLEANNI FSIRKENLTE LANIEILYLG  180
QNCYYRNPCY VSYSIEKDAF LNLTKLKVLS LKDNNVTAVP TVLPSTLTEL YLYNNMIAKI  240
QEDDFNNLNQ LQILDLSGNC PRCYNAPFPC APCKNNSPLQ IPVNAFDALT ELKVLRLHSN  300
SLQHVPPRWF KNINKLQELD LSQNFLAKEI GDAKFLHFLP SLIQLDLSFN FELQVYRASM  360
NLSQAFSSLK SLKILRIRGY VFKELKSFNL SPLHNLQNLE VLDLGTNFIK IANLSMFKQF  420
KRLKVIDLSV NKISPSGDSS EVGFCSNART SVESYEPQVL EQLHYFRYDK YARSCRFKNK  480
EASFMSVNES CYKYGQTLDL SKNSIFFVKS SDFQHLSFLK CLNLSGNLIS QTLNGSEFQP  540
LAELRYLDFS NNRLDLLHST AFEELHKLEV LDISSNSHYF QSEGITHMLN FTKNLKVLQK  600
LMMNDNDISS STSRTMESES LRTLEFRGNH LDVLWREGDN RYLQLFKNLL KLEELDISKN  660
SLSFLPSGVF DGMPPNLKNL SLAKNGLKSF SWKKLQCLKN LETLDLSHNQ LTTVPERLSN  720
CSRSHKNLIL KNNQIRSPTK YFLQDAFQLR YLDLSSNKIQ MIQKTSFPEN VLNNLKMLLL  780
HHNRFLCTCD AVWFVWWVNH TEVTIPYLAT DVTCVGPGAH KGQSVISLDL YTCELDLTNL  840
ILFSLSISVS LFLMVMMTAS HLYFWDVWYI YHFCKAKIKG YQRLISPDCC YDAFIVYDTK  900
DPAVTEWVLA ELVAKLEDPR EKHFNLCLEE RDWLPGQPVL ENLSQSIQLS KKTVFVMTDK  960
YAKTENFKIA FYLSHQRLMD EKVDVIILIF LEKPFQKSKF LQLRKRLCGS SVLEWPTNPQ  1020
AHPYFWQCLK NALATDNHVA YSQVFKETV                                    1049

SEQ ID NO: 5            moltype = AA  length = 116
FEATURE                 Location/Qualifiers
source                  1..116
                        mol_type = protein
                        organism = Mus musculus
SEQUENCE: 5
QVQLQQPGAE LVKPGASVNL SCKASGYTFT NNWLHWVKQR PGRGLEWIGD IYPSNGRTNY  60
NEQFKTKATL TVDKSSSTAY MQLSSLTSED SAVYFCARER GYFDYWGQGT ALTVSS      116

SEQ ID NO: 6            moltype = DNA  length = 348
FEATURE                 Location/Qualifiers
source                  1..348
                        mol_type = other DNA
```

```
                          organism = Mus musculus
SEQUENCE: 6
caggtgcagc tgcagcagcc tggcgccgaa ctcgtgaaac ctggcgcctc cgtgaacctg  60
agctgcaagg ccagcggcta caccttcacc aacaactggc tgcactgggt caagcagagg  120
cccggcagag gcctggaatg gatcggcgac atctacccca gcaacggccg gaccaactac  180
aacgagcagt tcaagaccaa ggccaccctg accgtggaca agagcagcag caccgcctac  240
atgcagctgt ccagcctgac cagcgaggac agcgccgtgt acttctgcgc cagagagcgg  300
ggctacttcg actattgggg ccagggaacc gctctgaccg tcagctca              348

SEQ ID NO: 7              moltype = AA  length = 122
FEATURE                   Location/Qualifiers
source                    1..122
                          mol_type = protein
                          organism = Mus musculus
SEQUENCE: 7
DVQLQESGPG LVKPSQSLSL TCTVTGYSIT SDYAWNWIRQ FPGNKLEWMG HISYRGNTNY  60
NPSLKSRISI TRDTSKNQFF LQLNSVTTED TATYYCASWN YYGYVDYAMD YWGQGTSVTV  120
SS                                                                122

SEQ ID NO: 8              moltype = DNA  length = 366
FEATURE                   Location/Qualifiers
source                    1..366
                          mol_type = other DNA
                          organism = Mus musculus
SEQUENCE: 8
gacgtgcagc tgcaggaatc tggccctggc ctcgtgaagc ctagccagag cctgagcctg  60
acatgcaccg tgaccggcta cagcatcacc agcgactacg cctggaactg gatccggcag  120
ttccccggca acaagctgga atggatgggc cacatcagct accggggcaa caccaactac  180
aaccccagcc tgaagtcccg gatctccatc acccgggaca ccagcaagaa ccagttcttt  240
ctgcagctga acagcgtgac caccgaggac accgccacct actactgcgc cagctggaac  300
tactacggct acgtggacta tgccatggac tactggggcc agggcacctc cgtgaccgtc  360
agctca                                                            366

SEQ ID NO: 9              moltype = AA  length = 121
FEATURE                   Location/Qualifiers
source                    1..121
                          mol_type = protein
                          organism = Mus musculus
SEQUENCE: 9
QVQLKESGPG LVAPSQSLSI TCTVSGFSLT GYGVNWVRQP PGKGLEWLGM IWGDGSTDYN  60
SALKSRLSIR KDNSKSQVFL KMNSLQTDDT ARYYCARDKG YDGYYYAMDY WGQGTSVTVS  120
S                                                                 121

SEQ ID NO: 10             moltype = DNA  length = 363
FEATURE                   Location/Qualifiers
source                    1..363
                          mol_type = other DNA
                          organism = Mus musculus
SEQUENCE: 10
caggtgcagc tgaaagagtc tggccctgga ctggtggccc ctagccagag cctgagcatc  60
acctgtaccg tgtccggctt cagcctgacc ggctacggcg tgaactgggt gcgccagcct  120
cctggcaaag gcctggaatg gctgggcatg atctggggcg acggcagcac cgactacaac  180
agcgccctga agtcccggct gagcatccgg aaggacaaca gcaagtccca ggtgttcctg  240
aagatgaaca gcctgcagac cgacgacacc gcccggtact actgcgccag agacaagggc  300
tacgacggct actactacgc catggactac tggggccagg gcacctctgt gaccgtcagc  360
tca                                                               363

SEQ ID NO: 11             moltype = AA  length = 106
FEATURE                   Location/Qualifiers
source                    1..106
                          mol_type = protein
                          organism = Mus musculus
SEQUENCE: 11
DIQMTQSPSS LSTSLGGKVT ITCKASQDIN KYIAWYQHKP GKGPRLLIHY TSTLQPGIPS  60
RFSGSGSGRD YSFSISNLEP EDIATYYCLQ YDYLLTFGAG TKLELK                106

SEQ ID NO: 12             moltype = DNA  length = 318
FEATURE                   Location/Qualifiers
source                    1..318
                          mol_type = other DNA
                          organism = Mus musculus
SEQUENCE: 12
gacatccaga tgacccagag ccctagcagc ctgagcacaa gcctgggcgg caaagtgacc  60
atcacatgca aggccagcca ggacatcaac aagtatatcg cctggtatca gcacaaaccc  120
ggcaagggcc ccagactgct gattcactac accagcaccc tgcagcccgg catccccagc  180
agatttctg gcagcggctc cggcagagac tacagcttca gcatcagcaa cctggaaccc  240
gaggatatcg ccacctacta ctgcctgcag tacgactacc tgctgacctt cggagccggc  300
accaagctgg aactgaag                                               318
```

-continued

```
SEQ ID NO: 13          moltype = AA  length = 106
FEATURE                Location/Qualifiers
source                 1..106
                       mol_type = protein
                       organism = Mus musculus
SEQUENCE: 13
DIQMTQTPSS LSASLGDRVT ISCRASQDIS NYLNWYQQKP DGTVKLLIYY TSRLHSGVPS  60
RFSGSGSGTD YSLTINNLEQ EDIATYFCQQ GDTFPTFGGG TKLEIK                106

SEQ ID NO: 14          moltype = DNA  length = 318
FEATURE                Location/Qualifiers
source                 1..318
                       mol_type = other DNA
                       organism = Mus musculus
SEQUENCE: 14
gacatccaga tgacccagac acccagcagc ctgagcgcca gcctgggcga tagagtgacc  60
atcagctgca gagccagcca ggacatcagc aactacctga actggtatca gcagaaaccc  120
gacggcaccg tgaagctgct gatctactac accagcagac tgcacagcgg cgtgcccagc  180
agattttctg gcagcggctc cggcaccgac tacagcctga ccatcaacaa cctggaacag  240
gaagatatcg ctacctactt ctgtcagcaa ggcgacacct tccccacctt cggcggaggc  300
accaagctgg aaatcaag                                                318

SEQ ID NO: 15          moltype = AA  length = 107
FEATURE                Location/Qualifiers
source                 1..107
                       mol_type = protein
                       organism = Mus musculus
SEQUENCE: 15
DIQMTQSPAS LSASVGETVT ITCRASENIY SYLAWYQQKQ GKSPQLLVYD AKTLAEGVPS  60
RFSGSGSGTQ FSLKINSLQP EDFGSYYCQH HYGIPYTFGG GTKLEIK               107

SEQ ID NO: 16          moltype = DNA  length = 321
FEATURE                Location/Qualifiers
source                 1..321
                       mol_type = other DNA
                       organism = Mus musculus
SEQUENCE: 16
gacatccaga tgacacagtc tcccgccagc ctgagcgcct ctgtgggaga gacagtgacc  60
atcacctgtc gggccagcga gaacatctac agctacctgg cctggtatca gcagaagcag  120
ggcaagagcc cccagctgct ggtgtacgat gccaagacac tggccgaggg cgtgcccagc  180
agattttctg gcagcggctc cggcacccag ttcagcctga agatcaacag cctgcagccc  240
gaggacttcg gcagctacta ctgccagcac cactacggca tcccttacac cttcggcgga  300
ggcaccaagc tggaaatcaa g                                            321

SEQ ID NO: 17          moltype = AA  length = 10
FEATURE                Location/Qualifiers
source                 1..10
                       mol_type = protein
                       organism = Mus musculus
SEQUENCE: 17
GYTFTNNWLH                                                         10

SEQ ID NO: 18          moltype = AA  length = 10
FEATURE                Location/Qualifiers
source                 1..10
                       mol_type = protein
                       organism = Mus musculus
SEQUENCE: 18
DIYPSNGRTN                                                         10

SEQ ID NO: 19          moltype = AA  length = 7
FEATURE                Location/Qualifiers
source                 1..7
                       mol_type = protein
                       organism = Mus musculus
SEQUENCE: 19
ERGYFDY                                                            7

SEQ ID NO: 20          moltype = AA  length = 11
FEATURE                Location/Qualifiers
source                 1..11
                       mol_type = protein
                       organism = Mus musculus
SEQUENCE: 20
KASQDINKYI A                                                       11

SEQ ID NO: 21          moltype = AA  length = 7
FEATURE                Location/Qualifiers
source                 1..7
```

```
                        mol_type = protein
                        organism = Mus musculus
SEQUENCE: 21
YTSTLQP                                                7

SEQ ID NO: 22           moltype = AA  length = 8
FEATURE                 Location/Qualifiers
source                  1..8
                        mol_type = protein
                        organism = Mus musculus
SEQUENCE: 22
LQYDYLLT                                               8

SEQ ID NO: 23           moltype = AA  length = 11
FEATURE                 Location/Qualifiers
source                  1..11
                        mol_type = protein
                        organism = Mus musculus
SEQUENCE: 23
GYSITSDYAW N                                           11

SEQ ID NO: 24           moltype = AA  length = 9
FEATURE                 Location/Qualifiers
source                  1..9
                        mol_type = protein
                        organism = Mus musculus
SEQUENCE: 24
HISYRGNTN                                              9

SEQ ID NO: 25           moltype = AA  length = 13
FEATURE                 Location/Qualifiers
source                  1..13
                        mol_type = protein
                        organism = Mus musculus
SEQUENCE: 25
WNYYGYVDYA MDY                                         13

SEQ ID NO: 26           moltype = AA  length = 11
FEATURE                 Location/Qualifiers
source                  1..11
                        mol_type = protein
                        organism = Mus musculus
SEQUENCE: 26
RASQDISNYL N                                           11

SEQ ID NO: 27           moltype = AA  length = 7
FEATURE                 Location/Qualifiers
source                  1..7
                        mol_type = protein
                        organism = Mus musculus
SEQUENCE: 27
YTSRLHS                                                7

SEQ ID NO: 28           moltype = AA  length = 8
FEATURE                 Location/Qualifiers
source                  1..8
                        mol_type = protein
                        organism = Mus musculus
SEQUENCE: 28
QQGDTFPT                                               8

SEQ ID NO: 29           moltype = AA  length = 10
FEATURE                 Location/Qualifiers
source                  1..10
                        mol_type = protein
                        organism = Mus musculus
SEQUENCE: 29
GFSLTGYGVN                                             10

SEQ ID NO: 30           moltype = AA  length = 9
FEATURE                 Location/Qualifiers
source                  1..9
                        mol_type = protein
                        organism = Mus musculus
SEQUENCE: 30
MIWGDGSTD                                              9

SEQ ID NO: 31           moltype = AA  length = 13
FEATURE                 Location/Qualifiers
```

```
source                  1..13
                        mol_type = protein
                        organism = Mus musculus
SEQUENCE: 31
DKGYDGYYYA MDY                                                     13

SEQ ID NO: 32           moltype = AA  length = 11
FEATURE                 Location/Qualifiers
source                  1..11
                        mol_type = protein
                        organism = Mus musculus
SEQUENCE: 32
RASENIYSYL A                                                       11

SEQ ID NO: 33           moltype = AA  length = 7
FEATURE                 Location/Qualifiers
source                  1..7
                        mol_type = protein
                        organism = Mus musculus
SEQUENCE: 33
DAKTLAE                                                            7

SEQ ID NO: 34           moltype = AA  length = 9
FEATURE                 Location/Qualifiers
source                  1..9
                        mol_type = protein
                        organism = Mus musculus
SEQUENCE: 34
QHHYGIPYT                                                          9

SEQ ID NO: 35           moltype = AA  length = 465
FEATURE                 Location/Qualifiers
REGION                  1..465
                        note = Synthetic
REGION                  1..465
                        note = MISC_FEATURE - Amino acid sequence of heavy chain of
                         chimeric anti-human TLR7 antibody AT01 (cAT01)
source                  1..465
                        mol_type = protein
                        organism = synthetic construct
SEQUENCE: 35
MKHLWFFLLL VAAPRWVLSQ VQLQQPGAEL VKPGASVNLS CKASGYTFTN NWLHWVKQRP  60
GRGLEWIGDI YPSNGRTNYN EQFKTKATLT VDKSSSTAYM QLSSLTSEDS AVYFCARERG  120
YFDYWGQGTA LTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KRVEPKSCDK  240
THTCPPCPAP ELLGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSREEMTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGK                  465

SEQ ID NO: 36           moltype = AA  length = 233
FEATURE                 Location/Qualifiers
REGION                  1..233
                        note = Synthetic
REGION                  1..233
                        note = MISC_FEATURE - Amino acid sequence of light chain of
                         chimeric anti-human TLR7 antibody AT01 (cAT01)
source                  1..233
                        mol_type = protein
                        organism = synthetic construct
SEQUENCE: 36
MVLQTQVFIS LLLWISGAYG DIQMTQSPSS LSTSLGGKVT ITCKASQDIN KYIAWYQHKP  60
GKGPRLLIHY TSTLQPGIPS RFSGSGSGRD YSFSISNLEP EDIATYYCLQ YDYLLTFGAG  120
TKLELKRAVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 37           moltype = AA  length = 471
FEATURE                 Location/Qualifiers
REGION                  1..471
                        note = Synthetic
REGION                  1..471
                        note = MISC_FEATURE - Amino acid sequence of heavy chain of
                         chimeric anti-human TLR7 antibody NB7 (cNB7)
source                  1..471
                        mol_type = protein
                        organism = synthetic construct
SEQUENCE: 37
MKHLWFFLLL VAAPRWVLSD VQLQESGPGL VKPSQSLSLT CTVTGYSITS DYAWNWIRQF  60
PGNKLEWMGH ISYRGNTNYN PSLKSRISIT RDTSKNQFFL QLNSVTTEDT ATYYCASWNY  120
```

-continued

```
YGYVDYAMDY WGQGTSVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 38           moltype = AA  length = 233
FEATURE                 Location/Qualifiers
REGION                  1..233
                        note = Synthetic
REGION                  1..233
                        note = MISC_FEATURE - Amino acid sequence of light chain of
                         chimeric anti-human TLR7 antibody NB7 (cNB7)
source                  1..233
                        mol_type = protein
                        organism = synthetic construct
SEQUENCE: 38
MVLQTQVFIS LLLWISGAYG DIQMTQTPSS LSASLGDRVT ISCRASQDIS NYLNWYQQKP  60
DGTVKLLIYY TSRLHSGVPS RFSGSGSGTD YSLTINNLEQ EDIATYFCQQ GDTFPTFGGG  120
TKLEIKRAVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 39           moltype = AA  length = 470
FEATURE                 Location/Qualifiers
REGION                  1..470
                        note = Synthetic
REGION                  1..470
                        note = MISC_FEATURE - Amino acid sequence of heavy chain of
                         chimeric anti-human TLR7 antibody FAN2 (cFAN2)
source                  1..470
                        mol_type = protein
                        organism = synthetic construct
SEQUENCE: 39
MKHLWFFLLL VAAPRWVLSQ VQLKESGPGL VAPSQSLSIT CTVSGFSLTG YGVNWVRQPP  60
GKGLEWLGMI WGDGSTDYNS ALKSRLSIRK DNSKSQVFLK MNSLQTDDTA RYYCARDKGY  120
DGYYYAMDYW GQGTSVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKRVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 40           moltype = AA  length = 234
FEATURE                 Location/Qualifiers
REGION                  1..234
                        note = Synthetic
REGION                  1..234
                        note = MISC_FEATURE - Amino acid sequence of light chain of
                         chimeric anti-human TLR7 antibody FAN2 (cFAN2)
source                  1..234
                        mol_type = protein
                        organism = synthetic construct
SEQUENCE: 40
MVLQTQVFIS LLLWISGAYG DIQMTQSPAS LSASVGETVT ITCRASENIY SYLAWYQQKQ  60
GKSPQLLVYD AKTLAEGVPS RFSGSGSGTQ FSLKINSLQP EDFGSYYCQH HYGIPYTFGG  120
GTKLEIKRAV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 41           moltype = AA  length = 116
FEATURE                 Location/Qualifiers
REGION                  1..116
                        note = Synthetic
REGION                  1..116
                        note = MISC_FEATURE - Amino acid sequence of heavy chain
                         variable region of huAT01_H1_IgG1LALA
source                  1..116
                        mol_type = protein
                        organism = synthetic construct
SEQUENCE: 41
QVQLVQSGAE VKKPGASVKV SCKASGYTFT NNWLHWVRQA PGQGLEWMGD IYPSNGRTNY  60
AQKFQGRVTI TADKSTSTAY MELSSLRSED TAVYYCARER GYFDYWGQGT LVTVSS      116

SEQ ID NO: 42           moltype = AA  length = 116
FEATURE                 Location/Qualifiers
REGION                  1..116
                        note = Synthetic
REGION                  1..116
                        note = MISC_FEATURE - Amino acid sequence of heavy chain
```

```
                          variable region of huAT01_H3_IgG1LALA
source                   1..116
                         mol_type = protein
                         organism = synthetic construct
SEQUENCE: 42
QVQLVQSGAE VKKPGASVKV SCKASGYTFT NNWLHWVRQA PGQGLEWMGD IYPSNGRTNY  60
AQKFQGRVTL TVDKSTSTAY MELSSLRSED TAVYFCARER GYFDYWGQGT LVTVSS      116

SEQ ID NO: 43            moltype = AA  length = 106
FEATURE                  Location/Qualifiers
REGION                   1..106
                         note = Synthetic
REGION                   1..106
                         note = MISC_FEATURE - Amino acid sequence of light chain
                          variable region of huAT01_L1
source                   1..106
                         mol_type = protein
                         organism = synthetic construct
SEQUENCE: 43
DIQMTQSPSS LSASVGDRVT ITCKASQDIN KYIAWYQQKP GKAPKLLIHY TSTLQPGVPS  60
RFSGSGSGRD FTLTISSLQP EDFATYYCLQ YDYLLTFGQG TKVEIK                 106

SEQ ID NO: 44            moltype = AA  length = 106
FEATURE                  Location/Qualifiers
REGION                   1..106
                         note = Synthetic
REGION                   1..106
                         note = MISC_FEATURE - Amino acid sequence of light chain
                          variable region of huAT01_L2
source                   1..106
                         mol_type = protein
                         organism = synthetic construct
SEQUENCE: 44
DIQMTQSPSS LSASVGDRVT ITCKASQDIN KYIAWYQQKP GKAPKLLIHY TSTLQPGIPS  60
RFSGSGSGRD YTLTISSLQP EDFATYYCLQ YDYLLTFGQG TKVEIK                 106

SEQ ID NO: 45            moltype = AA  length = 465
FEATURE                  Location/Qualifiers
REGION                   1..465
                         note = Synthetic
REGION                   1..465
                         note = MISC_FEATURE - Amino acid sequence of
                          huAT01_H1_IgG1LALA
source                   1..465
                         mol_type = protein
                         organism = synthetic construct
SEQUENCE: 45
MKHLWFFLLL VAAPRWVLSQ VQLVQSGAEV KKPGASVKVS CKASGYTFTN NWLHWVRQAP  60
GQGLEWMGDI YPSNGRTNYA QKFQGRVTIT ADKSTSTAYM ELSSLRSEDT AVYYCARERG  120
YFDYWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KRVEPKSCDK  240
THTCPPCPAP EAAGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSREEMTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGK                  465

SEQ ID NO: 46            moltype = AA  length = 465
FEATURE                  Location/Qualifiers
REGION                   1..465
                         note = Synthetic
REGION                   1..465
                         note = MISC_FEATURE - Amino acid sequence of
                          huAT01_H3_IgG1LALA
source                   1..465
                         mol_type = protein
                         organism = synthetic construct
SEQUENCE: 46
MKHLWFFLLL VAAPRWVLSQ VQLVQSGAEV KKPGASVKVS CKASGYTFTN NWLHWVRQAP  60
GQGLEWMGDI YPSNGRTNYA QKFQGRVTLT VDKSTSTAYM ELSSLRSEDT AVYFCARERG  120
YFDYWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KRVEPKSCDK  240
THTCPPCPAP EAAGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSREEMTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGK                  465

SEQ ID NO: 47            moltype = AA  length = 462
FEATURE                  Location/Qualifiers
REGION                   1..462
```

```
                        note = Synthetic
REGION                  1..462
                        note = MISC_FEATURE - Amino acid sequence of
                         huAT01_H3_IgG4Pro
source                  1..462
                        mol_type = protein
                        organism = synthetic construct
SEQUENCE: 47
MKHLWFFLLL VAAPRWVLSQ VQLVQSGAEV KKPGASVKVS CKASGYTFTN NWLHWVRQAP  60
GQGLEWMGDI YPSNGRTNYA QKFQGRVTLT VDKSTSTAYM ELSSLRSEDT AVYFCARERG  120
YFDYWGQGTL VTVSSASTKG PSVFPLAPCS RSTSESTAAL GCLVKDYFPE PVTVSWNSGA  180
LTSGVHTFPA VLQSSGLYSL SSVVTVPSSS LGTKTYTCNV DHKPSNTKVD KRVESKYGPP  240
CPPCPAPEFL GGPSVFLFPP KPKDTLMISR TPEVTCVVVD VSQEDPEVQF NWYVDGVEVH  300
NAKTKPREEQ FNSTYRVVSV LTVLHQDWLN GKEYKCKVSN KGLPSSIEKT ISKAKGQPRE  360
PQVYTLPPSQ EEMTKNQVSL TCLVKGFYPS DIAVEWESNG QPENNYKTTP PVLDSDGSFF  420
LYSRLTVDKS RWQEGNVFSC SVMHEALHNH YTQKSLSLSL GK                    462

SEQ ID NO: 48           moltype = AA  length = 233
FEATURE                 Location/Qualifiers
REGION                  1..233
                        note = Synthetic
REGION                  1..233
                        note = MISC_FEATURE - Amino acid sequence of huAT01_L1
source                  1..233
                        mol_type = protein
                        organism = synthetic construct
SEQUENCE: 48
MVLQTQVFIS LLLWISGAYG DIQMTQSPSS LSASVGDRVT ITCKASQDIN KYIAWYQQKP  60
GKAPKLLIHY TSTLQPGVPS RFSGSGSGRD FTLTISSLQP EDFATYYCLQ YDYLLTFGQG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 49           moltype = AA  length = 233
FEATURE                 Location/Qualifiers
REGION                  1..233
                        note = Synthetic
REGION                  1..233
                        note = MISC_FEATURE - Amino acid sequence of huAT01_L2
source                  1..233
                        mol_type = protein
                        organism = synthetic construct
SEQUENCE: 49
MVLQTQVFIS LLLWISGAYG DIQMTQSPSS LSASVGDRVT ITCKASQDIN KYIAWYQQKP  60
GKAPKLLIHY TSTLQPGIPS RFSGSGSGRD YTLTISSLQP EDFATYYCLQ YDYLLTFGQG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 50           moltype = AA  length = 122
FEATURE                 Location/Qualifiers
REGION                  1..122
                        note = Synthetic
REGION                  1..122
                        note = MISC_FEATURE - Amino acid sequence of heavy chain
                         variable region of huNB7_H3_IgG1LALA
source                  1..122
                        mol_type = protein
                        organism = synthetic construct
SEQUENCE: 50
DVQLQESGPG LVKPSDTLSL TCTVTGYSIT SDYAWNWIRQ PPGNKLEWIG HISYRGNTNY  60
NPSLKSRVTI SRDTSKNQFS LKLSSVTAAD TAVYYCASWN YYGYVDYAMD YWGQGTTVTV  120
SS                                                                122

SEQ ID NO: 51           moltype = AA  length = 106
FEATURE                 Location/Qualifiers
REGION                  1..106
                        note = Synthetic
REGION                  1..106
                        note = MISC_FEATURE - Amino acid sequence of light chain
                         variable region of huNB7_L3
source                  1..106
                        mol_type = protein
                        organism = synthetic construct
SEQUENCE: 51
DIQMTQSPSS LSASVGDRVT ITCRASQDIS NYLNWYQQKP GKAVKLLIYY TSRLHSGVPS  60
RFSGSGSGTD YTLTISSLQP EDFATYFCQQ GDTFPTFGQG TKVEIK                106

SEQ ID NO: 52           moltype = AA  length = 471
FEATURE                 Location/Qualifiers
REGION                  1..471
```

```
                        note = Synthetic
REGION                  1..471
                        note = MISC_FEATURE - Amino acid sequence of
                         huNB7_H3_IgG1LALA
source                  1..471
                        mol_type = protein
                        organism = synthetic construct
SEQUENCE: 52
MKHLWFFLLL VAAPRWVLSD VQLQESGPGL VKPSDTLSLT CTVTGYSITS DYAWNWIRQP  60
PGNKLEWIGH ISYRGNTNYN PSLKSRVTIS RDTSKNQFSL KLSSVTAADT AVYYCASWNY  120
YGYVDYAMDY WGQGTTVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPEAAG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 53           moltype = AA  length = 233
FEATURE                 Location/Qualifiers
REGION                  1..233
                        note = Synthetic
REGION                  1..233
                        note = MISC_FEATURE - Amino acid sequence of huNB7_L3
source                  1..233
                        mol_type = protein
                        organism = synthetic construct
SEQUENCE: 53
MVLQTQVFIS LLLWISGAYG DIQMTQSPSS LSASVGDRVT ITCRASQDIS NYLNWYQQKP  60
GKAVKLLIYY TSRLHSGVPS RFSGSGSGTD YTLTISSLQP EDFATYFCQQ GDTFPTFGQG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 54           moltype = AA  length = 468
FEATURE                 Location/Qualifiers
REGION                  1..468
                        note = Synthetic
REGION                  1..468
                        note = MISC_FEATURE - Amino acid sequence of
                         huNB7_H3_IgG4Pro
source                  1..468
                        mol_type = protein
                        organism = synthetic construct
SEQUENCE: 54
MKHLWFFLLL VAAPRWVLSD VQLQESGPGL VKPSDTLSLT CTVTGYSITS DYAWNWIRQP  60
PGNKLEWIGH ISYRGNTNYN PSLKSRVTIS RDTSKNQFSL KLSSVTAADT AVYYCASWNY  120
YGYVDYAMDY WGQGTTVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGK              468

SEQ ID NO: 55           moltype = DNA  length = 1794
FEATURE                 Location/Qualifiers
source                  1..1794
                        mol_type = genomic DNA
                        organism = Homo sapiens
SEQUENCE: 55
atggaggcgg agccgccgct ctacccgatg gcggggggctg cggggccgca gggcgacgag  60
gacctgctcg gggtcccgga cgggcccgag gccccgctgg acgagctggt gggcgcgtac  120
cccaactaca acgaggagga ggaggagcgc cgctactacc gccgcaagcg cctgggcgtg  180
ctcaagaacg tgctggctgc cagcgccggg ggcatgctca cctacggcgt ctacctgggc  240
ctcctgcaga tgcagctgat cctgcactac gacgagacct accgcgaggt gaagtatggc  300
aacatggggc tgcccgacat cgacagcaaa atgctgatgg gcatcaacgt gactcccatc  360
gccgccctgc tctacacacc tgtgctcatc aggtttttg gaacgaagtg gatgatgttc  420
ctcgctgtgg gcatctacgc cctctttgtc tccaccaact actgggagcg ctactacacg  480
cttgtgccct cggctgtggc cctgggcatg gccatcgtgc ctctttgggc ttccatgggc  540
aactacatca ccaggatggc gcagaagtac catgagtact cccactacaa ggagcaggat  600
gggcagggga tgaagcagcg gcctccgcgg ggctcccacg cgccctatct cctggtcttc  660
caagccatct tctacagctt cttccatctg agcttcgcct gcgcccagct gcccatgatt  720
tatttcctga accactacct gtatgacctg aaccacacgc tgtacaatgt gcagagctgc  780
ggcaccaaca gccacgggat cctcagcggc ttcaacaaga cggttctgcg gacgctcccg  840
cggagcggaa acctcattgt ggtggagagc gtgctcatgg cagtggcctt cctggccatg  900
ctgctggtgc tgggtttgtg cggagccgct taccggccca cggaggagat cgatctgcgc  960
agcgtgggct ggggcaacat cttccagctg cccttcaagc acgtgcgtga ctaccgcctg  1020
cgccacctcg tgcctttctt tatctacagc ggcttcgagg tgctctttgc ctgcactggt  1080
atcgccttgg gctatggcgt gtgctcggtg gggctggagc ggctggctta cctcctcgtg  1140
gcttacagcc tgggcgcctc agccgcctca ctcctgggcc tgctgggcct gtggctgcca  1200
cgcccggtgc ccctggtggc cggagcaggg gtgcacctgc tgctcacctt catcctcttt  1260
```

-continued

```
ttctgggccc ctgtgcctcg ggtcctgcaa cacagctgga tcctctatgt ggcagctgcc  1320
ctttggggtg tgggcagtgc cctgaacaag actggactca gcacactcct gggaatcttg  1380
tacgaagaca aggagagaca ggacttcatc ttcaccatct accactggtg gcaggctgtg  1440
gccatcttca ccgtgtacct gggctcgagc ctgcacatga aggctaagct ggcggtgctg  1500
ctggtgacgc tggtggcggc cgcggtctcc tacctgcgga tggagcagaa gctgcgccgg  1560
ggcgtggccc cgcgccagcc ccgcatcccg cggccccagc acaaggtgcg cggttaccgc  1620
tacttggagg aggacaactc ggacgagagc gacgcggagg gcgagcatgg ggacggcgcg  1680
gaggaggagg cgccgcccgc agggcccagg cctggccccg agcccgctgg actcggccgc  1740
cggccctgcc cgtacgaaca ggcgcagggg ggagacgggc cggaggagca gtga        1794

SEQ ID NO: 56           moltype = DNA  length = 3153
FEATURE                 Location/Qualifiers
source                  1..3153
                        mol_type = other DNA
                        organism = Mus musculus
SEQUENCE: 56
atggtgtttt cgatgtggac acggaagaga caaattttga tctttttaaa tatgctctta  60
gtttctagag tctttgggtt tcgatggttt cctaaaactc taccttgtga agttaaagta  120
aatatcccag aggcccatgt gatcgtggac tgcacagaca agcatttgac agaaatccct  180
gagggcattc ccactaacac caccaatctt acccttacca tcaaccacat accaagcatc  240
tctccagatt ccttccgtag gctgaaccat ctggaagaaa tcgatttaag atgcaattgt  300
gtacctgttc tactggggtc caaagccaat gtgtgtacca agaggctgca gattagacct  360
ggaagcttta gtggactctc tgacttaaaa gccctttacc tggatggaaa ccaacttctg  420
gagataccac aggatctgcc atccagctta catcttctga gccttgaggc taacaacatc  480
ttctccatca cgaaggagaa tctaacagaa ctggtcaaca ttgaaacact ctacctgggt  540
caaaactgtt attatcgaaa tccttgcaat gtttcctatt ctattgaaaa agatgctttc  600
ctagttatga gaaatttgaa ggttctctca ctaaaagata acaatgtcac agctgtcccc  660
accactttgc cacctaattt actagagctc tatctttata acaatatcat taagaaaatc  720
caagaaaatg attttaataa cctcaatgag ttgcaagttc ttgacctaag tggaaattgc  780
cctcgatgtt ataatgtccc atatccgtgt acaccgtgtg aaaataattc cccccttacag  840
atccatgaca atgctttcaa ttcattgaca gaattaaaag ttttacgttt acacagtaat  900
tctcttcagc atgtgccccc aacatggttt aaaaacatga gaaacctcca ggaactagac  960
ctctcccaaa actacttggc cagagaaatt gaggaggcca aatttttgca ttttcttccc  1020
aaccttgttg agttggattt ttctttcaat tatgagctgc aggtctacca tgcatctata  1080
actttaccac attcactctc ttcattggaa aacttgaaaa ttctgcgtgt caaggggtat  1140
gtctttaaag agctgaaaaa ctccagtctt tctgtattgc acaagcttcc caggctggaa  1200
gttcttgacc ttggcactaa cttcataaaa attgctgacc tcaacatatt caaacatttt  1260
gaaaacctca aactcataga cctttcagtg aataagatat ctccttcaga agagtcaaga  1320
gaagttggct tttgtcctaa tgctcaaact tctgtagacc gtcatgggcc ccaggtcctt  1380
gaggccttac actatttccg atacgatgaa tatgcacgga gctgcaggtt caaaaacaaa  1440
gagccacctt ctttcttgcc tttgaatgca gactgccaca tatatgggca gaccttagac  1500
ttaagtagaa ataacatatt ttttattaaa ccttctgatt ttcagcatct ttcattcctc  1560
aaatgcctca acttatcagg aaacaccatt ggccaaactc ttaatggcag tgaactctgg  1620
ccgttgagag agttgcggta cttagacttc tccaacaacc ggcttgattt actctactca  1680
acagcctttg aagagctcca gagtcttgaa gttctggatc taagtagtaa cagccactat  1740
tttcaagcag aaggaattac tcacatgcta aactttacca agaaattacg gcttctggac  1800
aaactcatga tgaatgataa tgacatctct acttcggcca gcaggaccat ggaaagtgac  1860
tctcttcgaa ttctggagtt cagaggcaac catttagatg ttctatggag agccggtgat  1920
aacagatact tggacttctt caagaatttg ttcaatttag aggtattaga tatctccaga  1980
aattccctga attccttgcc tcctgaggtt tttgagggta tgccgccaaa tctaaagaat  2040
ctctccttgg ccaaaaatgg gctcaaatct ttcttttggg acagactcca gttactgaag  2100
catttggaaa ttttggacct cagccataac cagctgacaa aagtacctga gagattggcc  2160
aactgttcca aaagtctcac aacactgatt cttaagcata atcaaatcag gcaattgaca  2220
aaatattttc tagaagatgc tttgcaattg cgctatctag acatcagttc aaataaaatc  2280
caggtcattc agaagactag cttcccagaa aatgtcctca acaatctgga gatgttggtt  2340
ttacatcaca atcgctttct ttgcaactgt gatgctgtgt ggtttgtctg gtgggttaac  2400
catacagatg ttactattcc atacctggcc actgatgtga cttgtgtagg tccaggagca  2460
cacaaaggtc aaagtgtcat atcccttgat ctgtatacgt gtgagttaga tctcacaaac  2520
ctgattctgt tctcagtttc catatcatca gtcctctttc ttatggtagt tatgacaaca  2580
agtcacctct ttttctggga tatgtggtac atttattatt tttggaaagc aaagataaag  2640
gggtatcagc atctgcaatc catggagtct tgttatgatg cttttattgt gtatgacact  2700
aaaaactcag ctgtgacaga atgggttttg caggagctgg tggcaaaatt ggaagatcca  2760
agagaaaaac acttcaattt gtgtctagaa gaaagagact ggctaccagg acagccagtt  2820
ctagaaaacc tttcccagag catacagctc agcaaaaaga cagtgtttgt gatgacacag  2880
aaatatgcta agactgagag ttttaagatg gcattttatt tgtctcatca gaggctcctg  2940
gatgaaaaag tggatgtgat tatcttgata ttcttggaaa agcctcttca gaagtctaag  3000
tttcttcagc tcaggaagag actctgcagg agctctgtcc ttgagtggcc tgcaaatcca  3060
caggctcacc catacttctg gcagtgcctg aaaaatgccc tgaccacaga caatcatgtg  3120
gcttatagtc aaatgttcaa ggaaacagtc tag                                3153

SEQ ID NO: 57           moltype = DNA  length = 3153
FEATURE                 Location/Qualifiers
source                  1..3153
                        mol_type = other DNA
                        organism = Rattus norvegicus
SEQUENCE: 57
atggtatttc caatgtggac attgaagaga caaagtttta tctttttaaa tatgatctta  60
gtttctagag tccttgggtt tcgatggtat cctaaaactc taccttgtga tgtctctctc  120
gatagcacaa acacccatgt gattgtggat tgcacagaca agcatttgac agaaatacct  180
```

```
gagggtattc ccactaatac caccaacctt acccttacca tcaaccacat accaagcatc  240
tctccagact ccttccatag gctgaagcat ctggaggagc ttgatttaag atgcaactgt  300
gtacctattc tactggggtc caaagccaat gtgtgcacca agaggctaca gattagacct  360
ggaagcttta gtggactctc tgacttaaaa tccctttacc tggatggaaa tcaacttcta  420
gagataccac aggatcttcc atcaagctta cagcttctga gccttgaggc taacaatatc  480
ttctccatca caaaggagaa tctatcagaa ctagtcaaca ttgaatcact ctacctgggc  540
caaaactgtt attatcgaaa tccttgcaat gtttcctatt ctattgaaaa agatgctttc  600
ctagttatga aaaatttaaa ggttctctca ctaaaagata acaatgtcac agctgtcccc  660
accattttgc cacctaattt gctagaactc tatctttata acaacatcat taagagaatc  720
caagaacatg attttaataa gctcagccag ttgcaagttc ttgacctaag tggaaactgc  780
cctcgatgtt ataatgtccc atatccatgt acaccatgtg aaaataattc tcccttacag  840
atccatgaca atgcttttga ttcattaaca gaattaaaag ttttacgtct acacagtaac  900
tctcttcagc atgtgcctgc agaatggttt aaaaacatga gcaacctcca ggaactagac  960
ctctcccaaa actacttagc cagagaaatt gaagaagcca aatttttgaa ttctctcccc  1020
aaccttgtcc agttggatct gtctttcaat tatgagctgc aggtctacca tgcatctatt  1080
actttaccac actcactctc ttcattgaca aagttgaaaa atctgtatat caagggatat  1140
gtctttaaag agctgaaaga ctccagcctt tctgtattgc acaacctttc caatctagaa  1200
gttcttgacc ttggcactaa cttcataaaa attgctgacc tcaacatatt ccaacagttt  1260
gaaaacctca aattcataga cctttcagtg aataagatat ccccctcaga agagtcaaga  1320
gaagttggtt tatgtcctaa tgcccaaact tctgtagact ggcacggacc ccaggtcctt  1380
gaggccttac actatttccg atatgatgaa tatgcacgga gctgcaggtt caaaaacaaa  1440
gagccgccta ctttttgcc tttgaatgca gactgccaca catatgggaa gaccttagac  1500
ctaagtagaa ataacatatt ttttattaaa ccctctgatt ttaagcatct ttcattcctg  1560
aaatgcctca atttgtcagg aaacgccatt ggccaaactc ttaatggcag tgaactccag  1620
cccttgagag agctgcggta cttagacttc tccaacaacc ggcttgattt actctactca  1680
acagcctttg aagagctcca gaatctggaa attctggatc taagtagtaa cagccactat  1740
tttcaagcag aaggaattac tcacatgcta aactttacca agaaattacg gcatctagag  1800
aaactcatga tgaatgacaa tgacatctct acttcagcca gcaggaccat ggaaagtgaa  1860
tctcttcgtg ttctggaatt cagaggcaac catttagatg ttctatggag agatggtgat  1920
aacagatact tggacttctt caagaatctg ctcaacttag aggaattaga tatctccaga  1980
aattccctga attccgtgcc tcctggagtt tttgagggta tgccaccgaa tctaacgact  2040
ctctccttag ccaaaaatgg actcagatct ttctcttggg gtagacttca gttactaaag  2100
catttgaaaa atttggacct cagccacaac cagctgacaa ctgtccctgc gagattggcc  2160
aactgttcca aaagtctcac aaaactgatt cttaatcata atcaaatcag gcagttgaca  2220
aaatattttc tagaagatgc tttgcaattg cgctatctag acatcagttc aaataagatc  2280
caggtcattc agaagactag cttcccagaa aacgtcctca acaatctgaa catgttgctt  2340
ttacatcaca atcgctttct ttgcaactgt gatgctgtgt ggtttgtctg gtgggttaat  2400
catacagatg ttactattcc atacctggcc actgatgtga cttgtgcagg tccaggcgca  2460
cacaaaggtc aaagtgtcat atctctggat ctatatacat gtgaattaga tctcacaaac  2520
ctgattctgt tctcagtttc catatcatca gtcctctttc ttatgatagt tatgacaaca  2580
agtcacctct ttttctggga tatgtggtac atttattatt tctggaaagc caagataaag  2640
ggttatcaac atctgcaatc aatggagtct tgttatgatg cttttattgt gtatgacact  2700
aaaaactcag ctgtgacaga atgggttttg caggagctgg tggttaaatt ggaagaccca  2760
agagaaaaac actttaattt gtgtctagaa gaaagagact ggctaccagg gcagccagtt  2820
ctagaaaacc tttcccagag catacagctc agcagaaaga cagtgtttgt gatgacacag  2880
aaatatgcga agactgagag ttttaagatg gcgttttatt tgtcccatca gaggcttatg  2940
gatgaaaagg tggatgtgat tatcttgata ttcttggaaa agcctcttca gaagtctaag  3000
tttcttcagc tccggaagag gctctgcagc agttctgtcc ttgagtggcc tacaaatcca  3060
caagctcacc catatttctg gcagtgcctg aaaaatgccc tgactacaga caatcatgtg  3120
gcttatagtc aaatgttcaa ggaaacagtc tag                              3153
```

```
SEQ ID NO: 58          moltype = DNA  length = 3150
FEATURE                Location/Qualifiers
source                 1..3150
                       mol_type = other DNA
                       organism = Macaca mulatta
SEQUENCE: 58
atgatgttcc ctgtgtggac cctgaagcgg cagatcctga ttctgttcaa tattatcctg  60
atttctaaac tgctgggggc aaggtggttc cccaagactc tgccttgcga cgtgaccctg  120
gatgtcagca agaaccacgt gatcgtcgac tgtacagata aacatctgac tgagattcca  180
ggcggcatcc ccaccaacac cacaaatctg accctgacaa tcaatcacat tcctgacatc  240
tctccagcca gttttcaccg gctggtgcat ctggtcgaga ttgatttccg atgcaactgt  300
gtgcctatcc ggctgggaag caagtccaat atgtgccctc ggagactgca gatcaagcca  360
agatctttta gtggcctgac ctacctgaag agcctgtatc tggacggaaa ccagctgctg  420
gagatcccac agggactgcc accttccctg cagctgctgt ctctggaagc caacaatatt  480
ttctccatca ggaaggagaa cctgacagaa ctggctaata tcgagattct gtacctgggc  540
cagaactgct actatcgcaa tccctgttac gtgtcatata gcatcgaaaa agacgccttt  600
ctgaacctga ctaagctgaa agtcctgtct ctgaaggata acaatgtgac taccgtcccc  660
accgtgctgc ctagtactct gaccgagctg tacctgtata acaatatgat tgcagagatc  720
caggaagacg atttcaacaa tctgaaccag ctgcagattc tggacctgag tggaaactgc  780
cccaggtgtt acaatgctcc ctttccttgc acaccttgta agaacaattc tccactgcag  840
atccccgtca atgcattcga tgccctgact gagctgaaag tgctgcggct gcactccaac  900
tctctgcagc atgtcccacc cagatggttt aagaatatca acaatctgca ggagctggac  960
ctgagccaga acttcctggc caaggaaatt ggcgatgcta aattcctgca ctttctgcca  1020
aacctgatcc agctggacct gagcttcaat tttgagctgc aggtgtaccg ggcatctatg  1080
aacctgagtc aggcctttag ctccctgaaa agcctgaaga ttctgcggat cagaggctat  1140
gtgtttaaag agctgaagtc attcaatctg agccccctgc ataacctgca gaatctggaa  1200
gtgctggatc tgggaaccaa cttcatcaaa attgccaatc tgagcatgtt caaacagttt  1260
aagagactga aagtgattga cctgtccgtc aacaagatca gtccctcagg cgattctagt  1320
```

```
gaagtggggt tttgcagcaa tgctcgaaca tcagtcgaga gctacgaacc tcaggtgctg  1380
gaacagctgt actatttcag atacgacaaa tatgccagat catgcaggtt taagaacaaa  1440
gaggcttcct tcacatctgt gaatgaaagc tgttacaagt atgggcagac tctggacctg  1500
agtaagaact caattttctt tatcaaatca agcgatttcc agcacctgtc ctttctgaag  1560
tgtctgaacc tgagtgggaa tctgatctca cagactctga atggatctga gtttcagcct  1620
ctggctgaac tgagatacct ggacttctca aacaataggc tggatctgct gcatagcacc  1680
gcattcgagg aactgaggaa actggaggtg ctggacattt cctctaacag ccactatttt  1740
cagtccgaag gaatcacaca tatgctgaac ttcactaaga atctgaaagt gctgcagaag  1800
ctgatgatga acgacaatga catcagcagc agcacatccc gcactatgga gagcgaatcc  1860
ctgcgcaccc tggagtttcg aggcaaccac ctggatgtgc tgtggcggga cggggataac  1920
agatacctgc agctgttcaa gaatctgctg aaactggagg aactggacat ttccaaaaac  1980
tctctgagtt ttctgccctc tggggtgttc gatggaatgc ctccaaacct gaagaatctg  2040
tctctggcca agaatggcct gaaaagtttt atctgggaga agctgaggta tctgaaaaac  2100
ctggaaacac tggacctgag tcacaatcag ctgacaactg tgcctgagag gctgtcaaac  2160
tgctcacgca gcctgaagaa tctgattctg aaaaacaatc agatcaggtc tctgactaaa  2220
tacttcctgc aggacgcctt tcagctgcgc tatctggatc tgtcctctaa taagattcag  2280
atgatccaga aaaccagctt ccctgagaac gtgctgaaca atctgaagat gctgctgctg  2340
caccataatc gctttctgtg cacatgtgac gccgtctggt tcgtgtggtg ggtcaaccac  2400
accgaggtga caattccata cctggcaact gatgtgacct gcgtcggacc aggagcacat  2460
aagggacaga gcgtgatctc cctggacctg tatacctgtg aactggatct gacaaatctg  2520
attctgtttt ccctgtctat cagtgtctca ctgttcctga tggtcatgat gaccgcaagc  2580
cacctgtact tttgggatgt gtggtacatc taccatttct gcaaggccaa aattaagggc  2640
tatcagcggc tgatctcccc tgactgctgt tacgatgctt ttatcgtgta tgacactaag  2700
gaccccgcag tgaccgagtg ggtcctggct gaactggtcg caaagctgga ggacccacgc  2760
gaaaaacact tcaacctgtg tctggaggaa cgagattggc tgccagggca gcccgtgctg  2820
gagaatctga gccagtccat ccagctgtcc aagaaaaccg tgttcgtcat gacagacaag  2880
tacgctaaga ccgaaaactt caagatcgca ttctatctgt ctcatcagag actgatggac  2940
gagaaagtgg atgtcatcat tctgatcttc ctggaaaagc catttcagaa aagcaagttc  3000
ctgcagctgc gaaagcggct gtgcggcagt tcagtgctgg agtggcctac aaacccacag  3060
gcccacccct actttggca gtgtctgaaa aacgccctgg ctaccgataa tcatgtggct  3120
tatagccagg tcttcaagga aacagtgtag                                    3150

SEQ ID NO: 59          moltype = DNA  length = 449
FEATURE                Location/Qualifiers
source                 1..449
                       mol_type = other DNA
                       organism = Homo sapiens
SEQUENCE: 59
gcctccggac tctagagcca ccatggtgct gcagacccag gtgttcatct ccctgctgct  60
gtggatctcc ggcgcgtacg gcgatatcgt gatgattaaa cgtacggtgg ccgccccctc  120
cgtgttcatc ttcccccct ccgacgagca gctgaagtcc ggcaccgcct ccgtggtgtg  180
cctgctgaat aacttctacc ccagagaggc caaggtgcag tggaaggtgg acaacgccct  240
gcagtccggg aactcccagg agagcgtgac cgagcaggac agcaaggaca gcacctacag  300
cctgagcagc accctgaccc tgagcaaagc cgactacgag aagcacaagg tgtacgcctg  360
cgaggtgacc caccagggcc tgagctcccc cgtcaccaag agcttcaaca gggggagtg  420
ttaggggccc gtttaaacgg gggaggcta                                    449

SEQ ID NO: 60          moltype = DNA  length = 1132
FEATURE                Location/Qualifiers
source                 1..1132
                       mol_type = other DNA
                       organism = Homo sapiens
SEQUENCE: 60
gcctccggac tctagagcca ccatgaaaca cctgtggttc ttcctcctgc tggtggcagc  60
tcccagatgg gtgctgagcc aggtgcaatt gtgcaggcgg ttagctcagc ctccaccaag  120
ggcccaagcg tcttcccct ggcaccctcc tccaagagca cctctggcgg cacagccgcc  180
ctgggctgcc tggtcaagga ctacttcccc gaacccgtga ccgtgagctg gaactcaggc  240
gccctgacca gcggcgtgca caccttcccc gctgtcctgc agtcctcagg actctactcc  300
ctcagcagcg tggtgaccgt gccctccagc agcttgggca cccagaccta catctgcaac  360
gtgaatcaca agcccagcaa caccaaggtg gacaagagag ttgagcccaa atcttgtgac  420
aaaactcaca catgcccacc ctgcccagca cctgaactcc tggggggacc ctcagtcttc  480
ctcttccccc caaaacccaa ggacaccctc atgatctccc ggacccctga ggtcacatgc  540
gtggtggtgg acgtgagcca cgaagaccct gaggtcaagt tcaactggta cgtggacggc  600
gtggaggtgc ataatgccaa gacaaagccc cgggaggagc agtacaacag cacgtaccgg  660
gtggtcagcg tcctcaccgt cctgcaccag gactggctga atggcaagga gtacaagtgc  720
aaggtctcca acaaagccct cccagccccc atcgagaaaa ccatctccaa agccaaaggc  780
cagccccggg aaccacaggt gtacaccctg cccccatccc gggaggagat gaccaagaac  840
caggtcagcc tgacctgcct ggtcaaaggc ttctatccca gcgacatcgc cgtggagtgg  900
gagagcaatg gccagcccga gaacaactac aagaccaccc ctcccgtgct ggactccgac  960
ggctccttct tcctctacag caagctcacc gtggacaaga gcaggtggca gcagggcaac  1020
gtcttctcat gctccgtgat gcatgaggct ctgcacaacc actacaccca gaagagcctc  1080
tccctgtctc ccggcaaatg agatatcggg cccgtttaaa cgggggaggc ta          1132

SEQ ID NO: 61          moltype = DNA  length = 1395
FEATURE                Location/Qualifiers
misc_feature           1..1395
                       note = Synthetic
misc_feature           1..1395
                       note = Nucleotid sequence encoding heavy chain of cAT01
```

```
                         antibody
source                  1..1395
                        mol_type = other DNA
                        organism = synthetic construct
SEQUENCE: 61
atgaaacacc tgtggttctt cctcctgctg gtggcagctc ccagatgggt gctgagccag  60
gtgcagctgc agcagcctgg cgccgaactc gtgaaacctg gcgcctccgt gaacctgagc  120
tgcaaggcca gcggctacac cttcaccaac aactggctgc actgggtcaa gcagaggccc  180
ggcagaggcc tggaatggat cggcgacatc taccccagca acggccggac caactacaac  240
gagcagttca agaccaaggc caccctgacc gtggacaaga gcagcagcac cgcctacatg  300
cagctgtcca gcctgaccag cgaggacagc gccgtgtact tctgcgccag agagcggggc  360
tacttcgact attggggcca gggaaccgct ctgaccgtca gctcagcctc caccaagggc  420
ccaagcgtct tcccccctggc accctcctcc aagagcacct ctggcggcac agccgccctg  480
ggctgcctgg tcaaggacta cttccccgaa cccgtgaccg tgagctggaa ctcaggcgcc  540
ctgaccagcg gcgtgcacac cttccccgct gtcctgcagt cctcaggact ctactccctc  600
agcagcgtgg tgaccgtgcc ctccagcagc ttgggcaccc agacctacat ctgcaacgtg  660
aatcacaagc ccagcaacac caaggtggac aagagagttg agcccaaatc ttgtgacaaa  720
actcacacat gcccaccctg cccagcacct gaactcctgg ggggaccctc agtcttcctc  780
ttccccccaa aacccaagga caccctcatg atctcccgga cccctgaggt cacatgcgtg  840
gtggtggacg tgagccacga agaccctgag gtcaagttca actggtacgt ggacggcgtg  900
gaggtgcata atgccaagac aaagccccgg gaggagcagt acaacagcac gtaccgggtg  960
gtcagcgtcc tcaccgtcct gcaccaggac tggctgaatg gcaaggagta caagtgcaag  1020
gtctccaaca aagccctccc agcccccatc gagaaaacca tctccaaagc caaaggccag  1080
ccccgggaac cacaggtgta caccctgccc ccatcccggg aggagatgac caagaaccag  1140
gtcagcctga cctgcctggt caaaggcttc tatcccagcg acatcgccgt ggagtgggag  1200
agcaatggcc agcccgagaa caactacaag accacccctc ccgtgctgga ctccgacggc  1260
tccttcttcc tctacagcaa gctcaccgtg gacaagagca ggtggcagca gggcaacgtc  1320
ttctcatgct ccgtgatgca tgaggctctg cacaaccact acacccagaa gagcctctcc  1380
ctgtctcccg gcaaa                                                  1395

SEQ ID NO: 62           moltype = DNA  length = 749
FEATURE                 Location/Qualifiers
misc_feature            1..749
                        note = Synthetic
misc_feature            1..749
                        note = Nucleotid sequence of DNA fragment containing a
                         nucleotide sequence encoding light chain of cAT01 antibody
source                  1..749
                        mol_type = other DNA
                        organism = synthetic construct
SEQUENCE: 62
ccagcctccg gactctagag ccaccatggt gctgcagacc caggtgttca tcagcctgct  60
gctgtggatc agcggcgcct acggcgacat ccagatgacc cagagcccta gcagcctgag  120
cacaagcctg ggcggcaaag tgaccatcac atgcaaggcc agccaggaca tcaacaagta  180
tatcgcctgg tatcagcaca aacccggcaa gggccccaga ctgctgattc actacaccag  240
caccctgcag cccggcatcc ccagcagatt ttctggcagc ggctccggca gagactacag  300
cttcagcatc agcaacctgg aacccgagga tatcgccacc tactactgcc tgcagtacga  360
ctacctgctg accttcggag ccggcaccaa gctggaactg aagagagccg tggccgctcc  420
ctccgtgttc atcttcccac ctagcgacga gcagctgaag tccggcacag cctctgtcgt  480
gtgcctgctg aacaacttct acccccgcga ggccaaggtg cagtggaagg tggacaatgc  540
cctgcagagc ggcaacagcc aggaaagcgt gaccgagcag gacagcaagg actccaccta  600
cagcctgtcc tccaccctga ccctgagcaa ggccgactac gagaagcaca aggtgtacgc  660
ctgcgaagtg acccaccagg gcctgagcag ccctgtgacc aagagcttca accggggcga  720
gtgctgagtt taaacggggg aggctaact                                  749

SEQ ID NO: 63           moltype = DNA  length = 1413
FEATURE                 Location/Qualifiers
misc_feature            1..1413
                        note = Synthetic
misc_feature            1..1413
                        note = Nucleotid sequence encoding heavy chain of cNB7
                         antibody
source                  1..1413
                        mol_type = other DNA
                        organism = synthetic construct
SEQUENCE: 63
atgaaacacc tgtggttctt cctcctgctg gtggcagctc ccagatgggt gctgagcgac  60
gtgcagctgc aggaatctgg ccctggcctc gtgaagccta gccagagcct gagcctgaca  120
tgcaccgtga ccggctacag catcaccagc gactacgcct ggaactggat ccggcagttc  180
cccggcaaca agctggaatg gatgggccac atcagctacc ggggcaacac caactacaac  240
cccagcctga agtcccggat ctccatcacc cgggacacca gcaagaacca gttctttctg  300
cagctgaaca gcgtgaccac cgaggacacc gccacctact actgcgccag ctggaactac  360
tacggctacg tggactatgc catggactac tggggccagg gcacctccgt gaccgtcagc  420
tcagcctcca ccaagggccc aagcgtcttc cccctggcac cctcctccaa gagcacctct  480
ggcggcacag ccgccctggg ctgcctggtc aaggactact tccccgaacc cgtgaccgtg  540
agctggaact caggcgccct gaccagcggc gtgcacacct tccccgctgt cctgcagtcc  600
tcaggactct actccctcag cagcgtggtg accgtgccct ccagcagctt gggcacccag  660
acctacatct gcaacgtgaa tcacaagccc agcaacacca aggtggacaa gagagttgag  720
cccaaatctt gtgacaaaac tcacacatgc ccaccctgcc cagcacctga actcctgggg  780
```

-continued

```
ggaccctcag tcttcctctt ccccccaaaa cccaaggaca ccctcatgat ctcccggacc  840
cctgaggtca catgcgtggt ggtggacgtg agccacgaag accctgaggt caagttcaac  900
tggtacgtgg acggcgtgga ggtgcataat gccaagacaa agccccggga ggagcagtac  960
aacagcacgt accgggtggt cagcgtcctc accgtcctgc accaggactg gctgaatggc  1020
aaggagtaca agtgcaaggt ctccaacaaa gccctcccag cccccatcga gaaaaccatc  1080
tccaaagcca aaggccagcc ccgggaacca caggtgtaca ccctgccccc atcccgggag  1140
gagatgacca agaaccaggt cagcctgacc tgcctggtca aaggcttcta tcccagcgac  1200
atcgccgtgg agtgggagag caatggccag cccgagaaca actacaagac cacccctccc  1260
gtgctggact ccgacggctc cttcttcctc tacagcaagc tcaccgtgga caagagcagg  1320
tggcagcagg gcaacgtctt ctcatgctcc gtgatgcatg aggctctgca caaccactac  1380
acccagaaga gcctctccct gtctcccggc aaa                              1413
```

```
SEQ ID NO: 64          moltype = DNA  length = 749
FEATURE                Location/Qualifiers
misc_feature           1..749
                       note = Synthetic
misc_feature           1..749
                       note = Nucleotid sequence of DNA fragment containing a
                        nucleotide sequence encoding light chain of cNB7 antibody
source                 1..749
                       mol_type = other DNA
                       organism = synthetic construct
SEQUENCE: 64
ccagcctccg gactctagag ccaccatggt gctgcagacc caggtgttca tcagcctgct  60
gctgtggatc agcggcgcct acggcgacat ccagatgacc cagacaccca gcagcctgag  120
cgccagcctg ggcgatagag tgaccatcag ctgcagagcc agccaggaca tcagcaacta  180
cctgaactgg tatcagcaga aacccgacgg caccgtgaag ctgctgatct actacaccag  240
cagactgcac agcggcgtgc ccagcagatt tctggcagc ggctccggca ccgactacag  300
cctgaccatc aacaacctgg aacaggaaga tatcgctacc tacttctgtc agcaaggcga  360
caccttcccc accttcggcg gaggcaccaa gctggaaatc aagagagccg tggccgctcc  420
ctccgtgttc atcttcccac ctagcgacga gcagctgaag tctggcacag ccagcgtcgt  480
gtgcctgctg aacaacttct acccccgcga ggccaaggtg cagtggaagg tggacaatgc  540
cctgcagagc ggcaacagcc aggaaagcgt gaccgagcag gacagcaagg actccaccta  600
ctccctgagc agcaccctga ccctgagcaa ggccgactac gagaagcaca aggtgtacgc  660
ctgcgaagtg acccaccagg gcctgtctag ccccgtgacc aagagcttca accggggcga  720
gtgttgagtt taaacggggg aggctaact                                  749
```

```
SEQ ID NO: 65          moltype = DNA  length = 1410
FEATURE                Location/Qualifiers
misc_feature           1..1410
                       note = Synthetic
misc_feature           1..1410
                       note = Nucleotid sequence encoding heavy chain of cFAN2
                        antibody
source                 1..1410
                       mol_type = other DNA
                       organism = synthetic construct
SEQUENCE: 65
atgaaacacc tgtggttctt cctcctgctg gtggcagctc ccagatgggt gctgagccag  60
gtgcagctga aagagtctgg ccctggactg gtggccccta gccagagcct gagcatcacc  120
tgtaccgtgt ccggcttcag cctgaccggc tacggcgtga actgggtgcg ccagcctcct  180
ggcaaaggcc tggaatggct gggcatgatc tggggcgacg gcagcaccga ctacaacagc  240
gccctgaagt cccggctgag catccggaag gacaacagca agtcccaggt gttcctgaag  300
atgaacagcc tgcagaccga cgacaccgcc cggtactact gcgccagaga caagggctac  360
gacggctact actacgccat ggactactgg ggccagggca cctctgtgac cgtcagctca  420
gcctccacca agggcccaag cgtcttcccc ctggcaccct cctccaagag cacctctggc  480
ggcacagccg ccctgggctg cctggtcaag gactacttcc ccgaacccgt gaccgtgagc  540
tggaactcag gcgccctgac cagcggcgtg cacaccttcc ccgctgtcct gcagtcctca  600
ggactctact ccctcagcag cgtggtgacc gtgccctcca gcagcttggg cacccagacc  660
tacatctgca acgtgaatca caagcccagc aacaccaagg tggacaagag agttgagccc  720
aaatcttgtg acaaaactca cacatgccca ccctgcccag cacctgaact cctgggggga  780
ccctcagtct tcctcttccc cccaaaaccc aaggacaccc tcatgatctc ccggacccct  840
gaggtcacat gcgtggtggt ggacgtgagc cacgaagacc ctgaggtcaa gttcaactgg  900
tacgtggacg gcgtggaggt gcataatgcc aagacaaagc cccgggagga gcagtacaac  960
agcacgtacc gggtggtcag cgtcctcacc gtcctgcacc aggactggct gaatggcaag  1020
gagtacaagt gcaaggtctc caacaaagcc ctcccagccc ccatcgagaa aaccatctcc  1080
aaagccaaag gccagccccg ggaaccacag gtgtacaccc tgcccccatc ccgggaggag  1140
atgaccaaga accaggtcag cctgacctgc ctggtcaaag gcttctatcc cagcgacatc  1200
gccgtggagt gggagagcaa tggccagccc gagaacaact acaagaccac ccctcccgtg  1260
ctggactccg acggctcctt cttcctctac agcaagctca ccgtggacaa gagcaggtgg  1320
cagcagggca acgtcttctc atgctccgtg atgcatgagg ctctgcacaa ccactacacc  1380
cagaagagcc tctccctgtc tcccggcaaa                                  1410
```

```
SEQ ID NO: 66          moltype = DNA  length = 752
FEATURE                Location/Qualifiers
misc_feature           1..752
                       note = Synthetic
misc_feature           1..752
                       note = Nucleotid sequence of DNA fragment containing a
```

```
                        nucleotide sequence encoding light chain of cFAN2 antibody
source                  1..752
                        mol_type = other DNA
                        organism = synthetic construct
SEQUENCE: 66
ccagcctccg gactctagag ccaccatggt gctgcagacc caggtgttca tcagcctgct  60
gctgtggatc agcggcgcct acggcgacat ccagatgaca cagtctcccg ccagcctgag  120
cgcctctgtg ggagagacag tgaccatcac ctgtcgggcc agcgagaaca tctacagcta  180
cctggcctgg tatcagcaga agcagggcaa gagcccccag ctgctggtgt acgatgccaa  240
gacactggcc gagggcgtgc ccagcagatt ttctggcagc ggctccggca cccagttcag  300
cctgaagatc aacagcctgc agcccgagga cttcggcagc tactactgcc agcaccacta  360
cggcatccct tacaccttcg gcggaggcac caagctggaa atcaagagag ccgtggccgc  420
tccctccgtg ttcatcttcc cacctagcga cgagcagctg aagtccggca cagctagcgt  480
cgtgtgcctg ctgaacaact tctacccccg cgaggccaag gtgcagtgga aggtggacaa  540
tgccctgcag agcggcaaca gccaggaaag cgtgaccgag caggacagca aggactccac  600
ctacagcctg tccagcaccc tgaccctgag caaggccgac tacgagaagc acaaggtgta  660
cgcctgcgaa gtgacccacc agggcctgag cagcccagtg accaagagct tcaaccgggg  720
cgagtgctga gtttaaacgg gggaggctaa ct                                752

SEQ ID NO: 67           moltype = DNA  length = 1395
FEATURE                 Location/Qualifiers
misc_feature            1..1395
                        note = Synthetic
misc_feature            1..1395
                        note = Nucleotid sequence encoding huAT01_H1_IgG1LALA
source                  1..1395
                        mol_type = other DNA
                        organism = synthetic construct
SEQUENCE: 67
atgaaacacc tgtggttctt cctcctgctg gtggcagctc ccagatgggt gctgagccag  60
gtgcagctgg tgcagtctgg cgccgaagtg aagaaaccag gcgccagcgt gaaggtgtcc  120
tgcaaggcca gcggctacac ctttaccaac aactggctgc actgggtgcg ccaggctcca  180
ggacagggac tggaatggat gggcgacatc taccccagca acggccggac caactacgcc  240
cagaaattcc agggcagagt gaccatcacc gccgacaaga gcaccagcac cgcctacatg  300
gaactgagca gcctgcggag cgaggacacc gccgtgtact actgcgccag agagcggggc  360
tacttcgact attggggcca gggcacactc gtgaccgtca gctcagcctc caccaagggc  420
ccaagcgtct tccccctggc accctcctcc aagagcacct ctggcggcac agccgccctg  480
ggctgcctgg tcaaggacta cttccccgaa cccgtgaccg tgagctggaa ctcaggcgcc  540
ctgaccagcg gcgtgcacac cttccccgct gtcctgcagt cctcaggact ctactccctc  600
agcagcgtgg tgaccgtgcc ctccagcagc ttgggcaccc agacctacat ctgcaacgtg  660
aatcacaagc ccagcaacac caaggtggac aagagagttg agcccaaatc ttgtgacaaa  720
actcacacat gcccaccctg cccagcacct gaagccgcgg ggggaccctc agtcttcctc  780
ttccccccaa aacccaagga caccctcatg atctcccgga cccctgaggt cacatgcgtg  840
gtggtggacg tgagccacga agaccctgag gtcaagttca actggtacgt ggacggcgtg  900
gaggtgcata atgccaagac aaagccccgg gaggagcagt acaacagcac gtaccgggtg  960
gtcagcgtcc tcaccgtcct gcaccaggac tggctgaatg gcaaggagta caagtgcaag  1020
gtctccaaca aagccctccc agcccccatc gagaaaacca tctccaaagc caaaggccag  1080
ccccgggaac cacaggtgta caccctgccc ccatcccggg aggagatgac caagaaccag  1140
gtcagcctga cctgcctggt caaaggcttc tatcccagcg acatcgccgt ggagtgggag  1200
agcaatggcc agcccgagaa caactacaag accacccctc ccgtgctgga ctccgacggc  1260
tccttcttcc tctacagcaa gctcaccgtg gacaagagca ggtggcagca gggcaacgtc  1320
ttctcatgct ccgtgatgca tgaggctctg cacaaccact acacccagaa gagcctctcc  1380
ctgtctcccg gcaaa                                                   1395

SEQ ID NO: 68           moltype = DNA  length = 1395
FEATURE                 Location/Qualifiers
misc_feature            1..1395
                        note = Synthetic
misc_feature            1..1395
                        note = Nucleotid sequence encoding huAT01_H3_IgG1LALA
source                  1..1395
                        mol_type = other DNA
                        organism = synthetic construct
SEQUENCE: 68
atgaaacacc tgtggttctt cctcctgctg gtggcagctc ccagatgggt gctgagccag  60
gtgcagctgg tgcagtctgg cgccgaagtg aagaaaccag gcgccagcgt gaaggtgtcc  120
tgcaaggcca gcggctacac ctttaccaac aactggctgc actgggtgcg ccaggctcca  180
ggacagggac tggaatggat gggcgacatc taccccagca acggccggac caactacgcc  240
cagaaattcc agggcagagt gaccctgacc gtggacaaga gcaccagcac cgcctacatg  300
gaactgagca gcctgcggag cgaggatacc gccgtgtact tctgtgccag agagcggggc  360
tacttcgact actggggcca gggaacactc gtgaccgtca gctcagcctc caccaagggc  420
ccaagcgtct tccccctggc accctcctcc aagagcacct ctggcggcac agccgccctg  480
ggctgcctgg tcaaggacta cttccccgaa cccgtgaccg tgagctggaa ctcaggcgcc  540
ctgaccagcg gcgtgcacac cttccccgct gtcctgcagt cctcaggact ctactccctc  600
agcagcgtgg tgaccgtgcc ctccagcagc ttgggcaccc agacctacat ctgcaacgtg  660
aatcacaagc ccagcaacac caaggtggac aagagagttg agcccaaatc ttgtgacaaa  720
actcacacat gcccaccctg cccagcacct gaagccgcgg ggggaccctc agtcttcctc  780
ttccccccaa aacccaagga caccctcatg atctcccgga cccctgaggt cacatgcgtg  840
gtggtggacg tgagccacga agaccctgag gtcaagttca actggtacgt ggacggcgtg  900
```

```
gaggtgcata atgccaagac aaagccccgg gaggagcagt acaacagcac gtaccgggtg  960
gtcagcgtcc tcaccgtcct gcaccaggac tggctgaatg gcaaggagta caagtgcaag  1020
gtctccaaca aagccctccc agcccccatc gagaaaacca tctccaaagc caaaggccag  1080
ccccgggaac cacaggtgta caccctgccc ccatcccggg aggagatgac caagaaccag  1140
gtcagcctga cctgcctggt caaaggcttc tatcccagcg acatcgccgt ggagtgggag  1200
agcaatggcc agcccgagaa caactacaag accacccctc ccgtgctgga ctccgacggc  1260
tccttcttcc tctacagcaa gctcaccgtg gacaagagca ggtggcagca gggcaacgtc  1320
ttctcatgct ccgtgatgca tgaggctctg cacaaccact acacccagaa gagcctctcc  1380
ctgtctcccg gcaaa                                                   1395

SEQ ID NO: 69          moltype = DNA  length = 1386
FEATURE                Location/Qualifiers
misc_feature           1..1386
                       note = Synthetic
misc_feature           1..1386
                       note = Nucleotid sequence encoding huAT01_H3_IgG4Pro
source                 1..1386
                       mol_type = other DNA
                       organism = synthetic construct
SEQUENCE: 69
atgaaacacc tgtggttctt cctcctgctg gtggcagctc ccagatgggt gctgagccag  60
gtgcagctgg tgcagtctgg cgccgaagtg aagaaaccag gcgccagcgt gaaggtgtcc  120
tgcaaggcca gcggctacac ctttaccaac aactggctgc actgggtgcg ccaggctcca  180
ggacagggac tggaatggat gggcgacatc taccccagca acggccggac caactacgcc  240
cagaaattcc agggcagagt gaccctgacc gtggacaaga gcaccagcac cgcctacatg  300
gaactgagca gcctgcggag cgaggatacc gccgtgtact tctgtgccag agagcggggc  360
tacttcgact actggggcca gggaacactc gtgaccgtca gctcagcctc caccaagggc  420
cctagcgtgt tccctctggc cccttgtagc agaagcacca gcgagtctac agccgccctg  480
ggctgcctcg tgaaggacta ctttcccgag cccgtgaccg tgtcctggaa ctctggcgct  540
ctgacaagcg gcgtgcacac ctttccagcc gtgctgcaga gcagcggcct gtactctctg  600
tccagcgtcg tgactgtgcc cagcagctct ctgggcacca agacctacac ctgtaacgtg  660
gaccacaagc ccagcaacac caaggtggac aagcgggtgg aatctaagta cggccctccc  720
tgccctcctt gcccagcccc tgaatttctg ggcggaccct ccgtgttcct gttcccccca  780
aagcccaagg acaccctgat gatcagccgg acccccgaag tgacctgcgt ggtggtggat  840
gtgtcccagg aagatcccga ggtgcagttc aattggtacg tggacggcgt ggaagtgcac  900
aacgccaaga ccaagcctag agaggaacag ttcaacagca cctaccgggt ggtgtccgtg  960
ctgacagtgc tgcaccagga ctggctgaac ggcaaagagt acaagtgcaa ggtgtccaac  1020
aagggcctgc ccagctccat cgagaaaacc atcagcaagg ccaagggcca gccccgcgaa  1080
ccccaggtgt acacactgcc tccaagccag gaagagatga ccaagaatca ggtgtccctg  1140
acctgtctcg tgaaaggctt ctaccccctcc gatatcgccg tggaatggga gagcaacggc  1200
cagcccgaga acaactacaa gaccaccccc cctgtgctgg actccgatgg ctcattcttc  1260
ctgtacagca gactgaccgt ggacaagagc cggtggcagg aaggcaacgt gttcagctgc  1320
tccgtgatgc acgaggccct gcacaaccac tacacccaga agtccctgtc tctgagcctg  1380
ggcaaa                                                             1386

SEQ ID NO: 70          moltype = DNA  length = 699
FEATURE                Location/Qualifiers
misc_feature           1..699
                       note = Synthetic
misc_feature           1..699
                       note = Nucleotid sequence encoding huAT01_L1
source                 1..699
                       mol_type = other DNA
                       organism = synthetic construct
SEQUENCE: 70
atggtgctgc agacccaggt gttcatctcc ctgctgctgt ggatctccgg cgcgtacggc  60
gacatccaga tgacccagag ccctagcagc ctgagcgcca gcgtgggcga cagagtgacc  120
atcacatgca aggccagcca ggacatcaac aagtatatcg cctggtatca gcagaagccc  180
ggcaaggccc ccaagctgct gatccactac accagcacac tgcagcctgg cgtgcccagc  240
agattttccg gctctggcag cggcagagac ttcaccctga ccatcagcag cctgcagccc  300
gaggacttcg ccacctacta ctgcctgcag tacgactacc tgctgacctt cggccagggc  360
accaaggtgg aaatcaagcg tacggtggcc gccccctccg tgttcatctt cccccccctcc  420
gacgagcagc tgaagtccgg caccgcctcc gtggtgtgcc tgctgaataa cttctacccc  480
agagaggcca aggtgcagtg gaaggtggac aacgccctgc agtccgggaa ctcccaggag  540
agcgtgaccg agcaggacag caaggacagc acctacagcc tgagcagcac cctgaccctg  600
agcaaagccg actacgagaa gcacaaggtg tacgcctgcg aggtgaccca ccagggcctg  660
agctcccccg tcaccaagag cttcaacagg ggggagtgt                          699

SEQ ID NO: 71          moltype = DNA  length = 699
FEATURE                Location/Qualifiers
misc_feature           1..699
                       note = Synthetic
misc_feature           1..699
                       note = Nucleotid sequence encoding huAT01_L2
source                 1..699
                       mol_type = other DNA
                       organism = synthetic construct
SEQUENCE: 71
atggtgctgc agacccaggt gttcatctcc ctgctgctgt ggatctccgg cgcgtacggc  60
```

```
gacatccaga tgacccagag ccctagcagc ctgagcgcca gcgtgggcga cagagtgacc  120
atcacatgca aggccagcca ggacatcaac aagtatatcg cctggtatca gcagaagccc  180
ggcaaggccc ccaagctgct gatccactac accagcacac tgcagcccgg catccccagc  240
agattttccg gctctggcag cggcagagac tacaccctga ccatcagcag cctgcagcca  300
gaggacttcg ccacctacta ctgcctgcag tacgactacc tgctgacctt cggccagggc  360
accaaggtgg aaatcaagcg tacggtggcc gccccctccg tgttcatctt cccccccctcc  420
gacgagcagc tgaagtccgg caccgcctcc gtggtgtgcc tgctgaataa cttctacccc  480
agagaggcca aggtgcagtg gaaggtggac aacgccctgc agtccgggaa ctcccaggag  540
agcgtgaccg agcaggacag caaggacagc acctacagcc tgagcagcac cctgaccctg  600
agcaaagccg actacgagaa gcacaaggtg tacgcctgcg aggtgaccca ccagggcctg  660
agctcccccg tcaccaagag cttcaacagg ggggagtgt                         699

SEQ ID NO: 72          moltype = DNA  length = 1413
FEATURE                Location/Qualifiers
misc_feature           1..1413
                       note = Synthetic
misc_feature           1..1413
                       note = Nucleotid sequence encoding huNB7_H3_IgG1LALA
source                 1..1413
                       mol_type = other DNA
                       organism = synthetic construct
SEQUENCE: 72
atgaaacacc tgtggttctt cctcctgctg gtggcagctc ccagatgggt gctgagcgac  60
gtgcagctgc aggaatctgg ccctggcctc gtgaagccca gcgataccct gagcctgacc  120
tgtaccgtga ccggctacag catcaccagc gactacgcct ggaactggat cagacagccc  180
cctggcaaca agctggaatg gatcggccac atcagctacc ggggcaacac caactacaac  240
cccagcctga agtccagagt gaccatcagc cgggacacca gcaagaacca gttctccctg  300
aagctgagca gcgtgacagc cgccgatacc gccgtgtact actgcgccag ctggaactac  360
tacggctacg tggactatgc catggactac tggggccagg gcaccacagt gaccgtcagc  420
tcagcctcca ccaagggccc aagcgtcttc cccctggcac cctcctccaa gagcacctct  480
ggcggcacag ccgccctggg ctgcctggtc aaggactact tccccgaacc cgtgaccgtg  540
agctggaact caggcgccct gaccagcggc gtgcacacct tccccgctgt cctgcagtcc  600
tcaggactct actccctcag cagcgtggtg accgtgccct ccagcagctt gggcacccag  660
acctacatct gcaacgtgaa tcacaagccc agcaacacca aggtggacaa gagagttgag  720
cccaaatctt gtgacaaaac tcacacatgc ccaccctgcc cagcacctga agccgcgggg  780
ggaccctcag tcttcctctt ccccccaaaa cccaaggaca ccctcatgat ctcccggacc  840
cctgaggtca catgcgtggt ggtggacgtg agccacgaag accctgaggt caagttcaac  900
tggtacgtgg acggcgtgga ggtgcataat gccaagacaa agccccggga ggagcagtac  960
aacagcacgt accgggtggt cagcgtcctc accgtcctgc accaggactg gctgaatggc  1020
aaggagtaca agtgcaaggt ctccaacaaa gccctcccag cccccatcga gaaaaccatc  1080
tccaaagcca aaggccagcc ccgggaacca caggtgtaca ccctgccccc atcccgggag  1140
gagatgacca agaaccaggt cagcctgacc tgcctggtca aaggcttcta tcccagcgac  1200
atcgccgtgg agtgggagag caatggccag cccgagaaca actacaagac caccctccc  1260
gtgctggact ccgacggctc cttcttcctc tacagcaagc tcaccgtgga caagagcagg  1320
tggcagcagg gcaacgtctt ctcatgctcc gtgatgcatg aggctctgca caaccactac  1380
acccagaaga gcctctccct gtctcccggc aaa                            1413

SEQ ID NO: 73          moltype = DNA  length = 1404
FEATURE                Location/Qualifiers
misc_feature           1..1404
                       note = Synthetic
misc_feature           1..1404
                       note = Nucleotid sequence encoding huNB7_H3_IgG4Pro
source                 1..1404
                       mol_type = other DNA
                       organism = synthetic construct
SEQUENCE: 73
atgaaacacc tgtggttctt cctcctgctg gtggcagctc ccagatgggt gctgagcgac  60
gtgcagctgc aggaatctgg ccctggcctc gtgaagccca gcgataccct gagcctgacc  120
tgtaccgtga ccggctacag catcaccagc gactacgcct ggaactggat cagacagccc  180
cctggcaaca agctggaatg gatcggccac atcagctacc ggggcaacac caactacaac  240
cccagcctga agtccagagt gaccatcagc cgggacacca gcaagaacca gttctccctg  300
aagctgagca gcgtgacagc cgccgatacc gccgtgtact actgcgccag ctggaactac  360
tacggctacg tggactatgc catggactac tggggccagg gcaccacagt gaccgtcagc  420
tcagcctcca ccaagggccc tagcgtgttc cctctggccc cttgtagcag aagcaccagc  480
gagtctacag ccgccctggg ctgcctcgtg aaggactact ttcccgagcc cgtgaccgtg  540
tcctggaact ctggcgctct gacaagcggc gtgcacacct ttccagccgt gctgcagagc  600
agcggcctgt actctctgtc cagcgtcgtg actgtgccca gcagctctct gggcaccaag  660
acctacacct gtaacgtgga ccacaagccc agcaacacca aggtggacaa gcgggtggaa  720
tctaagtacg gccctccctg ccctccttgc ccagcccctg aatttctggg cggaccctcc  780
gtgttcctgt tccccccaaa gcccaaggac accctgatga tcagccggac ccccgaagtg  840
acctgcgtgg tggtggatgt gtcccaggaa gatcccgagg tgcagttcaa ttggtacgtg  900
gacggcgtgg aagtgcacaa cgccaagacc aagcctagag aggaacagtt caacagcacc  960
taccgggtgg tgtccgtgct gacagtgctg caccaggact ggctgaacgg caaagagtac  1020
aagtgcaagg tgtccaacaa gggcctgccc agctccatcg agaaaaccat cagcaaggcc  1080
aagggccagc cccgcgaacc ccaggtgtac acactgcctc caagccagga agagatgacc  1140
aagaatcagg tgtccctgac ctgtctcgtg aaaggcttct acccctccga tatcgccgtg  1200
gaatgggaga gcaacggcca gcccgagaac aactacaaga ccaccccccc tgtgctggac  1260
tccgatggct cattcttcct gtacagcaga ctgaccgtgg acaagagccg gtggcaggaa  1320
```

```
ggcaacgtgt tcagctgctc cgtgatgcac gaggccctgc acaaccacta cacccagaag  1380
tccctgtctc tgagcctggg caaa                                         1404

SEQ ID NO: 74          moltype = DNA  length = 699
FEATURE                Location/Qualifiers
misc_feature           1..699
                       note = Synthetic
misc_feature           1..699
                       note = Nucleotid sequence encoding huNB7_L3
source                 1..699
                       mol_type = other DNA
                       organism = synthetic construct
SEQUENCE: 74
atggtgctgc agacccaggt gttcatctcc ctgctgctgt ggatctccgg cgcgtacggc  60
gacatccaga tgacccagag ccctagcagc ctgagcgcca gcgtgggcga cagagtgacc  120
atcacctgta gagccagcca ggacatcagc aactacctga actggtatca gcagaaaccc  180
ggcaaggccg tgaagctgct gatctactac accagcagac tgcacagcgg cgtgcccagc  240
agattttctg gcagcggctc cggcaccgac tacaccctga caatcagcag cctgcagccc  300
gaggacttcg ctacctactt ctgtcagcaa ggcgacacct tccccacctt cggccagggc  360
accaaggtgg aaatcaagcg tacggtggcc gccccctccg tgttcatctt cccccctcc  420
gacgagcagc tgaagtccgg caccgcctcc gtggtgtgcc tgctgaataa cttctacccc  480
agagaggcca aggtgcagtg gaaggtggac aacgccctgc agtccgggaa ctcccaggag  540
agcgtgaccg agcaggacag caaggacagc acctacagcc tgagcagcac cctgaccctg  600
agcaaagccg actacgagaa gcacaaggtg tacgcctgcg aggtgaccca ccagggcctg  660
agctcccccg tcaccaagag cttcaacagg ggggagtgt                         699

SEQ ID NO: 75          moltype = DNA  length = 1137
FEATURE                Location/Qualifiers
source                 1..1137
                       mol_type = other DNA
                       organism = Homo sapiens
SEQUENCE: 75
ccagcctccg gactctagag ccaccatgaa acacctgtgg ttcttcctcc tgctggtggc  60
agctcccaga tgggtgctga gccaggtgca attgtgcagg cggttagctc agcctccacc  120
aagggcccaa gcgtcttccc cctggcaccc tcctccaaga gcacctctgg cggcacagcc  180
gccctgggct gcctggtcaa ggactacttc cccgaacccg tgaccgtgag ctggaactca  240
ggcgccctga ccagcggcgt gcacaccttc cccgctgtcc tgcagtcctc aggactctac  300
tccctcagca gcgtggtgac cgtgccctcc agcagcttgg gcacccagac ctacatctgc  360
aacgtgaatc acaagcccag caacaccaag gtggacaaga gagttgagcc caaatcttgt  420
gacaaaactc acacatgccc accctgccca gcacctgaag ccgcgggggg accctcagtc  480
ttcctcttcc ccccaaaacc caaggacacc ctcatgatct cccggacccc tgaggtcaca  540
tgcgtggtgg tggacgtgag ccacgaagac cctgaggtca agttcaactg gtacgtggac  600
ggcgtggagg tgcataatgc caagacaaag ccccgggagg agcagtacaa cagcacgtac  660
cgggtggtca gcgtcctcac cgtcctgcac caggactggc tgaatggcaa ggagtacaag  720
tgcaaggtct ccaacaaagc cctcccagcc cccatcgaga aaaccatctc caaagccaaa  780
ggccagcccc gggaaccaca ggtgtacacc ctgcccccat cccgggagga gatgaccaag  840
aaccaggtca gcctgacctg cctggtcaaa ggcttctatc ccagcgacat cgccgtggag  900
tgggagagca atggccagcc cgagaacaac tacaagacca cccctcccgt gctggactcc  960
gacggctcct tcttcctcta cagcaagctc accgtggaca agagcaggtg gcagcagggc  1020
aacgtcttct catgctccgt gatgcatgag gctctgcaca accactacac ccagaagagc  1080
ctctccctgt ctcccggcaa atgagatatc gggcccgttt aaacgggggga ggctaac     1137

SEQ ID NO: 76          moltype = DNA  length = 1117
FEATURE                Location/Qualifiers
source                 1..1117
                       mol_type = other DNA
                       organism = Homo sapiens
SEQUENCE: 76
ccagcctccg gactctagag ccaccatgaa acacctgtgg ttcttcctcc tgctggtggc  60
agctcccaga tgggtgctga gccaggtgca attgtgcagg cggttagctc agcctccacc  120
aagggcccta gcgtgttccc tctggcccct tgtagcagaa gcaccagcga gtctacagcc  180
gccctgggct gcctcgtgaa ggactacttt cccgagcccg tgaccgtgtc ctggaactct  240
ggcgctctga caagcggcgt gcacaccttt ccagccgtgc tgcagagcag cggcctgtac  300
tctctgtcca gcgtcgtgac tgtgcccagc agctctctgg gcaccaagac ctacacctgt  360
aacgtggacc acaagcccag caacaccaag gtggacaagc gggtggaatc taagtacggc  420
cctccctgcc ctccttgccc agcccctgaa tttctgggcg gaccctccgt gttcctgttc  480
cccccaaagc ccaaggacac cctgatgatc agccggaccc ccgaagtgac ctgcgtggtg  540
gtggatgtgt cccaggaaga tcccgaggtg cagttcaatt ggtacgtgga cggcgtggaa  600
gtgcacaacg ccaagaccaa gcctagagag gaacagttca acagcaccta ccgggtggtg  660
tccgtgctga cagtgctgca ccaggactgg ctgaacggca aagagtacaa gtgcaaggtg  720
tccaacaagg gcctgcccag ctccatcgag aaaaccatca gcaaggccaa gggccagccc  780
cgcgaacccc aggtgtacac actgcctcca agccaggaag agatgaccaa gaatcaggtg  840
tccctgacct gtctcgtgaa aggcttctac ccctccgata tcgccgtgga atgggagagc  900
aacggccagc ccgagaacaa ctacaagacc acccccctg tgctggactc cgatggctca  960
ttcttcctgt acagcagact gaccgtggac aagagccggt ggcaggaagg caacgtgttc  1020
agctgctccg tgatgcacga ggccctgcac aaccactaca cccagaagtc cctgtctctg  1080
agcctgggca aatgagttta aacgggggag gctaact                           1117

SEQ ID NO: 77          moltype = DNA  length = 348
```

```
FEATURE                Location/Qualifiers
misc_feature           1..348
                       note = Synthetic
misc_feature           1..348
                       note = Nucleotid sequence encoding heavy chain variable
                        region of huAT01_H1
source                 1..348
                       mol_type = other DNA
                       organism = synthetic construct
SEQUENCE: 77
caggtgcagc tggtgcagtc tggcgccgaa gtgaagaaac caggcgccag cgtgaaggtg  60
tcctgcaagg ccagcggcta cacctttacc aacaactggc tgcactgggt gcgccaggct  120
ccaggacagg gactggaatg gatgggcgac atctacccca gcaacggccg gaccaactac  180
gcccagaaat tccagggcag agtgaccatc accgccgaca agagcaccag caccgcctac  240
atggaactga gcagcctgcg gagcgaggac accgccgtgt actactgcgc cagagagcgg  300
ggctacttcg actattgggg ccagggcaca ctcgtgaccg tcagctca               348

SEQ ID NO: 78          moltype = DNA  length = 348
FEATURE                Location/Qualifiers
misc_feature           1..348
                       note = Synthetic
misc_feature           1..348
                       note = Nucleotid sequence encoding heavy chain variable
                        region of huAT01_H3
source                 1..348
                       mol_type = other DNA
                       organism = synthetic construct
SEQUENCE: 78
caggtgcagc tggtgcagtc tggcgccgaa gtgaagaaac caggcgccag cgtgaaggtg  60
tcctgcaagg ccagcggcta cacctttacc aacaactggc tgcactgggt gcgccaggct  120
ccaggacagg gactggaatg gatgggcgac atctacccca gcaacggccg gaccaactac  180
gcccagaaat tccagggcag agtgaccctg accgtggaca agagcaccag caccgcctac  240
atggaactga gcagcctgcg gagcgaggat accgccgtgt acttctgtgc cagagagcgg  300
ggctacttcg actactgggg ccagggaaca ctcgtgaccg tcagctca               348

SEQ ID NO: 79          moltype = DNA  length = 318
FEATURE                Location/Qualifiers
misc_feature           1..318
                       note = Synthetic
misc_feature           1..318
                       note = Nucleotid sequence encoding light chain variable
                        region of huAT01_L1
source                 1..318
                       mol_type = other DNA
                       organism = synthetic construct
SEQUENCE: 79
gacatccaga tgacccagag ccctagcagc ctgagcgcca gcgtgggcga cagagtgacc  60
atcacatgca aggccagcca ggacatcaac aagtatatcg cctggtatca gcagaagccc  120
ggcaaggccc ccaagctgct gatccactac accagcacac tgcagcctgg cgtgcccagc  180
agattttccg gctctggcag cggcagagac ttcaccctga ccatcagcag cctgcagccc  240
gaggacttcg ccacctacta ctgcctgcag tacgactacc tgctgacctt cggccagggc  300
accaaggtgg aaatcaag                                                318

SEQ ID NO: 80          moltype = DNA  length = 318
FEATURE                Location/Qualifiers
misc_feature           1..318
                       note = Synthetic
misc_feature           1..318
                       note = Nucleotid sequence encoding light chain variable
                        region of huAT01_L2
source                 1..318
                       mol_type = other DNA
                       organism = synthetic construct
SEQUENCE: 80
gacatccaga tgacccagag ccctagcagc ctgagcgcca gcgtgggcga cagagtgacc  60
atcacatgca aggccagcca ggacatcaac aagtatatcg cctggtatca gcagaagccc  120
ggcaaggccc ccaagctgct gatccactac accagcacac tgcagcccgg catccccagc  180
agattttccg gctctggcag cggcagagac tacaccctga ccatcagcag cctgcagcca  240
gaggacttcg ccacctacta ctgcctgcag tacgactacc tgctgacctt cggccagggc  300
accaaggtgg aaatcaag                                                318

SEQ ID NO: 81          moltype = DNA  length = 366
FEATURE                Location/Qualifiers
misc_feature           1..366
                       note = Synthetic
misc_feature           1..366
                       note = Nucleotid sequence encoding heavy chain variable
                        region of huNB7_H3
source                 1..366
```

```
                         mol_type = other DNA
                         organism = synthetic construct
SEQUENCE: 81
gacgtgcagc tgcaggaatc tggccctggc ctcgtgaagc ccagcgatac cctgagcctg  60
acctgtaccg tgaccggcta cagcatcacc agcgactacg cctggaactg gatcagacag  120
ccccctggca acaagctgga atggatcggc cacatcagct accggggcaa caccaactac  180
aaccccagcc tgaagtccag agtgaccatc agccgggaca ccagcaagaa ccagttctcc  240
ctgaagctga gcagcgtgac agccgccgat accgccgtgt actactgcgc cagctggaac  300
tactacggct acgtggacta tgccatggac tactggggcc agggcaccac agtgaccgtc  360
agctca                                                            366

SEQ ID NO: 82            moltype = DNA  length = 318
FEATURE                  Location/Qualifiers
misc_feature             1..318
                         note = Synthetic
misc_feature             1..318
                         note = Nucleotid sequence encoding light chain variable
                          region of huNB7_L3
source                   1..318
                         mol_type = other DNA
                         organism = synthetic construct
SEQUENCE: 82
gacatccaga tgacccagag ccctagcagc ctgagcgcca gcgtgggcga cagagtgacc  60
atcacctgta gagccagcca ggacatcagc aactacctga actggtatca gcagaaaccc  120
ggcaaggccg tgaagctgct gatctactac accagcagac tgcacagcgg cgtgcccagc  180
agatttctg gcagcggctc cggcaccgac tacaccctga caatcagcag cctgcagccc  240
gaggacttcg ctacctactt ctgtcagcaa ggcgacacct tccccacctt cggccagggc  300
accaaggtgg aaatcaag                                               318

SEQ ID NO: 83            moltype = AA  length = 1050
FEATURE                  Location/Qualifiers
source                   1..1050
                         mol_type = protein
                         organism = Mus musculus
SEQUENCE: 83
MVFSMWTRKR QILIFLNMLL VSRVFGFRWF PKTLPCEVKV NIPEAHVIVD CTDKHLTEIP  60
EGIPTNTTNL TLTINHIPSI SPDSFRRLNH LEEIDLRCNC VPVLLGSKAN VCTKRLQIRP  120
GSFSGLSDLK ALYLDGNQLL EIPQDLPSSL HLLSLEANNI FSITKENLTE LVNIETLYLG  180
QNCYYRNPCN VSYSIEKDAF LVMRNLKVLS LKDNNVTAVP TTLPPNLLEL YLYNNIIKKI  240
QENDFNNLNE LQVLDLSGNC PRCYNVPYPC TPCENNSPLQ IHDNAFNSLT ELKVLRLHSN  300
SLQHVPPTWF KNMRNLQELD LSQNYLAREI EEAKFLHFLP NLVELDFSFN YELQVYHASI  360
TLPHSLSSLE NLKILRVKGY VFKELKNSSL SVLHKLPRLE VLDLGTNFIK IADLNIFKHF  420
ENLKLIDLSV NKISPSEESR EVGFCPNAQT SVDRHGPQVL EALHYFRYDE YARSCRFKNK  480
EPPSFLPLNA DCHIYGQTLD LSRNNIFFIK PSDFQHLSFL KCLNLSGNTI GQTLNGSELW  540
PLRELRYLDF SNNRLDLLYS TAFEELQSLE VLDLSSNSHY FQAEGITHML NFTKKLRLLD  600
KLMMNDNDIS TSASRTMESD SLRILEFRGN HLDVLWRAGD NRYLDFFKNL FNLEVLDISR  660
NSLNSLPPEV FEGMPPNLKN LSLAKNGLKS FFWDRLQLLK HLEILDLSHN QLTKVPERLA  720
NCSKSLTTLI LKHNQIRQLT KYFLEDALQL RYLDISSNKI QVIQKTSFPE NVLNNLEMLV  780
LHHNRFLCNC DAVWFVWWVN HTDVTIPYLA TDVTCVGPGA HKGQSVISLD LYTCELDLTN  840
LILFSVSISS VLFLMVVMTT SHLFFWDMWY IYYFWKAKIK GYQHLQSMES CYDAFIVYDT  900
KNSAVTEWVL QELVAKLEDP REKHFNLCLE ERDWLPGQPV LENLSQSIQL SKKTVFVMTQ  960
KYAKTESFKM AFYLSHQRLL DEKVDVIILI FLEKPLQKSK FLQLRKRLCR SSVLEWPANP  1020
QAHPYFWQCL KNALTTDNHV AYSQMFKETV                                  1050

SEQ ID NO: 84            moltype = AA  length = 1050
FEATURE                  Location/Qualifiers
source                   1..1050
                         mol_type = protein
                         organism = Rattus norvegicus
SEQUENCE: 84
MVFPMWTLKR QSFIFLNMIL VSRVLGFRWY PKTLPCDVSL DSTNTHVIVD CTDKHLTEIP  60
EGIPTNTTNL TLTINHIPSI SPDSFHRLKH LEELDLRCNC VPILLGSKAN VCTKRLQIRP  120
GSFSGLSDLK SLYLDGNQLL EIPQDLPSSL QLLSLEANNI FSITKENLSE LVNIESLYLG  180
QNCYYRNPCN VSYSIEKDAF LVMKNLKVLS LKDNNVTAVP TILPPNLLEL YLYNNIIKRI  240
QEHDFNKLSQ LQVLDLSGNC PRCYNVPYPC TPCENNSPLQ IHDNAFDSLT ELKVLRLHSN  300
SLQHVPAEWF KNMSNLQELD LSQNYLAREI EEAKFLNSLP NLVQLDLSFN YELQVYHASI  360
TLPHSLSSLT KLKNLYIKGY VFKELKDSSL SVLHNLSNLE VLDLGTNFIK IADLNIFQQF  420
ENLKFIDLSV NKISPSEESR EVGLCPNAQT SVDWHGPQVL EALHYFRYDE YARSCRFKNK  480
EPPTFLPLNA DCHTYGKTLD LSRNNIFFIK PSDFKHLSFL KCLNLSGNAI GQTLNGSELQ  540
PLRELRYLDF SNNRLDLLYS TAFEELQNLE ILDLSSNSHY FQAEGITHML NFTKKLRHLE  600
KLMMNDNDIS TSASRTMESE SLRVLEFRGN HLDVLWRDGD NRYLDFFKNL LNLEELDISR  660
NSLNSVPPGV FEGMPPNLTT LSLAKNGLRS FSWGRLQLLK HLKNLDLSHN QLTTVPARLA  720
NCSKSLTKLI LNHNQIRQLT KYFLEDALQL RYLDISSNKI QVIQKTSFPE NVLNNLNMLL  780
LHHNRFLCNC DAVWFVWWVN HTDVTIPYLA TDVTCAGPGA HKGQSVISLD LYTCELDLTN  840
LILFSVSISS VLFLMIVMTT SHLFFWDMWY IYYFWKAKIK GYQHLQSMES CYDAFIVYDT  900
KNSAVTEWVL QELVVKLEDP REKHFNLCLE ERDWLPGQPV LENLSQSIQL SRKTVFVMTQ  960
KYAKTESFKM AFYLSHQRLM DEKVDVIILI FLEKPLQKSK FLQLRKRLCS SSVLEWPTNP  1020
QAHPYFWQCL KNALTTDNHV AYSQMFKETV                                  1050
```

```
SEQ ID NO: 85           moltype = AA  length = 1049
FEATURE                 Location/Qualifiers
source                  1..1049
                        mol_type = protein
                        organism = Macaca mulatta
SEQUENCE: 85
MMFPVWTLKR QILILFNIIL ISKLLGARWF PKTLPCDVTL DVSKNHVIVD CTDKHLTEIP  60
GGIPTNTTNL TLTINHIPDI SPASFHRLVH LVEIDFRCNC VPIRLGSKSN MCPRRLQIKP  120
RSFSGLTYLK SLYLDGNQLL EIPQGLPPSL QLLSLEANNI FSIRKENLTE LANIEILYLG  180
QNCYYRNPCY VSYSIEKDAF LNLTKLKVLS LKDNNVTTVP TVLPSTLTEL YLYNNMIAEI  240
QEDDFNNLNQ LQILDLSGNC PRCYNAPFPC TPCKNNSPLQ IPVNAFDALT ELKVLRLHSN  300
SLQHVPPRWF KNINNLQELD LSQNFLAKEI GDAKFLHFLP NLIQLDLSFN FELQVYRASM  360
NLSQAFSSLK SLKILRIRGY VFKELKSFNL SPLHNLQNLE VLDLGTNFIK IANLSMFKQF  420
KRLKVIDLSV NKISPSGDSS EVGFCSNART SVESYEPQVL EQLYYFRYDK YARSCRFKNK  480
EASFTSVNES CYKYGQTLDL SKNSIFFIKS SDFQHLSFLK CLNLSGNLIS QTLNGSEFQP  540
LAELRYLDFS NNRLDLLHST AFEELRKLEV LDISSNSHYF QSEGITHMLN FTKNLKVLQK  600
LMMNDNDISS STSRTMESES LRTLEFRGNH LDVLWRDGDN RYLQLFKNLL KLEELDISKN  660
SLSFLPSGVF DGMPPNLKNL SLAKNGLKSF IWEKLRYLKN LETLDLSHNQ LTTVPERLSN  720
CSRSLKNLIL KNNQIRSLTK YFLQDAFQLR YLDLSSNKIQ MIQKTSFPEN VLNNLKMLLL  780
HHNRFLCTCD AVWFVWWVNH TEVTIPYLAT DVTCVGPGAH KGQSVISLDL YTCELDLTNL  840
ILFSLSISVS LFLMVMMTAS HLYFWDVWYI YHFCKAKIKG YQRLISPDCC YDAFIVYDTK  900
DPAVTEWVLA ELVAKLEDPR EKHFNLCLEE RDWLPGQPVL ENLSQSIQLS KKTVFVMTDK  960
YAKTENFKIA FYLSHQRLMD EKVDVIILIF LEKPFQKSKF LQLRKRLCGS SVLEWPTNPQ  1020
AHPYFWQCLK NALATDNHVA YSQVFKETV                                  1049

SEQ ID NO: 86           moltype = DNA  length = 1797
FEATURE                 Location/Qualifiers
misc_feature            1..1797
                        note = Synthetic
misc_feature            1..1797
                        note = Nucleotid sequence of human Unc93B1 D34A mutant-HAx2
                         gene
source                  1..1797
                        mol_type = other DNA
                        organism = synthetic construct
SEQUENCE: 86
atggaggtgg agcctccgct ctaccctgtg gccggggccg cgggtcctca aggggatgaa  60
gaccggcacg gagttcctga tgggccagag gctcccttgg ccgaactcgt gggtgcgtac  120
cccaactaca atgaggagga ggaagagcgc cgctactacc gccgcaagcg cctcggagtg  180
gtcaagaacg tgctggcggc cagcacgggt gtcaccctta cttacggcgt ctacctgggc  240
ctcctgcaga tgcaactgat cctgcactat gatgagacct acagagaggt gaagtatggc  300
aacatggggc tgccggacat cgatagcaag atgctgatgg gtatcaacgt gacgcctatc  360
gctgccctgc tctacacacc tgtgctcatc aggtttttttg gtaccaagtg gatgatgttc  420
ttggctgtgg gcatctatgc cctctttgtc tctaccaact actgggaacg ctactacacg  480
ctggtgccct ctgctgtggc tctgggcatg gccattgtgc ctctgtgggc ctccatgggc  540
aactatatca ccaggatgtc ccagaagtac tatgaatact cccactacaa ggagcaagat  600
gagcagggac ctcagcagcg cccaccacga ggttcccacg caccctatct cctggttttc  660
caggccatct tctatagctt cttccacttg agcttcgcgt gtgcccagct gcccatgatt  720
tacttcctca acaactacct gtatgacctg aaccacacac tgatcaacgt gcagagctgc  780
ggtactaaga gccaaggcat tctgaatggc ttcaacaaga cggtccttcg gacgctgccg  840
cgcagcaaaa accttattgt tgtagagagc gtgctcatgg cggtggcctt cttggccatg  900
ctgatggtgc tgggcctgtg tggagccgct taccggccca cggaagagat cgacctgcgc  960
agcgtgggct ggggcaacat cttccagctg cccttcaaac acgtgcgtga ctttcgctta  1020
cgccatctgg tgcccttctt tatctacagt ggctttgagg tgctctttgc ctgcactggt  1080
tttgccctgg gctacggcgt gtgctccatg ggcctggagc gactggcata cctgctcata  1140
gcttacagcc tgggtgcctc agcctcctcg gttctggggc tgctgggact gtggctgcct  1200
cgctctgtcc cgctcgtggc tggggcagga ctgcacctac tgctcaccct tagcctcttt  1260
ttctgggctc ctgctcctcg ggtcctccag cacagttgga tcttttactt cgtggctgcc  1320
ctctggggtg tgggcagcgc cctcaacaag accggactta gcacactcct gggcatccta  1380
tatgaagaca aagagaggca ggacttcatc ttcaccatct atcactggtg gcaggccgtg  1440
gccatctttg ttgtgtacct gggctccagc ttgcccatga aggccaagct ggcagtgttg  1500
ctggtgaccc tggtagcagc agcagcctca tacctgtgga tggagcagaa gttgcagcaa  1560
ggattggtcc cgcggcagcc gcgcattccg aagccacagc acaaagtccg cggctaccgc  1620
tacctggagg aggacaactc ggatgagagt gacatggagg gcgagcaggg tcagggggac  1680
tgcgcagagg acgaagcacc acaggcaggg cccctgggtg cagagccagc tggcccctgc  1740
cgcaagccct gtccctatga acaggctctg ggtggcgatg ggcctgagga gcagtga     1797
```

-continued

```
SEQ ID NO: 87           moltype = RNA  length = 23
FEATURE                 Location/Qualifiers
misc_feature            1..23
                        note = Synthetic
misc_feature            1..23
                        note = guide RNA targeting the sequence on exon 5 of the
                         mouse TLR7 gene
source                  1..23
                        mol_type = other RNA
                        organism = synthetic construct
SEQUENCE: 87
gaacagttgg ccaatctctc agg                                          23
```

ANTI-HUMAN TLR7 ANTIBODY

CROSS REFERENCES TO RELATED APPLICATIONS

The present application a continuation of U.S. patent application Ser. No. 17/366,820, filed Jul. 2, 2021 (now U.S. Pat. No. 11,578,138), which is a continuation of U.S. patent application Ser. No. 17/069,760, filed Oct. 13, 2020 (now U.S. Pat. No. 11,091,560), which is a continuation-in-part application of International Application No. PCT/JP2019/021466, filed May 30, 2019, which claims priority to Japanese Patent Application No. 2018-104676, filed May 31, 2018, each expressly incorporated herein by reference in its entirety.

STATEMENT REGARDING SEQUENCE LISTING

The Sequence Listing XML associated with this application is provided in XML format and is hereby incorporated by reference into the specification. The name of the XML file containing the sequence listing is 4141-P2USCON2_Seq_List_20221220. The XML file is 164,019 bytes; was created on Dec. 20, 2022; and was submitted electronically via Patent Center with the filing of the specification.

TECHNICAL FIELD

The present invention relates to anti-human Toll-like receptor (TLR) 7 antibodies for treating disorders and diseases.

BACKGROUND ART

In humans, 10 types of TLRs, which are pattern recognition molecules, are known to be present and form one family. Among them, TLR7 (variant 1) is a single transmembrane protein consisting of 1049 amino acids, and the possibility of it playing an important role in the pathogenesis of various inflammatory diseases and autoimmune diseases, by detecting single-stranded RNAs and playing a role in the biological defense reaction through production of type I interferons and cytokines and the like, has been suggested (Non Patent Literature 1). Further, TLR7 (variant 2), which is a single transmembrane protein consisting of 1049 amino acids, is also known to have the same function as TLR7 (variant 1) above (Non Patent Literature 2). In particular, there are many reports suggesting the involvement of TLR7 in diseases such as psoriasis and systemic lupus erythematosus, and it is expected that it is possible to treat such diseases by inhibiting the functions of TLR7 (Non Patent Literature 3).

While TLR7 deficiency acts to reduce symptoms in disease models, drugs capable of specifically inhibiting TLR7 are considered promising in treating inflammatory diseases or the like, based on reports suggesting that TLR9 deficiency is involved in disease progression (Non Patent Literature 4).

Until now, research and development of nucleic acids, low-molecular weight compounds, and the like for inhibiting human TLR7 have been attempted, but it is difficult to inhibit human TLR7 specifically using nucleic acids or low-molecular weight compounds. Further, a mouse anti-mouse TLR7 antibody is known as a TLR7 antibody (Patent Literature 1), but research and development of new human TLR7-specific inhibitors have been required.

CITATION LIST

Patent Literature

Patent Literature 1: International publication No. WO 2014/174704

Non Patent Literature

Non Patent Literature 1: Takeuchi O, Akira S. Cell. 2010 Mar. 19; 140 (6): 805-2

Non Patent Literature 2: Chuang T H, Ulevitch R J, Eur Cytokine Netw. 2000 September; 11 (3): 372-8

Non Patent Literature 3: Lyn-Cook B D, Xie C, Oates J, Treadwell E, Word B, Hammons G, Wiley K. Mol Immunol. 2014 September; 61 (1): 38-43.

Non Patent Literature 4: Christensen S R, Shupe J, Nickerson K, Kashgarian M, Flavell R A, Shlomchik M J Immunity. 2006 September; 25 (3): 417-28.

SUMMARY OF INVENTION

Technical Problem

It is an object of the present invention to provide an agent for treating and/or preventing immune inflammation-related diseases, allergic diseases, infections, and cancers.

Solution to Problem

In order to solve the aforementioned problems, the inventors have searched for a substance having the effect of treating and/or preventing immune inflammation-related diseases, allergic diseases, infections, and cancers, and acquired a mouse anti-human TLR7 antibody. They have accomplished the present invention by humanizing the mouse anti-human TLR7 antibody obtained and further modifying CDRs, frameworks, and variable regions of the humanized antibody.

That is, the present invention includes the following aspects.

(1) An antibody or an antigen-binding fragment of the antibody having the properties of:
   (a) specifically binding to human TLR7 or monkey TLR7 and not binding to mouse TLR7 or rat TLR7; and
   (b) inhibiting a function of human TLR7 or monkey TLR7.

(2) The antibody or the antigen-binding fragment of the antibody according to (1) above, wherein the human TLR7 is a molecule consisting of the amino acid sequence set forth in SEQ ID NO: 2 or SEQ ID NO: 4, the monkey TLR7 is a molecule consisting of the amino acid sequence set forth in SEQ ID NO: 85, the mouse TLR7 is a molecule consisting of the amino acid sequence set forth in SEQ ID NO: 83, or the rat TLR7 is a molecule consisting of the amino acid sequence set forth in SEQ ID NO: 84.

(3) The antibody or the antigen-binding fragment of the antibody according to (1) or (2) above, having a competitive inhibitory activity for binding to human TLR7 with:

an antibody comprising a heavy chain with a heavy-chain variable region consisting of the amino acid sequence set forth in SEQ ID NO: 5 and a light chain with a light-chain variable region consisting of the amino acid sequence set forth in SEQ ID NO: 11;

an antibody comprising a heavy chain with a heavy-chain variable region consisting of the amino acid sequence set forth in SEQ ID NO: 7 and a light chain with a light-chain variable region consisting of the amino acid sequence set forth in SEQ ID NO: 13; or an antibody comprising a heavy chain with a heavy-chain variable region consisting of the amino acid sequence set forth in SEQ ID NO: 9 and a light chain with a light-chain variable region consisting of the amino acid sequence set forth in SEQ ID NO: 15.

(4) The antibody or the antigen-binding fragment of the antibody according to any one of (1) to (3) above, comprising:

(a) CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain;

(b) CDRH1 consisting of the amino acid sequence set forth in SEQ ID NO: 23, CDRH2 consisting of the amino acid sequence set forth in SEQ ID NO: 24 and CDRH3 consisting of the amino acid sequence set forth in SEQ ID NO: 25, as complementarity determining regions in the heavy chain, and CDRL1 consisting of the amino acid sequence set forth in SEQ ID NO: 26, CDRL2 consisting of the amino acid sequence set forth in SEQ ID NO: 27 and CDRL3 consisting of the amino acid sequence set forth in SEQ ID NO: 28, as complementarity determining regions in the light chain; or (c) CDRH1 consisting of the amino acid sequence set forth in SEQ ID NO: 29, CDRH2 consisting of the amino acid sequence set forth in SEQ ID NO: 30 and CDRH3 consisting of the amino acid sequence set forth in SEQ ID NO: 31, as complementarity determining regions in the heavy chain, and CDRL1 consisting of the amino acid sequence set forth in SEQ ID NO: 32, CDRL2 consisting of the amino acid sequence set forth in SEQ ID NO: 33 and CDRL3 consisting of the amino acid sequence set forth in SEQ ID NO: 34, as complementarity determining regions in the light chain.

(5) The antibody or the antigen-binding fragment of the antibody according to (4) above, comprising:

CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain.

(6) The antibody or the antigen-binding fragment of the antibody according to any one of (1) to (5) above, comprising:

(a) a heavy-chain variable region consisting of the amino acid sequence set forth in SEQ ID NO: 5 and a light-chain variable region consisting of the amino acid sequence set forth in SEQ ID NO: 11;

(b) a heavy-chain variable region consisting of the amino acid sequence set forth in SEQ ID NO: 7 and a light-chain variable region consisting of the amino acid sequence set forth in SEQ ID NO: 13; or (c) a heavy-chain variable region consisting of the amino acid sequence set forth in SEQ ID NO: 9 and a light-chain variable region consisting of the amino acid sequence set forth in SEQ ID NO: 15.

(7) The antibody or the antigen-binding fragment of the antibody according to any one of (1) to (6) above, wherein a constant region is a human-derived constant region.

(8) The antibody or the antigen-binding fragment of the antibody according to (7) above, comprising:

(a) a heavy chain consisting of an amino acid sequence at positions 20 to 465 in the amino acid sequence set forth in SEQ ID NO: 35 and a light chain consisting of an amino acid sequence at positions 21 to 233 in the amino acid sequence set forth in SEQ ID NO: 36;

(b) a heavy chain consisting of an amino acid sequence at positions 20 to 471 in the amino acid sequence set forth in SEQ ID NO: 37 and a light chain consisting of an amino acid sequence at positions 21 to 233 in the amino acid sequence set forth in SEQ ID NO: 38, or (c) a heavy chain consisting of an amino acid sequence at positions 20 to 470 in the amino acid sequence set forth in SEQ ID NO: 39 and a light chain consisting of an amino acid sequence at positions 21 to 234 in the amino acid sequence set forth in SEQ ID NO: 40.

(9) The antibody or the antigen-binding fragment of the antibody according to any one of (1) to (8) above, being humanized.

(10) The antibody or the antigen-binding fragment of the antibody according to (9) above, comprising:

(I) a heavy-chain variable region consisting of an amino acid sequence selected from the group consisting of:

(a) the amino acid sequence set forth in SEQ ID NO: 41;

(b) the amino acid sequence set forth in SEQ ID NO: 42;

(c) an amino acid sequence having a homology of at least 95% or more to the sequence (a) or (b); and (d) an amino acid sequence derived from the sequence (a) or (b) by deletion, substitution or addition of 1 to 10 amino acids; and a light-chain variable region consisting of an amino acid sequence selected from the group consisting of:

(e) the amino acid sequence set forth in SEQ ID NO: 43;

(f) the amino acid sequence set forth in SEQ ID NO: 44;

(g) an amino acid sequence having a homology of at least 95% or more to the sequence (e) or (f); and (h) an amino acid sequence derived from the sequence (e) or (f) by deletion, substitution or addition of 1 to 10 amino acids; or (II) a heavy-chain variable region consisting of an amino acid sequence selected from the group consisting of:
(a) the amino acid sequence set forth in SEQ ID NO: 50;
(b) an amino acid sequence having a homology of at least 95% or more to the sequence (a); and
(c) an amino acid sequence derived from the sequence (a) by deletion, substitution or addition of 1 to 10 amino acids; and
a light-chain variable region consisting of an amino acid sequence selected from the group consisting of:
(d) the amino acid sequence set forth in SEQ ID NO: 51;
(e) an amino acid sequence having a homology of at least 95% or more to the sequence (d); and
(f) an amino acid sequence derived from the sequence (d) by deletion, substitution or addition of 1 to 10 amino acids.

(11) The antibody or the antigen-binding fragment of the antibody according to (10) above, comprising:
(a) a heavy-chain variable region consisting of the amino acid sequence set forth in SEQ ID NO: 41 and a light-chain variable region consisting of the amino acid sequence set forth in SEQ ID NO: 43;
(b) a heavy-chain variable region consisting of the amino acid sequence set forth in SEQ ID NO: 41 and a light-chain variable region consisting of the amino acid sequence set forth in SEQ ID NO: 44;
(c) a heavy-chain variable region consisting of the amino acid sequence set forth in SEQ ID NO: 42 and a light-chain variable region consisting of the amino acid sequence set forth in SEQ ID NO: 43;
(d) a heavy-chain variable region consisting of the amino acid sequence set forth in SEQ ID NO: 42 and a light-chain variable region consisting of the amino acid sequence set forth in SEQ ID NO: 44; or
(e) a heavy-chain variable region consisting of the amino acid sequence set forth in SEQ ID NO: 50 and a light-chain variable region consisting of the amino acid sequence set forth in SEQ ID NO: 51.

(12) The antibody or the antigen-binding fragment of the antibody according to (11) above, comprising a heavy-chain variable region consisting of the amino acid sequence set forth in SEQ ID NO: 42 and a light-chain variable region consisting of the amino acid sequence set forth in SEQ ID NO: 44.

(13) The antibody or the antigen-binding fragment of the antibody according to (11) above, comprising:
(a) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48;
(b) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 49;
(c) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48;
(d) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49;
(e) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 48;
(f) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49;
(g) a heavy chain consisting of an amino acid sequence at positions 20 to 471 in the amino acid sequence set forth in SEQ ID NO: 52 and a light chain consisting of an amino acid sequence at positions 21 to 233 in the amino acid sequence set forth in SEQ ID NO: 53; or
(h) a heavy chain consisting of an amino acid sequence at positions 20 to 468 in the amino acid sequence set forth in SEQ ID NO: 54 and a light chain consisting of an amino acid sequence at positions 21 to 233 in the amino acid sequence set forth in SEQ ID NO: 53.

(14) The antibody or the antigen-binding fragment of the antibody according to (13) above, comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

(15) An antibody or an antigen-binding fragment of the antibody having the properties of:
(a) specifically binding to human TLR7,
(b) inhibiting a function of human TLR7, and
(c) comprising:
(1) CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain;
(2) CDRH1 consisting of the amino acid sequence set forth in SEQ ID NO: 23, CDRH2 consisting of the amino acid sequence set forth in SEQ ID NO: 24 and CDRH3 consisting of the amino acid sequence set forth in SEQ ID NO: 25, as complementarity determining regions in the heavy chain, and CDRL1 consisting of the amino acid sequence set forth in SEQ ID NO: 26, CDRL2 consisting of the amino acid sequence set forth in SEQ ID NO: 27 and CDRL3 consisting of the amino acid sequence set forth in SEQ ID NO: 28, as complementarity determining regions in the light chain; or
(3) CDRH1 consisting of the amino acid sequence set forth in SEQ ID NO: 29, CDRH2 consisting of the amino acid sequence set forth in SEQ ID NO: 30 and CDRH3 consisting of the amino acid sequence set forth in SEQ ID NO: 31, as complementarity determining regions in the heavy chain, and CDRL1 consisting of the amino acid sequence set forth in SEQ ID NO: 32, CDRL2 consisting of the amino acid sequence set forth in SEQ ID NO: 33 and CDRL3 consisting of the amino acid sequence set forth in SEQ ID NO: 34, as complementarity determining regions in the light chain.

(16) The antibody or the antigen-binding fragment of the antibody according to (15) above, comprising:
CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and
CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain.

(17) The antibody or the antigen-binding fragment of the antibody according to (15) or (16) above, comprising:
(a) a heavy-chain variable region consisting of the amino acid sequence set forth in SEQ ID NO: 5 and a light-chain variable region consisting of the amino acid sequence set forth in SEQ ID NO: 11;
(b) a heavy-chain variable region consisting of the amino acid sequence set forth in SEQ ID NO: 7 and a light-chain variable region consisting of the amino acid sequence set forth in SEQ ID NO: 13; or
(c) a heavy-chain variable region consisting of the amino acid sequence set forth in SEQ ID NO: 9 and a light-chain variable region consisting of the amino acid sequence set forth in SEQ ID NO: 15.

(18) The antibody or the antigen-binding fragment of the antibody according to any one of (15) to (17) above, wherein a constant region is a human-derived constant region.

(19) The antibody or the antigen-binding fragment of the antibody according to (18) above, comprising:
(a) a heavy chain consisting of an amino acid sequence at positions 20 to 465 in the amino acid sequence set forth in SEQ ID NO: 35 and a light chain consisting of an amino acid sequence at positions 21 to 233 in the amino acid sequence set forth in SEQ ID NO: 36;
(b) a heavy chain consisting of an amino acid sequence at positions 20 to 471 in the amino acid sequence set forth in SEQ ID NO: 37 and a light chain consisting of an amino acid sequence at positions 21 to 233 in the amino acid sequence set forth in SEQ ID NO: 38, or
(c) a heavy chain consisting of an amino acid sequence at positions 20 to 470 in the amino acid sequence set forth in SEQ ID NO: 39 and a light chain consisting of an amino acid sequence at positions 21 to 234 in the amino acid sequence set forth in SEQ ID NO: 40.

(20) The antibody or the antigen-binding fragment of the antibody according to any one of (15) to (19) above, being humanized.

(21) The antibody or the antigen-binding fragment of the antibody according to (20) above, comprising:
(I) a heavy-chain variable region consisting of an amino acid sequence selected from the group consisting of:
(a) the amino acid sequence set forth in SEQ ID NO: 41;
(b) the amino acid sequence set forth in SEQ ID NO: 42;
(c) an amino acid sequence having a homology of at least 95% or more to the sequence (a) or (b); and
(d) an amino acid sequence derived from the sequence (a) or (b) by deletion, substitution or addition of 1 to 10 amino acids; and
a light-chain variable region consisting of an amino acid sequence selected from the group consisting of:
(e) the amino acid sequence set forth in SEQ ID NO: 43;
(f) the amino acid sequence set forth in SEQ ID NO: 44;
(g) an amino acid sequence having a homology of at least 95% or more to the sequence (e) or (f); and
(h) an amino acid sequence derived from the sequence (e) or (f) by deletion, substitution or addition of 1 to 10 amino acids; or
(II) a heavy-chain variable region consisting of an amino acid sequence selected from the group consisting of:
(a) the amino acid sequence set forth in SEQ ID NO: 50;
(b) an amino acid sequence having a homology of at least 95% or more to the sequence (a); and
(c) an amino acid sequence derived from the sequence (a) by deletion, substitution or addition of 1 to 10 amino acids; and
a light-chain variable region consisting of an amino acid sequence selected from the group consisting of:
(d) the amino acid sequence set forth in SEQ ID NO: 51;
(e) an amino acid sequence having a homology of at least 95% or more to the sequence (d); and
(f) an amino acid sequence derived from the sequence (d) by deletion, substitution or addition of 1 to 10 amino acids.

(22) The antibody or the antigen-binding fragment of the antibody according to (21) above, comprising:
(a) a heavy-chain variable region consisting of the amino acid sequence set forth in SEQ ID NO: 41 and a light-chain variable region consisting of the amino acid sequence set forth in SEQ ID NO: 43;
(b) a heavy-chain variable region consisting of the amino acid sequence set forth in SEQ ID NO: 41 and a light-chain variable region consisting of the amino acid sequence set forth in SEQ ID NO: 44;
(c) a heavy-chain variable region consisting of the amino acid sequence set forth in SEQ ID NO: 42 and a light-chain variable region consisting of the amino acid sequence set forth in SEQ ID NO: 43;
(d) a heavy-chain variable region consisting of the amino acid sequence set forth in SEQ ID NO: 42 and a light-chain variable region consisting of the amino acid sequence set forth in SEQ ID NO: 44; or
(e) a heavy-chain variable region consisting of the amino acid sequence set forth in SEQ ID NO: 50 and a light-chain variable region consisting of the amino acid sequence set forth in SEQ ID NO: 51.

(23) The antibody or the antigen-binding fragment of the antibody according to (22) above, comprising a heavy-chain variable region consisting of the amino acid sequence set forth in SEQ ID NO: 42 and a light-chain variable region consisting of the amino acid sequence set forth in SEQ ID NO: 44.

(24) The antibody or the antigen-binding fragment of the antibody according to (22) above, comprising:
(a) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48;

(b) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 49;

(c) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48;

(d) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49;

(e) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 48;

(f) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49;

(g) a heavy chain consisting of an amino acid sequence at positions 20 to 471 in the amino acid sequence set forth in SEQ ID NO: 52 and a light chain consisting of an amino acid sequence at positions 21 to 233 in the amino acid sequence set forth in SEQ ID NO: 53; or (h) a heavy chain consisting of an amino acid sequence at positions 20 to 468 in the amino acid sequence set forth in SEQ ID NO: 54 and a light chain consisting of an amino acid sequence at positions 21 to 233 in the amino acid sequence set forth in SEQ ID NO: 53.

(25) The antibody or the antigen-binding fragment of the antibody according to (24) above, comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

(26) An antibody or an antigen-binding fragment of the antibody comprising a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48.

(27) An antibody or an antigen-binding fragment of the antibody comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48.

(28) An antibody or an antigen-binding fragment of the antibody comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

(29) An antibody or an antigen-binding fragment of the antibody comprising a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49.

(30) An antibody or an antigen-binding fragment of the antibody comprising a heavy chain consisting of an amino acid sequence at positions 20 to 471 in the amino acid sequence set forth in SEQ ID NO: 52 and a light chain consisting of an amino acid sequence at positions 21 to 233 in the amino acid sequence set forth in SEQ ID NO: 53.

(31) An antibody or an antigen-binding fragment of the antibody comprising a heavy chain consisting of an amino acid sequence at positions 20 to 468 in the amino acid sequence set forth in SEQ ID NO: 54 and a light chain consisting of an amino acid sequence at positions 21 to 233 in the amino acid sequence set forth in SEQ ID NO: 53.

(32) The antibody or the antigen-binding fragment of the antibody according to any one of (26) to (31) above, having the properties of:

(a) specifically binding to human TLR7; and (b) inhibiting a function of human TLR7.

(33) The antigen-binding fragment of the antibody according to any one of (1) to (32) above, wherein the antigen-binding fragment is selected from the group consisting of Fab, $F(ab)_2$, Fab' and Fv.

(34) A polynucleotide comprising a polynucleotide sequence encoding the antibody or the antigen-binding fragment of the antibody according to any one of (1) to (33) above.

(35) The polynucleotide according to (34) above, comprising:

(1) a polynucleotide sequence encoding CDRH1 consisting of the amino acid sequence set forth in SEQ ID NO: 17, a polynucleotide sequence encoding CDRH2 consisting of the amino acid sequence set forth in SEQ ID NO: 18 and a polynucleotide sequence encoding CDRH3 consisting of the amino acid sequence set forth in SEQ ID NO: 19, and a polynucleotide sequence encoding CDRL1 consisting of the amino acid sequence set forth in SEQ ID NO: 20, a polynucleotide sequence encoding CDRL2 consisting of the amino acid sequence set forth in SEQ ID NO: 21 and a polynucleotide sequence encoding CDRL3 consisting of the amino acid sequence set forth in SEQ ID NO: 22;

(2) a polynucleotide sequence encoding CDRH1 consisting of the amino acid sequence set forth in SEQ ID NO: 23, a polynucleotide sequence encoding CDRH2 consisting of the amino acid sequence set forth in SEQ ID NO: 24 and a polynucleotide sequence encoding CDRH3 consisting of the amino acid sequence set forth in SEQ ID NO: 25, and a polynucleotide sequence encoding CDRL1 consisting of the amino acid sequence set forth in SEQ ID NO: 26, a polynucleotide sequence encoding CDRL2 consisting of the amino acid sequence set forth in SEQ ID NO: 27 and a polynucleotide sequence encoding CDRL3 consisting of the amino acid sequence set forth in SEQ ID NO: 28; or (3) a polynucleotide sequence encoding CDRH1 consisting of the amino acid sequence set forth in SEQ ID NO: 29, a polynucleotide sequence encoding CDRH2 consisting of the amino acid sequence set forth in SEQ ID NO: 30 and a polynucleotide sequence encoding CDRH3 consisting of the amino acid sequence set forth in SEQ ID NO: 31, and a polynucleotide sequence encoding CDRL1 consisting of the amino acid sequence set forth in SEQ ID NO: 32, a polynucleotide sequence encoding CDRL2 consisting of the amino acid sequence set forth in SEQ ID NO: 33 and a polynucleotide sequence encoding CDRL3 consisting of the amino acid sequence set forth in SEQ ID NO: 34.

(36) The polynucleotide according to (35) above, comprising:

(I) a polynucleotide sequence selected from the group consisting of:

(a) a polynucleotide sequence encoding the heavy-chain variable region set forth in SEQ ID NO: 77;

(b) a polynucleotide sequence encoding the heavy-chain variable region set forth in SEQ ID NO: 78; and (c) a polynucleotide sequence of a polynucleotide which hybridizes with a polynucleotide consisting of a polynucleotide sequence complementary to the polynucleotide sequence (a) or (b) under stringent conditions; and a polynucleotide sequence selected from the group consisting of:

(d) a polynucleotide sequence encoding the light-chain variable region set forth in SEQ ID NO: 79;

(e) a polynucleotide sequence encoding the light-chain variable region set forth in SEQ ID NO: 80; and (f) a polynucleotide sequence of a polynucleotide which hybridizes with a polynucleotide consisting of a polynucleotide sequence complementary to the polynucleotide sequence (d) or (e) under stringent conditions; or (II) a polynucleotide sequence selected from the group consisting of:

(a) a polynucleotide sequence encoding the heavy-chain variable region set forth in SEQ ID NO: 81; and (b) a polynucleotide sequence of a polynucleotide which hybridizes with a polynucleotide consisting of a polynucleotide sequence complementary to the polynucleotide sequence (a) under stringent conditions; and a polynucleotide sequence selected from the group consisting of:

(c) a polynucleotide sequence encoding the light-chain variable region set forth in SEQ ID NO: 82; and (d) a polynucleotide sequence of a polynucleotide which hybridizes with a polynucleotide consisting of a polynucleotide sequence complementary to the polynucleotide sequence (c) under stringent conditions.

(37) The polynucleotide according to (36) above, comprising:

(a) a polynucleotide sequence encoding the heavy-chain variable region set forth in SEQ ID NO: 77 and a polynucleotide sequence encoding the light-chain variable region set forth in SEQ ID NO: 79;

(b) a polynucleotide sequence encoding the heavy-chain variable region set forth in SEQ ID NO: 77 and a polynucleotide sequence encoding the light-chain variable region set forth in SEQ ID NO: 80;

(c) a polynucleotide sequence encoding the heavy-chain variable region set forth in SEQ ID NO: 78 and a polynucleotide sequence encoding the light-chain variable region set forth in SEQ ID NO: 79;

(d) a polynucleotide sequence encoding the heavy-chain variable region set forth in SEQ ID NO: 78 and a polynucleotide sequence encoding the light-chain variable region set forth in SEQ ID NO: 80; or (e) a polynucleotide sequence encoding the heavy-chain variable region set forth in SEQ ID NO: 81 and a polynucleotide sequence encoding the light-chain variable region set forth in SEQ ID NO: 82.

(38) An expression vector comprising the polynucleotide according to any one of (34) to (37) above.

(39) A host cell transformed with the expression vector according to (38) above.

(40) The host cell according to (39) above, wherein the host cell is a eukaryotic cell.

(41) A method for producing an antibody or an antigen-binding fragment of the antibody, comprising the steps of:

culturing the host cell according to (39) or (40) above; and collecting the antibody or the fragment of interest from the culture obtained in the above step.

(42) An antibody or an antigen-binding fragment of the antibody obtained by the production method according to (41).

(43) The antibody according to any one of (1) to (32) above, comprising one or more modifications selected from the group consisting of glycosylation to N-linkage, glycosylation to O-linkage, N-terminal processing, C-terminal processing, deamidation, isomerization of aspartic acid, oxidation of methionine, addition of a methionine residue to N-terminal, amidation of a proline residue, and deletion of one or two amino acids at the carboxyl terminus of the heavy chain.

(44) The antibody according to (43) above, comprising: two heavy chains consisting of one kind of or a combination of any two kinds of heavy chains selected from the group consisting of the full length and deletion variants with one or two amino acids deleted at the carboxyl terminus.

(45) The antibody according to (44) above, wherein one amino acid is deleted at the carboxyl terminus in each of the two heavy chains.

(46) The antibody according to any one of (43) to (45) above, wherein a proline residue at the carboxyl terminus of the heavy chain is further amidated.

(47) A pharmaceutical composition for treating and/or preventing a disease, comprising: at least one of the antibodies or the antigen-binding fragments of the antibodies according to (1) to (33) and (42) to (46) above, or the expression vector according to (38) as an active ingredient.

(48) The pharmaceutical composition according to (47) above, for treating a disease caused by a function of human TLR7.

(49) The pharmaceutical composition according to (48) above, wherein the disease caused by a function of human TLR7 is an immune inflammation-related disease, an allergic disease, an infection or a cancer.

(50) The pharmaceutical composition according to (49) above, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

(51) The pharmaceutical composition according to (49) or (50) above, wherein the immune inflammation-related disease is systemic lupus erythematosus.

(52) The pharmaceutical composition according to any one of (47) to (51) above, to be used in combination with an immunosuppressant, an anti-inflammatory drug, an anti-allergic agent, an anti-infective agent, or an anticancer agent.

(53) A method for treating a disease caused by a function of human TLR7, comprising: administering at least one of the antibodies or the antigen-binding fragments of the antibodies according to (1) to (33) and (42) to (46) above to an individual.

(54) A method for treating a disease caused by a function of human TLR7, comprising administering at least one of the antibodies or the antigen-binding fragments of the antibodies according to (1) to (33) and (42) to (46) above together with an immunosuppressant, an anti-inflammatory drug, an anti-allergic agent, an anti-infective agent or an anticancer agent, simultaneously, separately or sequentially to an individual.

(55) The treatment method according to (53) or (54) above, wherein the disease caused by a function of human TLR7 is an immune inflammation-related disease, an allergic disease, an infection or a cancer.

(56) The treatment method according to (55) above, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

(57) The treatment method according to (55) or (56) above, wherein the immune inflammation-related disease is systemic lupus erythematosus.

(58) The antibody or the antigen-binding fragment of the antibody according to any one of (1) to (33) and (42) to (46) above, or the expression vector according to (38) above, to be used for treating or preventing a disease caused by a function of human TLR7.

(59) The antibody, the antigen-binding fragment of the antibody, or the expression vector according to (58) above, wherein the disease caused by a function of human TLR7 is an immune inflammation-related disease, an allergic disease, an infection or a cancer.

(60) The antibody, the antigen-binding fragment of the antibody, or the expression vector according to (59) above, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

(61) The antibody, the antigen-binding fragment of the antibody, or the expression vector according to (59) or (60) above, wherein the immune inflammation-related disease is systemic lupus erythematosus.

(62) The antibody, the antigen-binding fragment of the antibody, or the expression vector according to any one of (58) to (61) above, to be used in combination with an immunosuppressant, an anti-inflammatory drug, an anti-allergic agent, an anti-infective agent or an anticancer agent.

(63) Use of the antibody or the antigen-binding fragment of the antibody according to any one of (1) to (33) and (42) to (46) above, or the expression vector according to (38) above, for producing a therapeutic agent or a preventive agent for a disease caused by a function of human TLR7.

(64) The use according to (63) above, wherein the disease caused by a function of human TLR7 is an immune inflammation-related disease, an allergic disease, an infection or a cancer.

(65) The use according to (64) above, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

(66) The use according to (64) or (65) above, wherein the immune inflammation-related disease is systemic lupus erythematosus.

(67) The use according to any one of (63) to (66) above, wherein the therapeutic agent or the preventive agent is used in combination with an immunosuppressant, an anti-inflammatory drug, an anti-allergic agent, an anti-infective agent or an anticancer agent.

Advantageous Effects of Invention

According to the present invention, an agent having a mechanism of action of inhibiting a function of TLR7 for treating and/or preventing immune inflammation-related diseases, allergic diseases, infections, and cancers can be obtained.

BRIEF DESCRIPTION OF DRAWINGS

FIG. 1 shows the amino acid sequence (SEQ ID NO: 2) of human TLR7 (variant 1).

FIG. 2 shows the amino acid sequence (SEQ ID NO: 4) of human TLR7 (variant 2).

FIG. 3 shows the amino acid sequence (SEQ ID NO: 83) of mouse TLR7.

FIG. 4 shows the amino acid sequence (SEQ ID NO: 84) of rat TLR7.

FIG. 5 shows the amino acid sequence (SEQ ID NO: 85) of monkey TLR7.

FIG. 7 shows the amino acid sequence (SEQ ID NO: 35) of the heavy chain of the cAT01 antibody, which includes the signal sequence thereof, and the amino acid sequence (SEQ ID NO: 36) of the light chain of the cAT01 antibody, which includes the signal sequence thereof. In the heavy-chain amino acid sequence, the amino acid sequence at positions 1 to 19 is the signal sequence, the amino acid sequence at positions 20 to 135 is the heavy-chain variable region, and the amino acid sequence at positions 136 to 465 is the heavy-chain constant region. In the light-chain amino acid sequence, the amino acid sequence at positions 1 to 20 is the signal sequence, the amino acid sequence at positions 21 to 126 is the light-chain variable region, and the amino acid sequence at positions 127 to 233 is the light-chain constant region. FIG. 8 shows the amino acid sequence (SEQ ID NO: 37) of the heavy chain of the cNB7 antibody, which includes the signal sequence thereof, and the amino acid sequence (SEQ ID NO: 38) of the light chain of the cNB7 antibody, which includes the signal sequence thereof. In the heavy-chain amino acid sequence, the amino acid sequence at positions 1 to 19 is the signal sequence, the amino acid sequence at positions 20 to 141 is the heavy-chain variable region, and the amino acid sequence at positions 142 to 471 is the heavy-chain constant region. In the light-chain amino acid sequence, the amino acid sequence at positions 1 to 20 is the signal sequence, the amino acid sequence at positions 21 to 126 is the light-chain variable region, and the amino acid sequence at positions 127 to 233 is the light-chain constant region. FIG. 9 shows the amino acid sequence (SEQ ID NO: 39) of the heavy chain of the cFAN2 antibody, which includes the signal sequence thereof, and the amino acid sequence (SEQ ID NO: 40) of the light chain of the cFAN2 antibody, which includes the signal sequence thereof. In the heavy-chain amino acid sequence, the amino acid sequence at positions 1 to 19 is the signal sequence, the amino acid sequence at positions 20 to 140 is the heavy-chain variable region, and the amino acid sequence at positions 141 to 470 is the heavy-chain constant region. In the light-chain amino acid sequence, the amino acid sequence at positions 1 to 20 is the signal sequence, the amino acid sequence at positions 21 to 127 is the light-chain variable region, and the amino acid sequence at positions 128 to 234 is the light-chain constant region.

FIG. 11 shows the amino acid sequence (SEQ ID NO: 45) of the heavy chain of huAT01_H1_IgG1LALA, which includes the signal sequence thereof, and which is a humanized heavy chain. In the sequence, the amino acid sequence at positions 1 to 19 is the signal sequence, the amino acid sequence at positions 20 to 135 is the variable region, and the amino acid sequence at positions 136 to 465 is the constant region. Further, the amino acid sequence at positions 45 to 54 is CDRH1, the amino acid sequence at positions 69 to 78 is CDRH2, and the amino acid sequence at positions 118 to 124 is CDRH3.

FIG. 12 shows the amino acid sequence (SEQ ID NO: 46) of the heavy chain of huAT01_H3_IgG1LALA, which includes the signal sequence thereof, and which is a humanized heavy chain. In the sequence, the amino acid sequence at positions 1 to 19 is the signal sequence, the amino acid sequence at positions 20 to 135 is the variable region, and the amino acid sequence at positions 136 to 465 is the constant region. Further, the amino acid sequence at positions 45 to 54 is CDRH1, the amino acid sequence at positions 69 to 78 is CDRH2, and the amino acid sequence at positions 118 to 124 is CDRH3.

FIG. 13 shows the amino acid sequence (SEQ ID NO: 47) of the heavy chain of huAT01_H3_IgG4Pro, which includes the signal sequence thereof, and which is a humanized heavy chain. In the sequence, the amino acid sequence at positions 1 to 19 is the signal sequence, the amino acid sequence at positions 20 to 135 is the variable region, and the amino acid sequence at positions 136 to 462 is the constant region. Further, the amino acid sequence at positions 45 to 54 is CDRH1, the amino acid sequence at positions 69 to 78 is CDRH2, and the amino acid sequence at positions 118 to 124 is CDRH3.

FIG. 14 shows the comparison of the amino acid sequence (SEQ ID NO: 5) of the variable region of cAT01_H, which is the heavy chain of chimeric antibody cAT01 (which will be hereinafter referred to as cAT01_H), the amino acid sequence (SEQ ID NO: 41) of the variable region of humanized antibody heavy chain huAT01_H1_IgG1LALA (which will be hereinafter referred to as huAT01_H1), and the amino acid sequence (SEQ ID NO: 42) of the variable region of humanized antibody heavy chain huAT01_H3_IgG1LALA (which will be hereinafter referred to as huAT01_H3). In the sequences of huAT01_H1 and huAT01_H3, the symbol "·" represents the same amino acid residue as that of cAT01_H, and a substituted amino acid residue is shown in the site where the amino acid residue is described.

FIG. 15 shows the amino acid sequence (SEQ ID NO: 48) of the light chain of huAT01_L1, which includes the signal sequence thereof and which is a humanized light chain. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

FIG. 16 shows the amino acid sequence (SEQ ID NO: 49) of the light chain of huAT01_L2, which includes the signal sequence thereof and which is a humanized light chain. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

FIG. 17 shows the comparison of the amino acid sequence (SEQ ID NO: 11) of the variable region of cAT01_L, which is the light chain of chimeric antibody cAT01 (which will be hereinafter referred to as cAT01_L), the amino acid sequence (SEQ ID NO: 43) of the variable region of humanized antibody light chain huAT01_L1 (which will be hereinafter referred to as huAT01_L1), and the amino acid sequence (SEQ ID NO: 44) of the variable region of humanized antibody light chain huAT01_L2 (which will be hereinafter referred to as huAT01_L2). In the sequences of huAT01_L1 and huAT01_L2, the symbol "·" represents the same amino acid residue as that of cAT01_L, and a substituted amino acid residue is shown in the site where the amino acid residue is described.

FIG. 18 shows the amino acid sequence (SEQ ID NO: 52) of the heavy chain of huNB7_H3_IgG1LALA, which includes the signal sequence thereof and which is a humanized heavy chain. In the sequence, the amino acid sequence at positions 1 to 19 is the signal sequence, the amino acid sequence at positions 20 to 141 is the variable region, and the amino acid sequence at positions 142 to 471 is the constant region. Further, the amino acid sequence at positions 45 to 55 is CDRH1, the amino acid sequence at positions 70 to 78 is CDRH2, and the amino acid sequence at positions 118 to 130 is CDRH3.

FIG. 19 shows the amino acid sequence (SEQ ID NO: 54) of the heavy chain of huNB7_H3_IgG4Pro, which includes the signal sequence thereof and which is a humanized heavy chain. In the sequence, the amino acid sequence at positions 1 to 19 is the signal sequence, the amino acid sequence at positions 20 to 141 is the variable region, and the amino acid sequence at positions 142 to 468 is the constant region. Further, the amino acid sequence at positions 45 to 55 is CDRH1, the amino acid sequence at positions 70 to 78 is CDRH2, and the amino acid sequence at positions 118 to 130 is CDRH3.

FIG. 20 shows the comparison of the amino acid sequence (SEQ ID NO: 7) of the variable region of cNB7_H, which is the heavy chain of chimeric antibody cNB7 (which will be hereinafter referred to as cNB7_H) and the amino acid sequence (SEQ ID NO: 50) of the variable region of humanized antibody heavy chain huNB7_H3_IgG1LALA (which will be hereinafter referred to as huNB7_H3). In huNB7_H3, the symbol "·" represents the same amino acid residue as that of cNB7_H, and a substituted amino acid residue is shown in the site where the amino acid residue is described.

FIG. 21 shows the amino acid sequence (SEQ ID NO: 53) of the light chain of huNB7_L3, which includes the signal sequence thereof and which is a humanized light chain. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

FIG. 22 shows the comparison of the amino acid sequence (SEQ ID NO: 13) of the variable region of cNB7_L, which is the light chain of chimeric antibody cNB7 (which will be hereinafter referred to as cNB7_L) and the amino acid sequence (SEQ ID NO: 51) of the variable region of humanized antibody light chain huNB7_L3 (which will be hereinafter referred to as huNB7_L3). In huNB7_L3, the symbol "·" represents the same amino acid residue as that of cNB7_L, and a substituted amino acid residue is shown in the site where the amino acid residue is described.

FIG. 24-1 shows the amino acid sequence (SEQ ID NO: 17) of CDRH1 of AT01 antibody, the amino acid sequence (SEQ ID NO: 18) of CDRH2 thereof, the amino acid sequence (SEQ ID NO: 19) of CDRH3 thereof, the amino acid sequence (SEQ ID NO: 20) of CDRL1 thereof, the amino acid sequence (SEQ ID NO: 21) of CDRL2 thereof, and the amino acid sequence (SEQ ID NO: 22) of CDRL3 thereof. FIG. 24-2 shows the amino acid sequence (SEQ ID NO: 23) of CDRH1 of NB7 antibody, the amino acid sequence (SEQ ID NO: 24) of CDRH2 thereof, the amino acid sequence (SEQ ID NO: 25) of CDRH3 thereof, the amino acid sequence (SEQ ID NO: 26) of CDRL1 thereof, the amino acid sequence (SEQ ID NO: 27) of CDRL2 thereof, and the amino acid sequence (SEQ ID NO: 28) of CDRL3 thereof. FIG. 24-3 shows the amino acid sequence (SEQ ID NO: 29) of CDRH1 of FAN2 antibody, the amino acid sequence (SEQ ID NO: 30) of CDRH2 thereof, the amino acid sequence (SEQ ID NO: 31) of CDRH3 thereof, the amino acid sequence (SEQ ID NO: 32) of CDRL1 thereof, the amino acid sequence (SEQ ID NO: 33) of CDRL2 thereof, and the amino acid sequence (SEQ ID NO: 34) of CDRL3 thereof.

DESCRIPTION OF EMBODIMENTS

Figure 6:
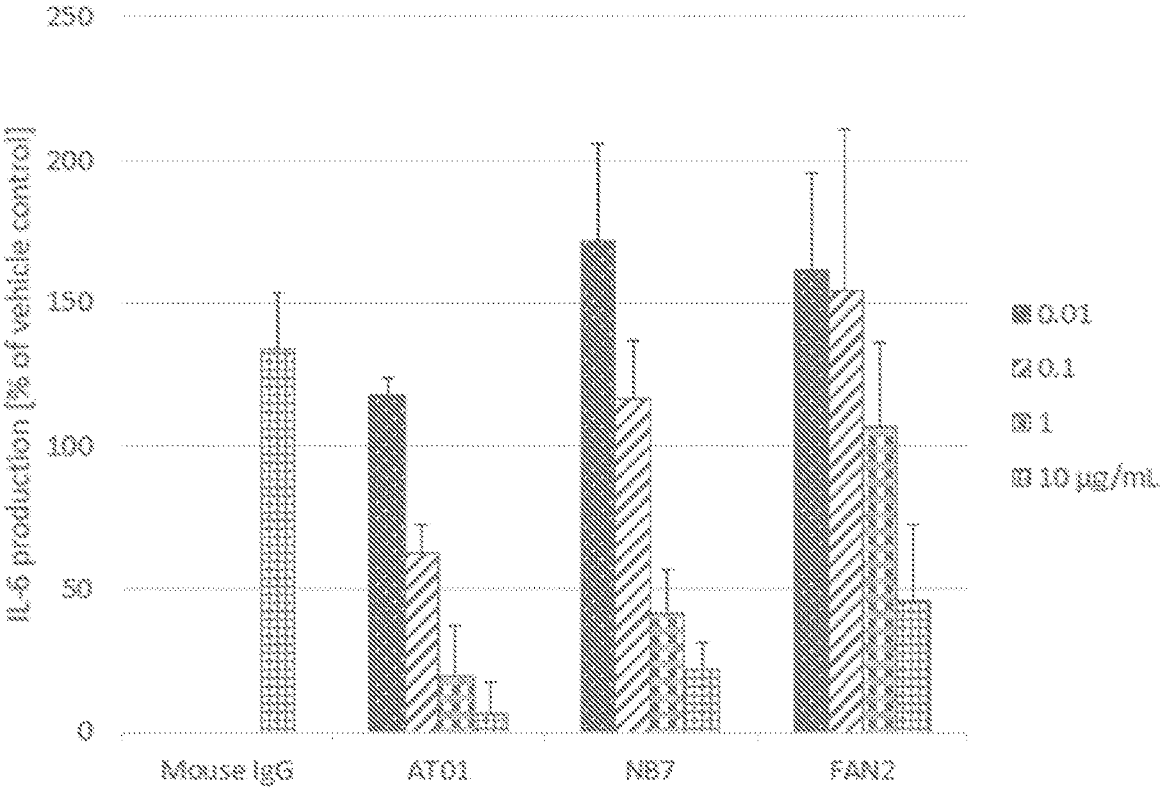
FIG. 6 is a graph showing that the AT01 antibody, the NB7 antibody, and the FAN2 antibody suppress the production of IL-6 from human peripheral blood mononuclear cells (which will be hereinafter referred to as PBMCs) treated with CL-264 in a concentration dependent manner.

In this description, the term "gene" includes not only DNA but also mRNA, cDNA, and cRNA.

In this description, the term "polynucleotide" is used in the same meaning as "nucleic acid" and also includes DNA, RNA, probes, oligonucleotides, and primers.

In this description, the terms "polypeptide" and "protein" are used without distinction.

In this description, the term "RNA fraction" means a fraction containing RNA.

In this description, the term "cells" includes cells in animal individuals and cultured cells.

In this description, the term "TLR7" is used to have the same meaning as TLR7 protein.

In this description, the term "antigen-binding fragment of an antibody" means a partial fragment of an antibody having binding activity to an antigen and includes Fab, $F(ab')_2$, Fv, scFv, diabodies, linear antibodies, multispecific antibodies formed from antibody fragments, and the like. Further, an antigen-binding fragment of an antibody also includes Fab' which is a monovalent fragment in a variable region of an antibody obtained by treating $F(ab')_2$ under reducing conditions. However, there is no limitation to these molecules as long as the fragment has an ability to bind to an antigen. Further, the antigen-binding fragment includes not only those obtained by treating a full-length molecule of an antibody protein with a suitable enzyme but also a protein produced in a suitable host cell using a genetically engineered antibody gene.

Complementarity determining regions (CDR: Complementarity Determining Regions) are known to be present at three points in each of the heavy and light chains of an antibody molecule. The complementarity determining regions, which are also called hypervariable regions, are present in the variable regions of the heavy and light chains of an antibody at sites where the variability of the primary structure is particularly high. In the primary structure of the polypeptide chain in each of the heavy and light chains, the complementarity determining regions are separately present at three points. Concerning the complementarity determining regions of an antibody, the complementarity determining regions of the heavy chain are expressed as CDRH1, CDRH2, and CDRH3 from the amino-terminal side of the heavy-chain amino acid sequence, and the complementarity determining regions of the light chain are expressed as CDRL1, CDRL2, and CDRL3 from the amino-terminal side of the light-chain amino acid sequence, in this description. These sites are adjacent to each other on the three-dimensional structure and determine the specificity for the antigen to be bound. Further, the amino chain sequence of each CDR is described according to the AbM definition (Martin, A. C. R., Cheetham, J. C. and Rees, A. R. (1989) Proc. Natl Acad. Sci. USA, 86, 9268-9272).

In the present invention, the phrase "hybridizing under stringent conditions" means hybridizing at 68° C. in a commercially available hybridization solution, ExpressHyb Hybridization Solution (Clontech Laboratories, Inc.) or hybridizing under conditions which allow hybridization at 68° C. in the presence of 0.7 to 1.0-M NaCl using a filter to which DNA is immobilized and subsequent identification by washing at 68° C. using an SSC solution of 0.1 to 2-fold concentration (SSC of 1-fold concentration composed of 150-mM NaCl and 15-mM sodium citrate) or conditions equivalent thereto.

1. TLR7

Human TLR7 used in the present invention can be directly purified from human B cells or dendritic cells or prepared by adjusting the cell membrane fractions of the aforementioned cells for use. Further, human TLR7 can be obtained by in-vitro synthesis or production in host cells by genetic engineering. In genetic engineering, human TLR7 is expressed specifically by being integrated into a vector capable of expressing human TLR7 cDNA, followed by synthesis in a solution containing enzymes, substrates, and energy substances that are necessary for transcription and translation, or human TLR7 is expressed by transformation of host cells of other prokaryotes or eukaryotes, so that such a protein can be obtained.

Likewise, monkey TLR7, mouse TLR7, and rat TLR7 can be directly purified from TLR7-expressing cells of monkeys, mice, and rats, respectively, and used, or prepared by adjusting the cell membrane fractions of the aforementioned cells for use. Further, monkey TLR7, mouse TLR7, and rat TLR7 can be obtained by in-vitro synthesis or production in host cells by genetic engineering.

The polynucleotide sequences encoding the amino acid sequences of human TLR7 (variant 1) and human TLR7 (variant 2) are set forth in SEQ ID NO: 1 and SEQ ID NO: 3, respectively in the Sequence Listing, and the amino acid sequences of human TLR7 (variant 1) and human TLR7 (variant 2) are set forth in SEQ ID NO: 2 and SEQ ID NO: 4, respectively in the Sequence Listing.

The cDNA of human TLR7 can be obtained, for example, by the so-called PCR method, with polymerase chain reaction (which will be hereinafter referred to as "PCR") (Saiki, R. K., et al., Science, (1988) 239, 487-49) using a cDNA library from an organ expressing the mRNA of human TLR7 as a template and a primer which specifically amplifies the cDNA of human TLR7.

The cDNA of human TLR7 also includes a polynucleotide which hybridizes with a polynucleotide consisting of a nucleotide sequence complementary to the nucleotide sequence encoding human TLR7 under stringent conditions and encodes a protein having a biological activity equivalent to human TLR7. Further, the cDNA of human TLR7 also includes a splicing variant transcribed from the human TLR7 gene locus or a polynucleotide which hybridizes with the splicing variant under stringent conditions and encodes a protein having a biological activity equivalent to human TLR7.

Further, human TLR7 also includes a protein which consists of the amino acid sequence of human TLR7 or the amino acid sequence excluding the signal sequence with one, two, three, four, or five amino acids substituted, deleted, or added and has a biological activity equivalent to human TLR7. Further, human TLR7 also includes a protein which consists of the amino acid sequence encoded by the splicing variant transcribed from the human TLR7 gene locus or the amino acid sequence with one, two, three, four, or five amino acids substituted, deleted, or added and has a biological activity equivalent to human TLR7.

The polynucleotide sequence encoding the amino acid sequence of monkey TLR7 is set forth in SEQ ID NO: 58 in the Sequence Listing, and the amino acid sequence of monkey TLR7 is set forth in SEQ ID NO: 85 in the Sequence Listing.

The cDNA of monkey TLR7 can be obtained, for example, by the PCR method using a cDNA library from an organ expressing the mRNA of monkey TLR7 as a template and a primer which specifically amplifies the cDNA of monkey TLR7.

The cDNA of monkey TLR7 also includes a polynucleotide which hybridizes with a polynucleotide consisting of a nucleotide sequence complementary to the nucleotide sequence encoding monkey TLR7 under stringent conditions and encodes a protein having a biological activity equivalent to monkey TLR7. Further, the cDNA of monkey TLR7 also includes a splicing variant transcribed from the monkey TLR7 gene locus or a polynucleotide which hybridizes with the splicing variant under stringent conditions and encodes a protein having a biological activity equivalent to monkey TLR7.

Further, monkey TLR7 also includes a protein which consists of the amino acid sequence of monkey TLR7 or the amino acid sequence excluding the signal sequence with one, two, three, four, or five amino acids substituted, deleted, or added and has a biological activity equivalent to monkey TLR7. Further, monkey TLR7 also includes a protein which consists of the amino acid sequence encoded by the splicing variant transcribed from the monkey TLR7 gene locus or the amino acid sequence with one, two, three, four, or five amino acids substituted, deleted, or added and has a biological activity equivalent to monkey TLR7.

The polynucleotide sequence encoding the amino acid sequence of monkey TLR7 is set forth in SEQ ID NO: 58 in the Sequence Listing, and the amino acid sequence of monkey TLR7 is set forth in SEQ ID NO: 85 in the Sequence Listing.

The cDNA of monkey TLR7 can be obtained, for example, by the PCR method using a cDNA library from an organ expressing the mRNA of monkey TLR7 as a template and a primer which specifically amplifies the cDNA of monkey TLR7.

The polynucleotide sequence encoding the amino acid sequence of mouse TLR7 is set forth in SEQ ID NO: 56 in the Sequence Listing, and the amino acid sequence of mouse TLR7 is set forth in SEQ ID NO: 83 in the Sequence Listing.

The cDNA of mouse TLR7 can be obtained, for example, by the PCR method using a cDNA library from an organ expressing the mRNA of mouse TLR7 as a template and a primer which specifically amplifies the cDNA of mouse TLR7.

The polynucleotide sequence encoding the amino acid sequence of rat TLR7 is set forth in SEQ ID NO: 57 in the Sequence Listing, and the amino acid sequence of rat TLR7 is set forth in SEQ ID NO: 84 in the Sequence Listing.

The cDNA of rat TLR7 can be obtained, for example, by the PCR method using a cDNA library from an organ expressing the mRNA of rat TLR7 as a template and a primer which specifically amplifies the cDNA of rat TLR7.

2. Anti-TLR7 Antibody and Production Thereof

The present invention provides an antibody or an antigen-binding fragment of the antibody having the properties of:

(a) specifically binding to human TLR7 or monkey TLR7 and not binding to mouse TLR7 or rat TLR7; and (b) inhibiting a function of the human TLR7 or the monkey TLR7.

The antibody or the antigen-binding fragment of the antibody of the present invention binds specifically to human TLR7 or monkey TLR7 and inhibits the functions thereof.

The binding activity of the antibody or the antigen-binding fragment of the antibody to TLR7 is evaluated by flow cytometry analysis according to a conventional method.

In this description, inhibiting a function of TLR7 means suppressing the production of IL-6 and/or type I interferon by TLR7-expressing cells. The activity of inhibiting a function of TLR7 is evaluated by incubating TLR7-expressing cells (for example, PBMCs) in vitro in the presence of the antibody or the antigen-binding fragment of the antibody and measuring the concentration of IL-6 or type I interferon in the culture supernatant.

In one embodiment of the present invention, the human TLR7 is a molecule consisting of the amino acid sequence set forth in SEQ ID NO: 2 or SEQ ID NO: 4, the monkey TLR7 is a molecule consisting of the amino acid sequence set forth in SEQ ID NO: 85, the mouse TLR7 is a molecule consisting of the amino acid sequence set forth in SEQ ID NO: 83, or the rat TLR7 is a molecule consisting of the amino acid sequence set forth in SEQ ID NO: 84. For example, the human TLR7 can be a molecule consisting of the amino acid sequence set forth in SEQ ID NO: 2 or SEQ ID NO: 4, the monkey TLR7 can be a molecule consisting of the amino acid sequence set forth in SEQ ID NO: 85, the mouse TLR7 can be a molecule consisting of the amino acid sequence set forth in SEQ ID NO: 83, and the rat TLR7 can be a molecule consisting of the amino acid sequence set forth in SEQ ID NO: 84, in the present invention.

For example, the antibody or the antigen-binding fragment of the antibody of the present invention can be an antibody against human TLR7 or an antigen-binding fragment of the antibody having the properties of:

(a) specifically binding to human TLR7 and not binding to mouse TLR7 and/or rat TLR7; and (b) inhibiting a function of human TLR7, wherein the human TLR7 is a molecule consisting of the amino acid sequence set forth in SEQ ID NO: 2 or SEQ ID NO: 4, the mouse TLR7 is a molecule consisting of the amino acid sequence set forth in SEQ ID NO: 83, and the rat TLR7 is a molecule consisting of the amino acid sequence set forth in SEQ ID NO: 84.

For example, the antibody or the antigen-binding fragment of the antibody of the present invention can be an antibody to monkey TLR7 or an antigen-binding fragment of the antibody having the properties of:

(a) specifically binding to monkey TLR7 and not binding to mouse TLR7 and/or rat TLR7; and (b) inhibiting a function of monkey TLR7, wherein the monkey TLR7 is a molecule consisting of the amino acid sequence set forth in SEQ ID NO: 85, the mouse TLR7 is a molecule consisting of the amino acid sequence set forth in SEQ ID NO: 83, and the rat TLR7 is a molecule consisting of the amino acid sequence set forth in SEQ ID NO: 84.

Hereinafter, the anti-TLR7 antibody of the present invention and a production method thereof are described with reference to the case of anti-human TLR7 antibody as an example. Anti-monkey TLR7 antibody also can be produced in the same manner as the production method of anti-human TLR7 antibody.

The antibody to human TLR7 of the present invention can be obtained by immunizing an animal with human TLR7 or any polypeptide selected from the amino acid sequence of human TLR7, and collecting and purifying the antibody produced in vivo, using conventional methods.

Human TLR7 serving as an antigen can be obtained by expressing a human TLR7 gene in a host cell by genetic engineering. Specifically, a vector capable of expressing the TLR7 gene may be prepared and introduced into a host cell to express the gene, and the TLR7 expressed may be purified.

The antibody to human TLR7 of the present invention can be obtained also by DNA immunization. The DNA immunization is a technique to induce immunity to an antigen by transfection of an antigen-expressing plasmid into an animal individual such as a mouse or a rat, thereby allowing the individual to express the antigen.

Examples of the transfection technique include a method of directly injecting the plasmid into a muscle, a method of injecting a conjugate of the plasmid with a liposome, polyethyleneimine, or the like into a vein, a technique using viral vectors, a technique of injecting gold particles with the plasmid attached using a Gene Gun, and a hydrodynamic method of rapidly injecting a large amount of a solution of the plasmid into a vein.

For improving the expression level in the transfection method by intramuscular injection of the expression plasmid, a technique of intramuscularly injecting the plasmid and thereafter applying electroporation to the same site (Aihara H, Miyazaki J. Nat Biotechnol. 1998 September; 16(9): 867-70 or Mir L M, Bureau M F, Gehl J, Rangara R, Rouy D, Caillaud J M, Delaere P, Branellec D, Schwartz B, Scherman D. Proc Natl Acad Sci USA. 1999 Apr. 13; 96(8): 4262-7) is known as in-vivo electroporation. In this technique, the expression level is further improved by treating a muscle with hyaluronidase before intramuscular injection of the plasmid (McMahon J M, Signori E, Wells K E, Fazio V M, Wells D J. Gene Ther. 2001 August; 8(16): 1264-70).

Further, a monoclonal antibody can also be obtained, according to a known method (for example, Kohler and Milstein, Nature (1975) 256, p. 495-497, Kennet, R. ed., Monoclonal Antibodies, p. 365-367, Plenum Press, N.Y. (1980)), by fusing an antibody-producing cell which produces an antibody to TLR7 with a myeloma cell to establish a hybridoma. Specific examples of such a method include those described in International publication No. WO 09/48072 (published on Apr. 16, 2009) and International publication No. WO 10/117011 (published on Oct. 14, 2010).

Examples of the mouse anti-human TLR7 antibody established as above can include the AT01 antibody, the NB7 antibody, and the FAN2 antibody.

The amino acid sequence of the heavy-chain variable region of the AT01 antibody is set forth in SEQ ID NO: 5 in the Sequence Listing, and the polynucleotide sequence encoding the amino acid sequence is set forth in SEQ ID NO: 6 in the Sequence Listing. The amino acid sequence of the heavy-chain variable region of the NB7 antibody is set forth in SEQ ID NO: 7 in the Sequence Listing, and the polynucleotide sequence encoding the amino acid sequence is set forth in SEQ ID NO: 8 in the Sequence Listing. The amino acid sequence of the heavy-chain variable region of the FAN2 antibody is set forth in SEQ ID NO: 9 in the Sequence Listing, and the polynucleotide sequence encoding the amino acid sequence is set forth in SEQ ID NO: 10 in the Sequence Listing.

Further, the amino acid sequence of the light-chain variable region of the AT01 antibody is set forth in SEQ ID NO: 11 in the Sequence Listing, and the polynucleotide sequence encoding the amino acid sequence is set forth in SEQ ID NO: 12 in the Sequence Listing. The amino acid sequence of the light-chain variable region of the NB7 antibody is set forth in SEQ ID NO: 13 in the Sequence Listing, and the polynucleotide sequence encoding the amino acid sequence is set forth in SEQ ID NO: 14 in the Sequence Listing. The amino acid sequence of the light-chain variable region of the FAN2 antibody is set forth in SEQ ID NO: 15 in the Sequence Listing, and the polynucleotide sequence encoding the amino acid sequence is set forth in SEQ ID NO: 16 in the Sequence Listing.

The heavy-chain variable region of the AT01 antibody comprises CDRH1 consisting of the amino acid sequence set forth in SEQ ID NO: 17 (GYTFTNNWLH), CDRH2 consisting of the amino acid sequence set forth in SEQ ID NO: 18 (DIYPSNGRTN), and CDRH3 consisting of the amino acid sequence set forth in SEQ ID NO: 19 (ERGYFDY). Further, the light-chain variable region of the antibody comprises CDRL1 consisting of the amino acid sequence set forth in SEQ ID NO: 20 (KASQDINKYIA), CDRL2 consisting of the amino acid sequence set forth in SEQ ID NO: 21 (YTSTLQP), and CDRL3 consisting of the amino acid sequence set forth in SEQ ID NO: 22 (LQYDYLLT). The amino acid sequences of the aforementioned CDRs are shown also in FIG. 24-1.

The heavy-chain variable region of the NB7 antibody comprises CDRH1 consisting of the amino acid sequence set forth in SEQ ID NO: 23 (GYSITSDYAWN), CDRH2 consisting of the amino acid sequence set forth in SEQ ID NO: 24 (HISYRGNTN), and CDRH3 consisting of the amino acid sequence set forth in SEQ ID NO: 25 (WNYYGYVDYAMDY). Further, the light-chain variable region of the antibody comprises CDRL1 consisting of the amino acid sequence set forth in SEQ ID NO: 26 (RASQDISNYLN), CDRL2 consisting of the amino acid sequence set forth in SEQ ID NO: 27 (YTSRLHS), and CDRL3 consisting of the amino acid sequence set forth in SEQ ID NO: 28 (QQGDTFPT). The amino acid sequences of the aforementioned CDRs are shown also in FIG. 24-2.

The heavy-chain variable region of the FAN2 antibody comprises CDRH1 consisting of the amino acid sequence set forth in SEQ ID NO: 29 (GFSLTGYGVN), CDRH2 consisting of the amino acid sequence set forth in SEQ ID NO: 30 (MIWGDGSTD), and CDRH3 consisting of the amino acid sequence set forth in SEQ ID NO: 31 (DKGYDGYYYAMDY). Further, the light-chain variable region of the antibody comprises CDRL1 consisting of the amino acid sequence set forth in SEQ ID NO: 32 (RASENIYSYLA), CDRL2 consisting of the amino acid sequence set forth in SEQ ID NO: 33 (DAKTLAE), and CDRL3 consisting of the amino acid sequence set forth in SEQ ID NO: 34 (QHHYGIPYT). The amino acid sequences of the aforementioned CDRs are shown also in FIG. 24-3.

In one embodiment, the antibody or the antigen-binding fragment of the antibody of the present invention can have a competitive inhibitory activity for binding to the human TLR7 with an antibody comprising the amino acid sequences of the heavy-chain variable region and the light-chain variable region of the AT01 antibody, the NB7 antibody or the FAN2 antibody.

In another embodiment, the antibody or the antigen-binding fragment of the antibody of the present invention can be an antibody or an antigen-binding fragment of the antibody comprising CDRH1 to CDRH3 of the AT01 antibody as complementarity determining regions in the heavy chain and CDRL1 to CDRL3 of the AT01 antibody as complementarity determining regions in the light chain, an antibody or an antigen-binding fragment of the antibody comprising CDRH1 to CDRH3 of the NB7 antibody as complementarity determining regions in the heavy chain and CDRL1 to CDRL3 of the NB7 antibody as complementarity determining regions in the light chain, or an antibody or an antigen-binding fragment of the antibody comprising CDRH1 to CDRH3 of the FAN2 antibody as complementarity determining regions in the heavy chain and CDRL1 to CDRL3 of the FAN2 antibody as complementarity determining regions in the light chain. In a preferred aspect, the antibody or the antigen-binding fragment of the antibody of the present invention can be an antibody or an antigen-binding fragment of the antibody comprising CDRH1 to CDRH3 of the AT01 antibody as complementarity determining regions in the heavy chain and CDRL1 to CDRL3 of the AT01 antibody as complementarity determining regions in the light chain.

In still another embodiment, the antibody or the antigen-binding fragment of the antibody of the present invention can be an antibody comprising the sequences of the heavy-chain variable region and the light-chain variable region of the AT01 antibody, the NB7 antibody or the FAN2 antibody.

The antibody of the present invention includes recombinant antibodies artificially modified for the purpose of reducing the heteroantigenicity to humans and the like, such as chimeric antibodies, humanized antibodies, and human antibodies, in addition to the aforementioned monoclonal antibodies to human TLR7. These antibodies can be produced using known methods.

Examples of the chimeric antibodies can include an antibody in which the variable region and the constant region of the antibody are heterogeneous to each other, such as a chimeric antibody with a variable region of a mouse- or rat-derived antibody joined to a human-derived constant region (see Proc. Natl. Acad. Sci. U.S.A, 81, 6851-6855, (1984)). Examples of the mouse anti-human TLR7 antibody (AT01 antibody)-derived chimeric antibody can include an antibody consisting of a heavy chain comprising a heavy-chain variable region consisting of the amino acid sequence of SEQ ID NO: 5 and a light chain comprising a light-chain variable region consisting of the amino acid sequence of SEQ ID NO: 11. Examples of the AT01 antibody-derived chimeric antibody can include an antibody consisting of a heavy chain consisting of the amino acid sequence at positions 20 to 465 in SEQ ID NO: 35 and a light chain consisting of an amino acid sequence at positions 21 to 233 in SEQ ID NO: 36. In this description, such an antibody is referred to as "cAT01" or "cAT01 antibody".

Further, examples of the mouse anti-human TLR7 antibody (NB7 antibody)-derived chimeric antibody can include an antibody consisting of a heavy chain comprising a heavy-chain variable region consisting of the amino acid sequence of SEQ ID NO: 7 and a light chain comprising a light-chain variable region consisting of the amino acid sequence of SEQ ID NO: 13. Examples of the NB7 antibody-derived chimeric antibody can include an antibody consisting of a heavy chain consisting of an amino acid sequence at positions 20 to 471 in SEQ ID NO: 37 and a light chain consisting of an amino acid sequence at positions 21 to 233 in SEQ ID NO: 38. In this description, such an antibody is referred to as "cNB7" or "cNB7 antibody".

Further, examples of the mouse anti-human TLR7 antibody (FAN2 antibody)-derived chimeric antibody can include an antibody consisting of a heavy chain comprising a heavy-chain variable region consisting of the amino acid sequence of SEQ ID NO: 9 and a light chain comprising a light-chain variable region consisting of the amino acid sequence of SEQ ID NO: 15. Examples of the FAN2 antibody-derived chimeric antibody can include an antibody consisting of a heavy chain consisting of an amino acid sequence at positions 20 to 470 in SEQ ID NO: 39 and a light chain consisting of an amino acid sequence at positions 21 to 234 in SEQ ID NO: 40. In this description, such an antibody is referred to as "cFAN2" or "cFAN2 antibody".

Humanized antibodies that are recombinant antibodies can be produced by artificially modifying the sequences of the aforementioned chimeric antibodies to human TLR7 for the purpose of reducing the heteroantigenicity to humans and the like. Further, the antibody of the present invention includes antibodies with modified CDRs of the humanized antibodies. These antibodies can be produced using known methods.

Examples of the humanized antibodies can include an antibody with only the CDRs integrated into a human-derived antibody (see Nature (1986) 321, p. 522-525), and an antibody with not only the sequences of CDRs but also the amino acid residues of some parts of the framework grafted into a human antibody (International publication No. WO 90/07861).

For example, humanized antibodies derived from the cAT01 antibody and the cNB7 antibody retain all of the 6 CDR sequences derived from cAT01 or cNB7 and have the activity of inhibiting a function of human TLR7.

Suitable cases of the aforementioned humanized antibodies can include cAT01 antibody-derived humanized antibodies (huAT01 antibodies) such as: an antibody consisting of a heavy chain comprising a heavy-chain variable region consisting of the amino acid sequence set forth in SEQ ID NO: 41 and a light chain comprising a light-chain variable region consisting of the amino acid sequence set forth in SEQ ID NO: 43; an antibody consisting of a heavy chain comprising a heavy-chain variable region consisting of the amino acid sequence set forth in SEQ ID NO: 41 and a light chain comprising a light-chain variable region consisting of the amino acid sequence set forth in SEQ ID NO: 44; an antibody consisting of a heavy chain comprising a heavy-chain variable region consisting of the amino acid sequence set forth in SEQ ID NO: 42 and a light chain comprising a light-chain variable region consisting of the amino acid sequence set forth in SEQ ID NO: 43; and an antibody consisting of a heavy chain comprising a heavy-chain variable region consisting of the amino acid sequence set forth in SEQ ID NO: 42 and a light chain comprising a light-chain variable region consisting of the amino acid sequence set forth in SEQ ID NO: 44.

Further, an antibody having an activity equivalent to the aforementioned huAT01 antibodies can be selected by combining sequences exhibiting high homology with the amino acid sequence of the heavy-chain variable region and the amino acid sequence of the light-chain variable region of the aforementioned huAT01 antibodies respectively. The homology is generally a homology of 80% or more, preferably a homology of 90% or more, more preferably a homology of 95% or more, most preferably a homology of 99% or more (however, the CDRs are the same as in the aforementioned antibodies). Further, an antibody having an activity equivalent to the aforementioned antibodies can also be selected by combining an amino acid sequence with one to several (for example, 2, 3, 4, 5, 6, 7, 8, 9, or 10) amino acid residues substituted, deleted, or added in the amino acid sequence of the heavy-chain variable region or the light-chain variable region (however, excluding the CDR sites).

Further suitable cases can include: an antibody consisting of a heavy chain consisting of the amino acid sequence at positions 20 to 465 in the amino acid sequence set forth in SEQ ID NO: 45 and a light chain consisting of the amino acid sequence at positions 21 to 233 in the amino acid sequence set forth in SEQ ID NO: 48; an antibody consisting of a heavy chain consisting of the amino acid sequence at positions 20 to 465 in the amino acid sequence set forth in SEQ ID NO: 45 and a light chain consisting of the amino acid sequence at positions 21 to 233 in the amino acid sequence set forth in SEQ ID NO: 49; an antibody consisting of a heavy chain consisting of the amino acid sequence at positions 20 to 465 in the amino acid sequence set forth in SEQ ID NO: 46 and a light chain consisting of the amino acid sequence at positions 21 to 233 in the amino acid sequence set forth in SEQ ID NO: 48; an antibody consisting of a heavy chain consisting of the amino acid sequence at positions 20 to 465 in the amino acid sequence set forth in SEQ ID NO: 46 and a light chain consisting of the amino acid sequence at positions 21 to 233 in the amino acid sequence set forth in SEQ ID NO: 49; an antibody consisting of a heavy chain consisting of the amino acid sequence at positions 20 to 462 in the amino acid sequence set forth in SEQ ID NO: 47 and a light chain consisting of the amino acid sequence at positions 21 to 233 in the amino acid sequence set forth in SEQ ID NO: 48; or an antibody consisting of a heavy chain consisting of the amino acid sequence at positions 20 to 462 in the amino acid sequence set forth in SEQ ID NO: 47 and a light chain consisting of the amino acid sequence at positions 21 to 233 in the amino acid sequence set forth in SEQ ID NO: 49.

Further, examples of the cNB7 antibody-derived humanized antibody (huNB7 antibody) can include an antibody consisting of a heavy chain comprising a heavy-chain variable region consisting of the amino acid sequence of SEQ ID NO: 50 and a light chain comprising a light-chain variable region consisting of the amino acid sequence of SEQ ID NO: 51.

Further, an antibody having an activity equivalent to the aforementioned huNB7 antibody can be selected by combining sequences exhibiting high homology with the amino acid sequence of the heavy-chain variable region and the amino acid sequence of the light-chain variable region of the aforementioned huNB7 antibody. The homology is generally a homology of 80% or more, preferably a homology of 90% or more, more preferably a homology of 95% or more, most preferably a homology of 99% or more (however, the CDRs are the same as in the aforementioned antibodies). Further, an antibody having an activity equivalent to the aforementioned antibody can also be selected by combining an amino acid sequence with one to several (for example, 2, 3, 4, 5, 6, 7, 8, 9, or 10) amino acid residues substituted, deleted, or added in the amino acid sequence of the heavy-chain variable region or the light-chain variable region (however, excluding the CDR sites).

Further suitable cases can include: an antibody consisting of a heavy chain consisting of the amino acid sequence at positions 20 to 471 in the amino acid sequence set forth in SEQ ID NO: 52 and a light chain consisting of the amino acid sequence at positions 21 to 233 in the amino acid sequence set forth in SEQ ID NO: 53; or an antibody consisting of a heavy chain consisting of the amino acid sequence at positions 20 to 468 in the amino acid sequence set forth in SEQ ID NO: 54 and a light chain consisting of the amino acid sequence at positions 21 to 233 in the amino acid sequence set forth in SEQ ID NO: 53.

The antibody of the present invention may be obtained by introducing further mutation into the aforementioned humanized antibodies to change the binding ability with respect to human TLR7. Such a technique is called affinity maturation, and specific examples thereof can include the ribosome display method. The ribosome display method is a method of isolating a gene sequence of a protein which binds to a target molecule, using a tripartite complex in which the protein and mRNA carrying the genetic information of the protein are bound together via ribosomes (Stafford R L. et. al. Protein Eng. Des. Sel. 2014 (4): 97-109).

In order to avoid injuring normal human TLR7-expressing cells, the antibody desirably has low effector activity. The effector activity is known to differ depending on the subclass of the antibody. For example, a feature of IgG4 is that it has low ADCC and CDC activities, and a feature of IgG2 is that it has CDC activity while having low ADCC activity. Based on such features, an antibody with reduced ADCC and CDC activities can be produced by substituting the constant region of IgG1 with the constant region of IgG2 or IgG4. Further, an IgG1 antibody with reduced ADCC and CDC activities can be produced by partially substituting the sequence of the constant region of IgG1 with reference to IgG2 or IgG4. As an example, Marjan Hezareh et. al. Journal of Virology, 75 (24): 12161-12168 (2001) shows that the ADCC and CDC activities are reduced by substituting leucine residues 234 and 235 (the numerals represent EU indices by Kabat et. al.) of IgG1 respectively with alanine residues.

The present invention includes modified forms of the antibody or the antigen-binding fragment of the antibody. The modified forms mean those formed by chemically or biologically modifying the antibody or the antigen-binding fragment of the antibody of the present invention. The chemically modified forms include chemically modified forms of carbohydrate chains by attachment of a chemical moiety to the amino acid backbone, N-linkage, or O-linkage. The biologically modified forms include those modified after translation (for example, by glycosylation to N-linkage or O-linkage, N-terminal or C-terminal processing, deamidation, isomerization of aspartic acid, and oxidation of methionine), and those with a methionine residue added at the N-terminal by expression using prokaryote host cells. Further, the meaning of the modified products also includes those labeled for enabling detection or isolation of the antibody of the present invention or antigen, such as enzyme-labeled bodies, fluorescence-labeled bodies, and affinity-labeled bodies. Such modified products of the antibody or the antigen-binding fragment of the antibody of the present invention are useful for improving the stability and the blood retention of the original antibody of the present invention, reducing the antigenicity, and detecting or isolating the antibody or antigen.

It is known that a lysine residue at the carboxyl terminus of the heavy chain of antibodies produced in cultured mammalian cells is deleted (Journal of Chromatography A, 705: 129-134 (1995)). Further, it is also known that two amino acid residues, glycine and lysine, at the carboxyl terminus of the same heavy chain are deleted, and a proline residue newly located at the carboxyl terminus is amidated (Analytical Biochemistry, 360: 75-83 (2007)).

However, such deletions and modifications of the heavy-chain sequence have no influence on the antigen-binding ability and the effector functions (such as complement activation and antibody-dependent cellular cytotoxicity) of the antibody.

Accordingly, examples of modified forms of the antibody and the antigen-binding fragment of the antibody of the present invention can include: deletion variants with one or two amino acids deleted at the carboxyl terminus of the heavy chain; and amidated deletion variants (such as a heavy chain with an amidated proline residue at the carboxyl terminal part). However, the deletion variants at the carboxyl terminus of the heavy chain of the antibody according to the present invention are not limited to the aforementioned types, as long as the antigen-binding ability and the effector functions are maintained.

Two heavy chains constituting the antibody according to the present invention may be a combination of any one or two types of heavy chains selected from the group consisting of the full length and the aforementioned deletion variants. The quantitative ratio of the deletion variants can be affected by the type of cultured mammalian cells and culture conditions for producing the antibody according to the present invention, but examples of the main component of the antibody according to the present invention can include a component with one amino acid residue deleted at the carboxyl terminus in each of the two heavy chains. That is, heavy chains consisting of amino acid sequences with one or two amino acids deleted at the carboxyl terminus of each heavy-chain sequence represented by an amino acid sequence at positions 20 to 465 in SEQ ID NO: 35, an amino acid sequence at positions 20 to 471 in SEQ ID NO: 37, an amino acid sequence at positions 20 to 470 in SEQ ID NO: 39, an amino acid sequence at positions 20 to 465 in SEQ ID NO: 45, an amino acid sequence at positions 20 to 465 in SEQ ID NO: 46, an amino acid sequence at positions 20 to 462 in SEQ ID NO: 47, an amino acid sequence at positions 20 to 471 in SEQ ID NO: 52, and an amino acid sequence at positions 20 to 468 in SEQ ID NO: 54, in the Sequence Listing can also be used for the antibody of the present invention.

The antibodies obtained by the aforementioned methods are evaluated for their binding property with respect to an antigen, so that a suitable antibody can be selected therefrom. Another indicator for comparing the properties of the antibodies can be the stability of the antibodies, for example. Differential scanning calorimetry (DSC) is a method that enables quick and accurate measurement of the thermal denaturation midpoint (Tm), which is a good indicator of the relative structural stability of proteins. The differences in thermostability can be compared by measuring the Tm values using DSC and comparing the values. It is known that the storage stability of antibodies shows some correlation with the thermostability of antibodies (Lori Burton, et. al., Pharmaceutical Development and Technology (2007) 12, p. 265-273), and a suitable antibody can be selected using the thermostability as an indicator. Examples of other indicators for selecting an antibody can include high yield in a suitable host cell and low aggregability in an aqueous solution. Since the antibody, for example, with the highest yield does not necessarily show the highest thermostability, comprehensive determination needs to be made based on the aforementioned indicators to select an antibody that is most suitable for administration to humans.

Further, a method of obtaining a single-chain immunoglobulin by linking the full-length sequences of the heavy and light chains of an antibody using a suitable linker is also known (Lee, H-S, et. al., Molecular Immunology (1999) 36, p. 61-71; Schirrmann, T. et. al., mAbs (2010), 2, (1) p. 73-76). Such a single-chain immunoglobulin is dimerized and thus can maintain a structure and an activity that are similar to those of an antibody that was originally a tetramer. Further, the antibody of the present invention may be an antibody comprising a single heavy-chain variable region and no light-chain sequences. Such an antibody is called a single domain antibody (sdAb) or nanobody and is reported to be actually observed in camels or llamas and maintain antigen-binding ability (Muyldermans S. et. al., Protein Eng. (1994) 7 (9), 1129-35, Hamers-Casterman C. et. al., Nature (1993) 363 (6428) 446-8). The aforementioned antibody can also be understood to be a kind of antigen-binding fragment of the antibody of the present invention.

Further, the antibody-dependent cellular cytotoxicity can be enhanced by adjusting the glycosylation bound to the antibody of the present invention. International publication No. WO 99/54342, International publication No. WO 00/61739, International publication No. WO 02/31140, International publication No. WO 2007/133855, International publication No. WO 2013/120066, and the like are known as techniques for adjusting glycosylation of antibodies, but there is no limitation to these.

In the case of producing an antibody by isolating an antibody gene once and thereafter introducing it into a suitable host cell, a combination of such a suitable host cell and an expression vector can be used.

Specific examples of the antibody gene can include a combination of a gene encoding the heavy-chain sequence and a gene encoding the light-chain sequence of the antibodies in this specification. More specifically, examples of the antibody gene can include a combination of a polynucleotide comprising a polynucleotide sequence encoding the antibody or the antigen-binding fragment of the antibody of the present invention, a polynucleotide comprising a polynucleotide sequence encoding the amino acid sequence of the heavy-chain variable region of the antibody or the antigen-binding fragment of the antibody of the present invention, and a polynucleotide comprising a polynucleotide sequence encoding the amino acid sequence of the light-chain variable region of the antibody or the antigen-binding fragment of the antibody of the present invention. The heavy-chain sequence gene constituting the antibody gene also includes a polynucleotide comprising a polynucleotide sequence of a polynucleotide which hybridizes with a polynucleotide consisting of a polynucleotide sequence complementary to the aforementioned polynucleotide sequence encoding the heavy-chain variable region under stringent conditions. Further, the light-chain sequence gene constituting the antibody gene also includes a polynucleotide comprising a polynucleotide sequence of a polynucleotide which hybridizes with a polynucleotide consisting of a polynucleotide sequence complementary to the aforementioned polynucleotide sequence encoding the light-chain variable region under stringent conditions.

When transforming the host cell, the heavy-chain sequence gene and the light-chain sequence gene can be inserted in the same expression vector or in separate expression vectors. In the case of using a eukaryotic cell as a host cell, animal cells, plant cells, and eukaryotic microorganisms can be used. Examples of the animal cells can include (1) mammalian cells such as COS cells (Gluzman, Y. Cell (1981) 23, p. 175-182, ATCC CRL-1650) which are monkey cells, and dihydrofolate reductase enzyme-deficient strains (Urlaub, G. and Chasin, L. A. Proc. Natl. Acad. Sci. U.S.A (1980) 77, p. 4126-4220) of mouse fibroblasts NIH3T3 (ATCC No. CRL-1658) and Chinese hamster ovary cells (CHO cells, ATCC CCL-61). Further, in the case of using prokaryotic cells, examples can include *Escherichia coli* and *Bacillus subtilis*. An antibody is obtained by introducing a target antibody gene into such a cell by transformation and culturing the transformed cell in vitro. Since the yield may differ depending on the sequence of the antibody in the aforementioned culture method, those easily produced as pharmaceuticals can be selected from amongst antibodies having the same binding activity using the yield as an indicator.

There is no limitation on the isotype of the antibody of the present invention, and examples thereof can include IgG (IgG1, IgG2, IgG3, and IgG4), IgM, IgA (IgAQ1 and IgA2), IgD, or IgE, preferably IgG or IgM, further preferably IgG1 or IgG4.

Further, the antibody of the present invention may be an antigen-binding fragment of an antibody comprising an antigen-binding site of the antibody or a modified product thereof. A fragment of the antibody can be obtained by treating the antibody with a protease such as papain and pepsin or modifying the antibody gene with a genetically engineered technique to allow expression in a suitable cultured cell. Among such antibody fragments, fragments maintaining all or part of the functions of the full-length molecules of the antibody can be called antigen-binding fragments of the antibody.

Examples of the functions of antibodies can generally include antigen-binding activity, the activity of neutralizing antigen activity, the activity of enhancing antigen activity, antibody-dependent cytotoxicity, complement-dependent cytotoxicity, and complement-dependent cellular cytotoxicity. The function of the antigen-binding fragment of the antibody in the present invention is binding activity to human TLR7, preferably the activity of inhibiting a function of human TLR7, more preferably the activity of suppressing production of IL-6 and/or type I interferon by TLR7-expressing cells.

Examples of the fragment of the antibody can include Fab, $F(ab')_2$, Fv, or single-chain Fv (scFv) obtained by linking heavy- and light-chain Fvs with a suitable linker, diabodies, linear antibodies, and multispecific antibodies formed from antibody fragments. Further, the fragment of the antibody also includes a monovalent Fab' fragment in a variable region of the antibody obtained by treating $F(ab')_2$ under reduced conditions.

Further, the antibody of the present invention may be a multispecific antibody having specificity to at least two types of different antigens. In general, such a molecule binds to two types of antigens (that is, a bispecific antibody), but the "multispecific antibody" in the present invention includes antibodies having specificity to more (for example, three types of) antigens.

The multispecific antibody of the present invention may be an antibody consisting of the full-length or a fragment of such an antibody (for example, $F(ab')_2$ bispecific antibody). The bispecific antibody can be produced also by binding the heavy and light chains (HL pairs) of two types of antibodies to each other or producing a bispecific antibody-producing fusion cell by fusing hybridomas which produce different monoclonal antibodies (Millstein et al., Nature (1983) 305, p. 537-539).

The antibody of the present invention may also be a single-chain antibody (which may be referred to also as scFv). The single-chain antibody can be obtained by linking the heavy-chain variable region and the light-chain variable region of an antibody by a polypeptide linker (Pluckthun, The Pharmacology of Monoclonal Antibodies, 113 (edited by Rosenberg and Moore), Springer Verlag, New York, p. 269-315 (1994), Nature Biotechnology (2005), 23, p. 1126-1136). Further, a BiscFv fragment produced by binding two scFvs with a polypeptide linker can also be used as a bispecific antibody.

Methods for producing single-chain antibodies are known in this technical field (for example, see U.S. Pat. Nos. 4,946,778, 5,260,203, 5,091,513, and 5,455,030). In such a scFv, the heavy-chain variable region and the light-chain variable region are linked via a linker which does not produce conjugates, preferably a polypeptide linker (Huston, J. S. et al., Proc. Natl. Acad. Sci. U.S.A. (1988), 85, p. 5879-5883). The heavy-chain variable region and the light-chain variable region in the scFv may be derived from the same antibody or separate antibodies. Any single-chain peptide consisting of 12 to 19 residues is, for example, used as the polypeptide linker which links the variable regions.

DNA encoding the scFv is obtained by PCR amplification using a DNA element encoding the whole or a desired part of the amino acid sequence of DNA encoding the heavy chain or the heavy-chain variable region of the antibody and DNA encoding the light chain or the light-chain variable region thereof as a template and a primer pair defining both ends thereof, and further amplification by combining DNA encoding a polypeptide linker portion and a primer pair defining both ends thereof so as to be linked respectively with the heavy chain and the light chain.

Further, once DNA encoding the scFv is produced, an expression vector containing the DNA and a host cell transformed by the expression vector can be obtained according to conventional methods. Further, the scFv can be obtained using the host cell according to a conventional method. Such an antibody fragment can be produced by obtaining and expressing a gene thereof in a host cell as described above.

The antibody of the present invention may be an antibody multimerized to increase the affinity for the antigen. The antibody to be multimerized may be one antibody or a plurality of antibodies which recognize a plurality of epitopes of the same antigen. Examples of the method for multimerizing the antibody can include binding of an IgG CH3 domain to two scFvs, binding to streptavidin, and introduction of a helix-turn-helix motif.

The antibody of the present invention may be a polyclonal antibody which is a mixture of a plurality of types of anti-human TLR7 antibodies comprising different amino acid sequences. As an example of the polyclonal antibody, there is a mixture of a plurality of types of antibodies comprising different CDRs. As such a polyclonal antibody, an antibody purified from a culture obtained by culturing a mixture of cells which produce different antibodies can be used (see International publication No. WO 2004/061104).

As a modified product of the antibody, an antibody bound to various molecules such as polyethylene glycol (PEG) can also be used.

The antibody of the present invention may further be an immunoconjugate formed by such an antibody and another drug. Examples of the antibody can include the antibody bound to a radioactive substance or a compound having a pharmacological action (Nature Biotechnology (2005) 23, p. 1137-1146).

The antibody obtained can be purified to homogeneity. For separating and purifying the antibody, common separation and purification methods used for proteins may be used. For example, the antibody can be separated and purified by appropriately selecting and combining column chromatography, filter filtration, ultrafiltration, salting-out, dialysis, preparative polyacrylamide gel electrophoresis, isoelectric focusing, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but there is no limitation to these.

Examples of the chromatography can include affinity chromatography, ion exchange chromatography, hydrophobic chromatography, gel filtration chromatography, reverse-phase chromatography, and adsorption chromatography. Such chromatography can be performed using liquid chromatography such as HPLC and FPLC. Examples of the column used for the affinity chromatography can include a protein A column and a protein G column. Examples of a column which is a protein A column can include Hyper D, POROS, Sepharose F. F. (pharmacia). Further, the antibody can also be purified, using a carrier with an immobilized antigen, by utilizing the binding property to the antigen.

3. Pharmaceutical Containing Anti-Human TLR7 Antibody

Antibodies that inhibit a function of human TLR7 can be obtained from the anti-human TLR7 antibodies obtained by the methods disclosed in "2. Anti-TLR7 antibody and production thereof" above. These antibodies that inhibit a function of human TLR7 can inhibit the biological activity of human TLR7 in vivo, that is, activation of human TLR7-expressing cells typified by blood cells by human TLR7 ligands, and therefore can be used as pharmaceuticals such as agents for treating and/or preventing diseases caused by a function of human TLR7.

The diseases and conditions caused by a function of human TLR7 can include immune inflammation-related diseases, allergic diseases, infections, or cancers.

Examples of the immune inflammation-related diseases can include diseases of the connective tissue and the musculoskeletal system (such as systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease, and muscular dystrophy), the blood system (such as autoimmune hemolytic anemia, aplastic anemia, and idiopathic thrombocytopenic purpura), the digestive tract system (such as Crohn's disease, ulcerative colitis, and ileitis), the hepatobiliary pancreatic system and the endocrine system (such as autoimmune hepatitis, viral hepatitis, alcoholic hepatitis, nonalcoholic steatohepatitis, primary sclerosing cholangitis, primary biliary cirrhosis, Sjogren's syndrome, type 1 diabetes, autoimmune thyroiditis, Graves' disease, and Hashimoto's thyroiditis), the respiratory system (such as chronic obstructive pulmonary disease, cystic fibrosis, and interstitial pneumonia), the cranial nervous system (such as multiple sclerosis, myasthenia gravis, meningitis, encephalomyelitis, and autoimmune encephalitis), the visual system (such as uveitis, trachoma, and endophthalmitis), the cardiovascular system (such as vasculitis syndrome, polyangiitis granulomatosis Wegener's granulomatosis, myocarditis, ischemic heart disease, and atherosclerosis), the skin epidermis system (such as psoriasis, pemphigus, vitiligo, contact dermatitis, and eczema), the renal system (such as glomerulonephritis, diabetic nephropathy, IgA nephropathy, purpura nephritis, nephrosis, and interstitial cystitis), and the endocrine system (such as type 1 diabetes, autoimmune thyroiditis, Graves' disease, and Hashimoto's thyroiditis), and systemic inflammation (such as Behcet's disease, antiphospholipid antibody syndrome, IgG4-related diseases, sepsis, hemorrhage, hypersensitivity, transplantation rejection, and shock symptoms caused by, for example, cancer chemotherapy).

Examples of the allergic diseases can include atopic dermatitis, asthma, anaphylaxis, anaphylactoid reactions, food allergy, rhinitis, otitis media, drug reactions, insect sting reactions, plant reactions, latex allergy, conjunctivitis, and urticaria.

Examples of the infections can include diseases caused by infections by viruses (such as a single-stranded RNA virus, a double-stranded RNA virus, a single-stranded DNA virus, and a double-stranded DNA virus), bacteria (such as gram-negative bacteria, gram-positive bacteria, acid-fast bacteria, actinomycetes, spirochetes, spiral bacteria, *Rickettsia, Chlamydia*, and *Mycoplasma*), fungi (such as *Trichophyton, Candida, Cryptococcus, Aspergillus, Pneumocystis*, and *Malassezia*), and parasites (such as filariae, trematodes, cestodes, *Distoma, Echinococcus, Entamoeba histolytica*, fleas, lice, mites, Ascaridida, and Oxyuridae).

Examples of the cancer treatment can include treatments for lymphoma, leukemia, breast cancer, lung cancer, and skin cancer.

Examples of the anti-human TLR7 antibodies as pharmaceuticals can include chimeric antibodies and humanized antibodies, which are produced from the AT01 antibody and/or the NB7 antibody, and CDR modified forms thereof.

The inhibitory activity against a function of human TLR7 by the anti-human TLR7 antibodies in vitro can be measured, for example, based on the activity of suppressing the activation of blood cells expressing human TLR7. For example, the activity of suppressing IL-6 release from human PBMCs by CL264 stimulation can be measured by adding each anti-human TLR7 antibody to human PBMCs at various concentrations.

It has been experimentally proved and widely recognized that, in various immune inflammation-related diseases including systemic lupus erythematosus, the ligand concentration of human TLR7 is increased, human TLR7 expression is enhanced, or human TLR7 stimulation is caused. Inflammatory responses due to inflammatory cytokines such as interleukin 6 (IL-6) produced by the action of human TLR7 ligands on human TLR7-expressing cells and release of type I interferons due to enhancement and activation of antibody production cause systemic immune inflammatory responses and cause development of, or worsen, autoimmunity such as systemic lupus erythematosus. Accordingly, suppressing the production of cytokines which depend on human TLR7 stimulation leads to prevention and treatment of systemic lupus erythematosus and the like, and the usefulness of a human TLR7 antibody as a remedy can be determined using suppression activity as an indicator.

Examples of a suitable antibody in the present invention can include an antibody or an antigen-binding fragment of the antibody which binds specifically to human TLR7 comprising the amino acid sequence set forth in SEQ ID NO: 2 or 4 and reduces the amount of IL-6 released by CL264-treated human PBMCs in a concentration dependent manner.

Further, the treatment or prevention effects by the anti-human TLR7 antibody on various diseases can be checked based on an in-vivo evaluation system or ex-vivo evaluation system by administration of the anti-human TLR7 antibody to monkeys cross-reactive with the antibody, or also based on the following in-vivo evaluation system by administration of the anti-human TLR7 antibody to human TLR7 transgenic and mouse TLR7 knockout mice.

The effects on inflammatory cytokine production are evaluated by comparing the ability to produce cytokine in the peripheral blood between the anti-TLR7 antibody group and the non-administration group, in inflammation induced by intraperitoneally or intravenously administering TLR7 ligands to mice.

The effects on atopic dermatitis are evaluated by quantifying the behavior caused by atopic dermatitis spontaneously developed or induced by a method such as repeatedly applying a mite antigen cream to the auricle or the back 3 to 6 times every 3 days to 2 weeks, applying haptens to the auricle, the abdomen, or the back daily to once a week, administering a pruritus inducer intradermally in the auricle, subcutaneously in the back, or intrathecally, or using NC/Nga mice which are spontaneous atopic mice, through measurement of the frequency of pruritus using magnets mounted on both insteps of mice and a pruritus behavior measuring device, or inspection of the pathological features of the skin, the peripheral blood, the spinal cord tissue, and the like, and comparing the results between the anti-human TLR7 antibody group and the non-administration group.

The effects on psoriasis are evaluated by quantifying psoriasiform dermatitis induced by a method such as applying Imiquimod or R848 to the auricle and the back after shaving, administering cytokines such as IL-23 to mice intradermally in the auricle, through such as measurement of the weight and the thickness of the inflammation site or the myeloperoxidase activity of neutrophils infiltrating the site, flow cytometry analysis of the infiltrated cells, gene analysis, or measurement of the cytokine concentration, and comparing the results between the anti-TLR7 antibody group and the non-administration group.

The effects on arthritis are evaluated by inducing arthritis by a method such as administering an emulsion obtained by mixing a bovine type II collagen solution and a complete Freund's adjuvant intradermally to the tail base of mice and thereafter administering an emulsion obtained by mixing a bovine type II collagen solution and an incomplete Freund's adjuvant 2 to 3 weeks later, or administering an anti-bovine type II collagen antibody and TLR ligands, and comparing the scoring of subsequent joint swelling, measurement of the thickness of the footpad, the concentrations of antibodies, cytokines or blood biomarkers in the blood or tissues, or the proliferative activity, the ability to produce cytokine or the surface antigens of the cells obtained from the peripheral blood, the spleen, the lymph nodes, the bone marrow, the joint sites, or the like, between the anti-human TLR7 antibody group and the non-administration group.

The effects on colitis are evaluated by inducing colitis by a method such as administering trinitrobenzene sulfonic acid into the intestine of mice fasted for 24 hours, allowing ad libitum access to a 1 to 10% dextran sodium sulfate aqueous solution from a supply bottle for 4 days to 2 weeks, or transferring CD4+CD25−CD45RBhi T cells collected from the lymph nodes and the spleen of human TLR7 transgenic mice after purification intraperitoneally to Rag2-deficient mice, and comparing the body weight during the observation period, the thickening degree, the number and size of polyps, and the histopathological features of the intestine by autopsy after the completion of the test, the concentrations of antibodies, cytokines or blood biomarkers in the blood or tissues, the proliferative activity, the ability to produce cytokine or the surface antigens of the cells obtained from the intestine, the peripheral blood, the thymus, the spleen, the lymph nodes, the bone marrow, or Peyer's patches, or the like, between the anti-human TLR7 antibody group and the non-administration group.

The effects on systemic lupus erythematosus are evaluated by comparing between the anti-human TLR7 antibody group and the non-administration group: the concentrations of antibodies, cytokines or blood biomarkers in the blood or tissues collected from NZB/WF1 mice, MRL/lpr mice and BXSB mice which are spontaneous models over time, the antibody titer or the biomarker concentration in their urine, or a symptom induced by transferring cells prepared from an organ such as the spleen and the lymph nodes collected after the completion of the above test to untreated mice, or the like.

The effects on hepatitis are evaluated by inducing hepatitis by a method such as administering D-galactosamine alone or in combination with lipopolysaccharide intraperitoneally to mice and administering concanavalin A alone into the tail vein, and comparing the AST and ALT concentrations in the blood collected 1 hour to 1 week after administering an inflammatory substance, the cytokine concentration, and the histopathological condition of liver lesions, between the anti-human TLR7 antibody group and the non-administration group.

The thus obtained antibody that inhibits the biological activity of human TLR7 is useful as a pharmaceutical, particularly, as an antibody for preventing or treating immune inflammation-related diseases including systemic lupus erythematosus, allergic diseases, infections, or cancers.

As one example, the anti-human TLR7 antibody can be administered alone or in combination with at least one other therapeutic agent, for treating or preventing immune inflammation-related diseases, allergic diseases, infections, or cancers. Examples of the other therapeutic agent which can be administered in combination with the anti-human TLR7 antibody can include corticosteroids, non-steroidal anti-inflammatory drugs, nucleic acid antimetabolites, nucleic acid synthesis inhibitors, antifolates, calcineurin inhibitors, anti-malarial drugs, antithymocyte globulins, biologics targeting cell surface antigens, or biologics targeting cytokine interferons or cytokine interferon receptors, but there is no limitation to these examples.

Specific examples of the therapeutic agent can include Methylprednisolone as a corticosteroid, Loxoprofen Sodium Hydrate, Diclofenac sodium, Indomethacin, and Acetyl salicylic acid as non-steroidal anti-inflammatory drugs, Mycophenolate mofetil as a nucleic acid antimetabolite, Cyclophosphamide as a nucleic acid synthesis inhibitor, Cyclosporin and Taclorims as calcineurin inhibitors, Hydroxychloroquine as an anti-malarial drug, Methotrexate as an antifolate, Zetbulin, Lymphoglobuline, and Thymoglobulin as antithymocyte globulins, Alemtuzumab, Rituximab, and Abatacept as biologics targeting cell surface antigens, and Infliximab, Etanercept, Adalimumab, Tocilizumab, Belimumab and Anifrolumab as biologics targeting cytokine interferons or cytokine interferon receptors.

Depending on the condition of immune inflammation-related diseases, allergic diseases, infections or cancers and the degree of treatment and/or prevention targeted, two, three or more types of other therapeutic agents can also be administered, and the other therapeutic agents can be encapsulated in the same preparation so as to be administered at the same time. The other therapeutic agents and the anti-human TLR7 antibody can also be encapsulated in the same preparation so as to be administered at the same time. Further, the anti-human TLR7 antibody and the other therapeutic agents can also be encapsulated in separate preparations and administered at the same time. Further, the other therapeutic agents and the anti-human TLR7 antibody can also be administered separately one after another. That is, a therapeutic agent containing the anti-human TLR7 antibody or the antigen-binding fragment of the antibody as an active ingredient may be administered after the other therapeutic agents are administered, or the other therapeutic agents may be administered after a therapeutic agent containing the anti-human TLR7 antibody or the antigen-binding fragment of the antibody as an active ingredient is administered. In the case of administration in gene therapy, the gene of a protein therapeutic agent and the gene of the anti-human TLR7 antibody can be inserted downstream of the same or separate promoter regions and can be introduced into the same or separate vectors.

The targeted drug conjugates disclosed in M. C. Garnet "Targeted drug conjugates: principles and progress", Advanced Drug Delivery Reviews, (2001) 53, 171-216 can be produced by binding the therapeutic agents to the anti-human TLR7 antibody or its fragment. For this purpose, any antibody fragment can be applied, other than antibody molecules, as long as it does not completely lose T-cell recognition. Examples thereof can include fragments such as Fab, $F(ab')_2$, and Fv, and the antibody and such fragments can be used in the same manner as in the present invention. The binding mode of the anti-human TLR7 antibody, or the fragment of the antibody, to the therapeutic agents can be in various forms disclosed in M. C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123, etc. That is, examples thereof can include a mode in which the anti-human TLR7 antibody is chemically bound to the therapeutic agents directly or via a spacer such as an oligopeptide, or bound via a suitable drug carrier. Examples of the drug carrier can include liposomes and water-soluble polymers. More specifically, examples of the mode of binding via such a drug carrier can include a mode in which the antibody and the therapeutic agents are included in a liposome, and the liposome is bound to the antibody, and a mode in which the therapeutic agents are chemically bound to a water-soluble polymer (compound with a molecular weight of about 1000 to 100000) directly or via a spacer such as an oligopeptide, and the antibody is bound to the water-soluble polymer. The antibody (or the fragment) can be bound to the therapeutic agents or the drug carriers such as liposomes and water-soluble polymers by a method known to those skilled in the art such as the method according to G. T. Hermanson "Bioconjugate Techniques" Academic Press, California (1996), Putnam and J. Kopecek "Polymer Conjugates with Anticancer Activity" Advances in Polymer Science (1995) 122, 55-123. The therapeutic agents can be included in the liposome by a method known to those skilled in the art such as the method according to D. D. Lasic "Liposomes: From Physics to Applications", Elsevier Science Publishers B. V., Amsterdam (1993). The therapeutic agents can be bound to the water-soluble polymer by a method known to those skilled in the art such as the method according to D. Putnam and J Kopecek "Polymer Conjugates with Anticancer Activity" Advances in Polymer Science (1995) 122, 55-123. The conjugates of the antibody (or the fragment) and a protein therapeutic agent (or the fragment) can be produced by a genetic engineering method known to those skilled in the art other than the aforementioned method.

The present invention also provides a pharmaceutical composition comprising an expression vector which comprises a polynucleotide comprising a polynucleotide sequence encoding at least one or those of the anti-human TLR7 antibody or the antigen-binding fragment of the antibody, as an active ingredient in an amount effective for treating and/or preventing disease, and a diluent, a carrier, a solubilizer, an emulsifier, a preservative and/or an additive, which are pharmaceutically acceptable.

The present invention also provides a pharmaceutical composition comprising an expression vector which comprises a polynucleotide comprising a polynucleotide sequence encoding at least one or those of the anti-human TLR7 antibody or the antigen-binding fragment of the antibody, in an amount effective for treating and/or preventing disease, at least one therapeutic agent in an amount effective for treating and/or preventing disease, and a diluent, a carrier, a solubilizer, an emulsifier, a preservative, and/or an additive, which are pharmaceutically acceptable.

Examples of the therapeutic agent can include antifolates, calcineurin inhibitors, corticosteroids, antithymocyte globulins, nucleic acid antimetabolites, nucleic acid synthesis inhibitors, biologics targeting cell surface antigens, or biologics targeting cytokines or cytokine receptors described above, but there is no limitation to these examples.

The substances used for preparations which are acceptable in the pharmaceutical composition of the present invention are preferably non-toxic, preferably at the administration dosage and the administration concentration, to a person to whom the pharmaceutical composition is administered.

The pharmaceutical composition of the present invention can contain substances used for preparations for changing or maintaining the pH, the osmotic pressure, the viscosity, the transparency, the color, the isotonicity, the sterility, the stability, the dissolution rate, the sustained release rate, the absorption rate and the penetration rate. Examples of the substances used for preparations can include, but are not limited to: amino acids such as glycine, alanine, glutamine, asparagine, arginine or lysine, antibacterial agents, antioxidants such as ascorbic acid, sodium sulfate or sodium bisulfite, buffers such as phosphoric acid, citric acid, boric acid buffer, sodium bicarbonate or a tris-hydrochloric acid (Tris-Hcl) solution, fillers such as mannitol or glycine, chelating agents such as ethylenediaminetetraacetic acid (EDTA), complexing agents such as caffeine, polyvinyl pyrrolidine, β-cyclodextrin, or hydroxypropyl-β-cyclodextrin, extenders such as glucose, mannose or dextrin, other carbohydrates such as monosaccharides or disaccharides, coloring agents, flavoring agents, diluents, emulsifiers, hydrophilic polymers such as polyvinyl pyrrolidine, preservatives such as low-molecular weight polypeptides, salt-forming counterions, benzalkonium chloride, benzoic acid, salicylic acid, thimerosal, phenethyl alcohol, methylparaben, propylparaben, chlorhexidine, sorbic acid or hydrogen peroxide, solvents such as glycerin, propylene glycol or polyethylene glycol, sugar alcohols such as mannitol or sorbitol, suspending agents, polysorbates such as sorbitan ester, polysorbate 20 or polysorbate 80, surfactants such as triton, tromethamine, lecithin or cholesterol, stability enhancers such as sucrose or sorbitol, elasticity enhancers such as sodium chloride, potassium chloride, mannitol or sorbitol, transport agents, excipients, and/or pharmaceutical auxiliary agents. The amount of the substances used for preparations is to be added at preferably 0.01 to 100 times, particularly 0.1 to 10 times, with respect to the weight of the anti-human TLR7 antibody. The suitable composition of the pharmaceutical composition in preparations can be appropriately determined by those skilled in the art, corresponding to the disease to be applied, the administration route to be applied, or the like.

Excipients or carriers in the pharmaceutical composition may be liquid or solid. Suitable excipients or carriers may be water for injection, normal saline, artificial cerebrospinal fluid, or other substances generally used for parenteral administration. Neutral normal saline or normal saline containing serum albumin can also be used for carriers. The pharmaceutical composition can contain a Tris buffer with a pH of 7.0 to 8.5, an acetate buffer with a pH of 4.0 to 5.5 or a citric acid buffer with a pH of 3.0 to 6.2. Further, these buffers can also contain sorbitol or other compounds. Examples of the pharmaceutical composition of the present invention can include a pharmaceutical composition comprising anti-human TLR7 antibody and a pharmaceutical composition comprising anti-human TLR7 antibody and at least one therapeutic agent, and the pharmaceutical composition of the present invention is prepared as a drug having a selected composition and a necessary purity, in the form of a freeze-dried product or liquid. A pharmaceutical composition comprising anti-human TLR7 antibody and a pharmaceutical composition comprising anti-human TLR7 antibody and at least one bone metabolism disorder therapeutic drug can be formed as a freeze-dried product using a suitable excipient such as sucrose.

The pharmaceutical composition of the present invention can be prepared for parenteral administration or can be prepared for oral gastrointestinal absorption. The composition and the concentration of the preparation can be determined depending on the administration method. Alternatively, an affinity that is a higher affinity (lower Kd value), in terms of the dissociation constant (Kd value) to human TLR7 of the anti-human TLR7 antibodies contained in the pharmaceutical composition of the present invention, enables the drug efficacy to be exerted with reduced dosage in humans, and therefore the dosage of the pharmaceutical composition of the present invention in humans can also be determined based on this affinity. The dosage in the present invention may be about 0.1 to 100 mg/kg once every 1 to 180 days when the anti-human TLR7 antibody is administered to a human.

Examples of embodiments of the pharmaceutical composition of the present invention can include injections including intravenous drip, suppositories, nasal preparations, sublingual preparations and transdermal drugs.

Although most approved antibody preparations are intravenously administered, subcutaneous administration is preferred in many medical settings. In such a case, the volume is limited to 1.0 to 1.5 mL, and thus a high-concentration antibody solution is required depending on the dosage. However, when the concentration is increased, the viscosity of the drug solution increases, and therefore the injection may be impossible due to the high viscosity with the thickness of commonly used injection needles. That is, in the case of selecting an injection, the property of low viscosity has an important meaning to be prioritized as an embodiment of the pharmaceutical composition, and a suitable antibody can be selected using the viscosity as an indicator.

EXAMPLES

Hereinafter, the present invention will be specifically described by way of examples, but the present invention is not limited to these examples. In the following examples, each operation related to genetic engineering is performed according to the method disclosed in "Molecular Cloning" (Sambrook, J., Fritsch, E. F. and Maniatis, T., Cold Spring Harbor Laboratory Press, 1989) or performed using a commercially available reagent or kit according to the instruction of the commercially available product, unless otherwise specified.

Example 1

Production of Mouse Anti-Human TLR7 Antibody

1)-1 Immunization

1)-1-1 Establishment of Ba/F3 cell line expressing human TLR7-Flag-His×6/human Unc93B1-HA×2

The human TLR7 (variant 2) gene (SEQ ID NO: 3) was integrated into retroviral vectors, pMXs (Cell Biolabs, Inc.) tagged with Flag-His×6 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to a Ba/F3 cell line (RIKEN, BRC), and high-speed centrifugation was performed at 2000 rpm for 1 hour, to establish a Ba/F3 cell line expressing human TLR7-Flag-His×6.

The human TLR7 encoded by the human TLR7 (variant 2) gene (SEQ ID NO: 3) comprises the amino acid sequence of SEQ ID NO: 4. The sequence is shown in FIG. 2.

The human Unc93B1 gene (SEQ ID NO: 55) was integrated into retroviral vectors, pMXs (Cell Biolabs, Inc.) tagged with HA×2 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to the Ba/F3 cell line expressing human TLR7-Flag-His×6 established above, and high-speed centrifugation was performed at 2000 rpm for 1 hour, to establish a Ba/F3 cell line expressing human TLR7-Flag-His×6/human Unc93B1-HA×2.

1)-1-2 Mouse Immunization

The Ba/F3 cell line expressing human TLR7-Flag-His×6/human Unc93B1-HA×2 established above in 1)-1-1 was mixed with an adjuvant, TITERMAX® Gold (TiterMax USA, Inc.), and the mixture was administered as an antigen to the sole, the tail base, and the peritoneal cavity of TLR9-deficient mice with BALB/c background produced by the Institute of Medical Science of the University of Tokyo a total of 3 times per week.

At the 4th time, the Ba/F3 cell line expressing human TLR7-Flag-His×6/human Unc93B1-HA×2 suspended in 1×PBS was intraperitoneally administered.

The spleen was removed 5 days after the last immunization and used for producing hybridomas.

1)-2 Production of Hybridomas

The spleen cells after the immunization were mixed with Sp2/o cell line (ATCC), and cell fusion was performed using an HVJ-E cell fusion kit (ISHIHARA SANGYO KAISHA, LTD). In order to select hybridomas, the cells were cultured from the day after the cell fusion operation in RPMI1640 (Life Technologies) containing a HAT (Thermo Fisher Scientific)-containing culture solution (10% FBS), 50-μM 2-Mercaptoethanol (Life Technologies), 50-U/mL Penicillin, and 50-μg/mL Streptomycin (Life Technologies), and the hybridoma colonies that emerged were collected to produce monoclonal hybridomas.

1)-3 Screening of Antibody Binding to Human TLR7 by Flow Cytometry

The culture supernatant was collected from hybridomas forming colonies under a microscope and used for screening. A Ba/F3 cell line expressing hTLR7-Flag-His×6/hUnc93B1-HA×2 subjected to membrane permeation with 0.1% Saponin (Sigma-Aldrich Co. LLC) and Ba/F3 cells expressing nothing were each stained with the culture supernatant and analyzed by flow cytometry (LSRFortessaTMX-20, Becton, Dickinson and Company), to select hybridomas producing anti-hTLR7 antibody.

1)-4 Screening of Human TLR7 Antibody Inhibition of Human TLR7 Function by Flow Cytometry The human TLR7 (variant 2) gene (SEQ ID NO: 3) and the human Unc93B1 D34A mutant-HA×2 gene (SEQ ID NO: 86) were introduced into a Ba/F3 cell line (RIKEN, BRC) using a retrovirus. Further, a NF-κB-green fluorescence protein (GFP) reporter plasmid (STRATAGENE) was transfected into the cells by the electroporation method, so that a Ba/F3 cell line expressing hTLR7/hUnc93B1 D34A mutant-HA×2 and capable of analyzing NF-κB activation was established, and the hybridoma culture supernatant was added to the cell line. The cells were stimulated 4 hours later with 25 ng/ml of a TLR7 ligand, R848 (InvivoGen). As a result of analyzing the inhibitory effects of human TLR7 response by measuring the GFP fluorescence intensity using flow cytometry 24 hours later, three mouse anti-human TLR7 antibody-producing hybridomas were selected and were named AT01, NB7, and FAN2, respectively.

In this description, antibodies produced by hybridomas AT01, NB7, and FAN2 are referred to as AT01 antibody, NB7 antibody, and FAN2 antibody, respectively.

1)-5 Determination of Isotype of Antibody

The isotypes of the antibodies produced by the mouse anti-human TLR7 antibody-producing hybridomas (AT01, NB7, and FAN2) obtained in 1)-4 were each determined using an IsoStrip Mouse Monoclonal Antibody Isotyping Kit (Merck KGaA). As a result, the isotypes of AT01 antibody, NB7 antibody, and FAN2 antibody were each determined to be an IgG1/κ chain.

1)-6 Preparation of Mouse Anti-Human TLR7 Antibody

The mouse anti-human TLR7 monoclonal antibody was purified from ascites collected about 10 days after each hybridoma was intraperitoneally administered to ICR-CD1-Foxn1 nude mice (ICR-nu, CHARLES RIVER LABORATORIES JAPAN, INC.) pretreated with pristane (Sigma-Aldrich Co. LLC., currently, Merck KGaA).

First, pristane was intraperitoneally administered to ICR-nu, and the mice were bred for 7 days or more. Thereafter, the AT01, NB7, or FAN2-producing hybridoma was cultured in RPMI1640 (Life Technologies) containing 10% FBS, 50-μM 2-Mercaptoethanol (Life Technologies), 50-U/mL Penicillin, and 50-μg/mL Streptomycin (Life Technologies), followed by proliferation to a sufficient volume. Thereafter, the hybridoma was suspended in 1×PBS and intraperitoneally administered to the ICR-nu.

Ascites was collected 10 days later, and the blood cells were sedimented by a high-speed centrifuge, to collect a supernatant. After 10-fold dilution with 1×PBS, the ascites was passed through a 0.45 μm filter (Millipore).

The antibody was purified from the aforementioned ascites on a proteinG column (GE Healthcare Japan Corporation) using an AKTAprime plus (GE Healthcare Japan Corporation).

Subsequently, buffer replacement with saline was performed together with enrichment using PD-10 (GE Healthcare Japan Corporation), to prepare the antibody at a concentration of 1.0 mg/mL or more.

Finally, sterilization with Millex-GV 0.22 μm (Millipore) was performed, to give a purified sample.

Example 2

In Vitro Evaluation of Mouse Anti-Human TLR7 Antibody

2)-1 Evaluation of Binding Selectivity of Mouse Anti-Human TLR7 Antibody

2)-1-1 Establishment of Ba/F3 Cell Line Expressing Mouse TLR7-Flag-His×6

The mouse TLR7 gene (SEQ ID NO: 56) was integrated into retroviral vectors, pMXs (Cell Biolabs, Inc.) tagged with Flag-His×6 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to a Ba/F3 cell line (RIKEN, BRC), and high-speed centrifugation was performed at 2000 rpm for 1 hour, to establish a Ba/F3 cell line expressing mouse TLR7-Flag-His×6.

The mouse TLR7 encoded by the mouse TLR7 gene (SEQ ID NO: 56) comprises the amino acid sequence of SEQ ID NO: 83. The sequence is shown in FIG. 3.

2)-1-2 Establishment of Ba/F3 Cell Line Expressing Rat TLR7-Flag-His×6

The rat TLR7 gene (SEQ ID NO: 57) was integrated into retroviral vectors, pMXs (Cell Biolabs, Inc.) tagged with Flag-His×6 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to a Ba/F3 cell line (RIKEN, BRC), and high-speed centrifugation was performed at 2000 rpm for 1 hour, to establish a Ba/F3 cell line expressing rat TLR7-Flag-His×6.

The rat TLR7 encoded by the rat TLR7 gene (SEQ ID NO: 57) comprises the amino acid sequence of SEQ ID NO: 84. The sequence is shown in FIG. 4.

2)-1-3 Establishment of Ba/F3 Cell Line Expressing Monkey TLR7-Flag-His×6

The monkey TLR7 gene (SEQ ID NO: 58) was integrated into retroviral vectors, pMXs (Cell Biolabs, Inc.) tagged with Flag-His×6 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to a Ba/F3 cell line (RIKEN, BRC), and high-speed centrifugation was performed at 2000 rpm for 1 hour, to construct a Ba/F3 cell line expressing monkey TLR7-Flag-His×6.

The monkey TLR7 encoded by the monkey TLR7 gene (SEQ ID NO: 58) comprises the amino acid sequence of SEQ ID NO: 85. The sequence is shown in FIG. 5.

2)-1-4 Evaluation of Binding Selectivity of Mouse Anti-Human TLR7 Antibody by Flow Cytometry The Ba/F3 cell line expressing human TLR7-Flag-His×6/human Unc93B1-HA×2 established above in 1)-1-1, the Ba/F3 cell line expressing mouse TLR7-Flag-His×6 established above in 2)-1-1, the Ba/F3 cell line expressing rat TLR7-Flag-His×6×2 established above in 2)-1-2, and the Ba/F3 cell line expressing monkey TLR7-Flag-His×6 established above in 2)-1-3 were subjected to membrane permeation with 0.1% Saponin and stained using AT01 antibody, NB7 antibody, and FAN2 antibody, and a secondary antibody, Goat anti-mouse IgG (H+L)-PE (eBioscience). The binding selectivity of each antibody was evaluated by comparing the average fluorescence intensity (MFI) based on flow cytometry analysis.

The results indicate that AT01 antibody, NB7 antibody, and FAN2 antibody specifically bound to human TLR7 or monkey TLR7 and did not bind to mouse TLR7 or rat TLR7.

2)-2 Evaluation of Binding Ability of Mouse Anti-Human TLR7 Antibody

The Ba/F3 cell line expressing human TLR7-Flag-His×6/human Unc93B1-HA×2 established above in 1)-1-1 was subjected to membrane permeation with 0.1% Saponin and stained using a dilution series of AT01 antibody, NB7 antibody, and FAN2 antibody, and a secondary antibody, Goat anti-mouse IgG (H+L)-PE (eBioscience). The binding activity of each antibody was evaluated by comparing the mean fluorescence intensity (MFI) based on flow cytometry analysis.

The results indicate that the antibody having the highest binding activity was in the order of AT01 antibody, NB7 antibody, and FAN2 antibody.

2)-3 Inhibitory Activity of Mouse Anti-Human TLR7 Antibody on Cytokine Production Human PBMCs were purchased from Cellular Technology Limited as a frozen product and thawed according to the instructions for use.

The PBMCs suspended at a concentration of $2.5\times10^6$ cells/mL in RPMI1640 (Life Technologies Corp.) containing 10% FBS, 1-mM Sodium Pyruvate (Life Technologies Corp.), 0.1-mM MEM Non-Essential Amino Acids (Life Technologies Corp.), 50-μM 2-Mercaptoethanol (Life Technologies Corp.), 50-U/mL Penicillin, and 50-μg/mL Streptomycin (Life Technologies Corp.) were seeded in a 96-well cell culture plate at 100 μL each, and the mouse anti-human TLR7 antibody, AT01 antibody, NB7 antibody, or FAN2 antibody, or a mouse IgG control antibody (BioLegend, Inc.) was added thereto at 80 μL/well, followed by pretreatment in an incubator at 37° C. for 4 hours.

Thereafter, 1-mg/mL CL-264 (InvivoGen) was added thereto at 20 μL/well, and the mixture was stirred well, followed by culturing at 37° C. for about 20 hours under 5% $CO_2$. The plate was stirred well and thereafter centrifuged at 1500 rpm for 5 minutes, and the concentration of interleukin-6 (IL-6) contained in the supernatant was measured by the FRET method (Cisbio Bioassay. Inc).

FIG. 6 shows the results. The mouse anti-human TLR7 antibody suppressed the production of IL-6 from the human PBMCs treated with CL-264 in a concentration dependent manner. The AT01 antibody, NB7 antibody, and FAN2 antibody inhibited the production of IL-6 from the human PBMCs in a concentration dependent manner. The half-inhibitory concentrations ($IC_{50}$) of AT01 antibody, NB7 antibody and FAN2 antibody were 192 ng/mL, 771 ng/mL, and 8389 ng/mL, respectively, which were calculated from the concentrations of the two values, which are either side of the 50% inhibitory activity, and the inhibitory activity when each of the two concentrations were added.

Meanwhile, inhibition was not observed in the mouse IgG control antibody even at a concentration of 10 μg/mL.

Example 3

Determination of Nucleotide Sequence and Amino Acid Sequence of cDNA Encoding Variable Region of Mouse Anti-Human TLR7 Antibody 3)-1 Synthesis of cDNA Total RNA was collected from the hybridomas of AT01, NB7, and FAN2 using a TRIzol Reagent (Ambion). Subsequently, cDNA was synthesized using a PrimeScript 1st Strand cDNA Synthesis Kit (TAKARA).

3)-2 Amplification and Sequencing of Mouse Immunoglobulin Heavy- and Light-Chain Variable Region Gene Fragments The nucleotide sequences encoding the variable regions of the antibody contained in the synthesized cDNA were determined by GenScript Corporation.

3)-2-1 Mouse Anti-Human TLR7 Antibody (AT01)

The amino acid sequence encoded by the nucleotide sequence of cDNA encoding the heavy-chain variable region of AT01 antibody determined above is set forth in SEQ ID NO: 5 in the Sequence Listing.

The amino acid sequence encoded by the nucleotide sequence of cDNA encoding the light-chain variable region of AT01 antibody determined above is set forth in SEQ ID NO: 11 in the Sequence Listing.

3)-2-2 Mouse Anti-Human TLR7 Antibody (NB7)

The amino acid sequence encoded by the nucleotide sequence of cDNA encoding the heavy-chain variable region of NB7 antibody determined above is set forth in SEQ ID NO: 7 in the Sequence Listing.

The amino acid sequence encoded by the nucleotide sequence of cDNA encoding the light-chain variable region of NB7 antibody determined above is set forth in SEQ ID NO: 13 in the Sequence Listing.

3)-2-3 Mouse Anti-Human TLR7 Antibody (FAN2)

The amino acid sequence encoded by the nucleotide sequence of cDNA encoding the heavy-chain variable region of FAN2 antibody determined above is set forth in SEQ ID NO: 9 in the Sequence Listing.

The amino acid sequence encoded by the nucleotide sequence of cDNA encoding the light-chain variable region of FAN2 antibody determined above is set forth in SEQ ID NO: 15 in the Sequence Listing.

Example 4

Production of Chimeric Anti-Human TLR7 Antibody

4)-1 Construction of Expression Vector of Chimeric Anti-TLR7 Antibody

4)-1-1 Construction of Chimeric Light-Chain Expression Vector, pCMA-LK

A DNA fragment (SEQ ID NO: 59) containing an approximately 5.4-kb fragment obtained by digesting plasmid pcDNA3.3-TOPO/LacZ (Invitrogen Corp.) with restriction enzymes, XbaI and PmeI and a DNA sequence encoding the human light-chain signal sequence and the human kappa-chain constant region were bound together using an In-Fusion HD PCR cloning kit (Clontech Laboratories, Inc.), to produce pcDNA3.3/LK. pCMA-LK was constructed by removing the neomycin expression unit from pcDNA3.3/LK.

4)-1-2 Construction of Chimeric IgG1 Heavy-Chain Expression Vector, pCMA-G1

A DNA fragment (SEQ ID NO: 60) containing a DNA fragment obtained by digesting pCMA-LK with XbaI and PmeI and removing the light chain signal sequence and the human kappa-chain constant region was bound to a DNA sequence encoding the human heavy-chain signal sequence and the human IgG1 constant region using an In-Fusion HD PCR cloning kit (Clontech Laboratories, Inc.), to construct pCMA-G1.

4)-1-3 Construction of AT01 Chimeric Anti-Human TLR7 Antibody Expression Vector

A DNA fragment comprising the nucleotide sequence encoding the heavy-chain variable region of cAT01 antibody represented by nucleotides 36 to 422 in the nucleotide sequence set forth in SEQ ID NO: 61 was synthesized (Geneart AG). The synthesized DNA fragment was inserted into the site where pCMA-G1 was cut with a restriction enzyme, BlpI, using an In-Fusion HD PCR cloning kit (Clontech Laboratories, Inc.), thereby constructing a cAT01 antibody heavy-chain expression vector. The heavy chain of cAT01 antibody comprises the amino acid sequence of SEQ ID NO: 35 including the signal sequence. The sequence is shown in FIG. 7.

The DNA fragment (SEQ ID NO: 62) comprising a DNA sequence encoding the light chain of cAT01 antibody was synthesized (Geneart AG). Using the pCMA-LK produced in Example 4)-1-1, a cAT01 antibody light-chain expression vector was constructed in the same manner as above. The light chain of cAT01 antibody comprises the amino acid sequence of SEQ ID NO: 36 including the signal sequence. The sequence is shown in FIG. 7.

4)-1-4 Construction of NB7 Chimeric Anti-Human TLR7 Antibody Expression Vector

A DNA fragment comprising the nucleotide sequence encoding the heavy-chain variable region of cNB7 antibody represented by nucleotides 36 to 440 in the nucleotide sequence set forth in SEQ ID NO: 63 was synthesized (Geneart AG). A cNB7 heavy-chain expression vector was constructed in the same manner as in Example 4)-1-3. The heavy chain of cNB7 antibody comprises the amino acid sequence of SEQ ID NO: 37 including the signal sequence. The sequence is shown in FIG. 8.

A DNA fragment (SEQ ID NO: 64) comprising the DNA sequence encoding the cNB7 light chain was synthesized (Geneart AG). Using the pCMA-LK produced in Example 4)-1-1, a cNB7 light-chain expression vector was constructed in the same manner as in Example 4)-1-3. The light chain of cNB7 antibody comprises the amino acid sequence of SEQ ID NO: 38 including the signal sequence. The sequence is shown in FIG. 8.

4)-1-5 Construction of FAN2 Chimeric Anti-Human TLR7 Antibody Expression Vector

A DNA fragment comprising the nucleotide sequence encoding the heavy-chain variable region of cFAN2 antibody represented by nucleotides 36 to 437 in the nucleotide sequence set forth in SEQ ID NO: 65 was synthesized (Geneart AG). A cFAN2 heavy-chain expression vector was constructed in the same manner as in Example 4)-1-3. The heavy chain of cFAN2 antibody comprises the amino acid sequence of SEQ ID NO: 39 including the signal sequence. The sequence is shown in FIG. 9.

A DNA fragment (SEQ ID NO: 66) comprising the DNA sequence encoding the cFAN2 light chain was synthesized (Geneart AG). Using the pCMA-LK produced in Example 4)-1-1, a cFAN2 light-chain expression vector was constructed in the same manner as in Example 4)-1-3. The light chain of cFAN2 antibody comprises the amino acid sequence of SEQ ID NO: 40 including the signal sequence. The sequence is shown in FIG. 9.

4)-2 Production of Chimeric Anti-Human TLR7 Antibody

4)-2-1 Production of Chimeric AT01 Antibody

FreeStyle 293F cells (Invitrogen Corp.) were passaged and cultured according to the manual. $1.2\times10^9$ FreeStyle 293F cells (Invitrogen Corp.) in the logarithmic growth phase were seeded in a 3-L Fernbach Erlenmeyer Flask (Corning Incorporated) and diluted with a FreeStyle293 expression medium (Invitrogen Corp.) at a concentration of to $2.0\times10^6$ cell/mL. 0.24 mg of the heavy-chain expression vector constructed above in 4)-1-3, 0.36 mg of the light-chain expression vector constructed above in 4)-1-3, and 1.8 mg of Polyethyleneimine (Polyscience #24765) were added to 40 mL of an Opti-Pro SFM medium (Invitrogen Corp.), followed by gentle stirring and further standing for 5 minutes. Thereafter, the mixture was added to the FreeStyle 293F cells. After shaking culture in an incubator at 37° C. under 8% $CO_2$ for 4 hours at 90 rpm, 600 ml of EX-CELL VPRO medium (SAFC Biosciences), 18 ml of GlutaMAX I (Gibco), and 30 mL of Yeastolate Ultrafiltrate (Gibco) were added thereto, followed by shaking culture in an incubator at 37° C. under 8% $CO_2$ at 90 rpm for 7 days, and the culture supernatant obtained was filtered with a Disposable Capsule Filter (Advantec #CCS-045-E1H), to produce a chimeric AT01 antibody.

4)-2-2 Production of Chimeric NB7 Antibody

Using the heavy-chain expression vector and light-chain expression vector constructed in 4)-1-4 above, a chimeric NB7 antibody was produced by the method of 4)-2-1.

4)-2-3 Production of Chimeric FAN2 Antibody

Using the heavy-chain expression vector and light-chain expression vector constructed in 4)-1-5 above, a chimeric FAN2 antibody was produced by the method of 4)-2-1.

4)-3 Purification of Chimeric Anti-Human TLR7 Antibody

An antibody of interest was purified from each culture supernatant obtained in Example 4)-2 by a one-step process of rProtein A affinity chromatography. The culture supernatant was applied to a column (GE Healthcare Bioscience) filled with MabSelectSuRe equilibrated with PBS, and thereafter the column was washed with PBS in a volume of twice or more the column volume. Next, elution was carried out with a 2M arginine hydrochloride solution (pH 4.0), to collect a fraction containing the antibody. The fraction was subjected to buffer replacement with PBS(−) by dialysis (Slide-A-Lyzer Dialysis Cassette, Thermo Scientific). The antibody was concentrated with a Centrifugal UF Filter Device, VIVASPIN20 (fraction molecular weight UF10K, Sartorius AG), to prepare the IgG at a concentration of 10 mg/mL or more. Finally, filtration was carried out with a Minisart-Plus filter (Sartorius AG), to give a purified sample.

Example 5

In Vitro Activity of Chimeric Anti-Human TLR7 Antibody

5)-1 Antigen-Binding Activity of Chimeric Anti-Human TLR7 Antibody by Flow Cytometry A Ba/F3 cell line expressing human TLR7-Flag-His×6/hUnc93B1-HA×2 was subjected to membrane permeation with 0.1% Saponin and stained using the dilution series of chimeric AT01 antibody, NB7 antibody, and FAN2 antibody at the antibody concentrations obtained in Example 4, and the secondary antibody, Goat anti-human IgG Fc-PE (eBioscience). The binding activity of each antibody was evaluated by comparing the MFI based on flow cytometry analysis. The results indicate that the antibody having the highest binding activity was in the order of chimeric AT01 antibody (cAT01), chimeric NB7 antibody (cNB7), and chimeric FAN2 antibody (cFAN2).

5)-2 Inhibitory Activity of Chimeric Anti-Human TLR7 Antibody on Cytokine Production Human PBMCs were purchased from Cellular Technology Limited as a frozen product and thawed according to the instructions for use. The PBMCs suspended at a concentration of $2.5\times10^6$ cells/mL in RPMI1640 (Life Technologies Corp.) containing 10% FBS, 1 mM Sodium Pyruvate (Life Technologies Corp.), 0.1-mM MEM Non-Essential Amino Acids (Life Technologies Corp.), 50 μM 2-Mercaptoethanol (Life Technologies Corp.), 50 U/mL Penicillin, and 50 μg/mL Streptomycin (Life Technologies Corp.) were seeded in a 96-well cell culture plate at 100 μL each, and the chimeric anti-human TLR7 antibody, cAT01, cNB7, or cFAN2, or a human IgG control antibody (Eureka Therapeutics) was added thereto at 80 μL/well, followed by pretreatment in an incubator at 37° C. for 4 hours. Thereafter, 1-mg/mL CL-264 (InvivoGen) was added thereto at 20 μL/well, and the mixture was stirred well, followed by culturing at 37° C. for about 20 hours under 5% $CO_2$. The plate was stirred well and thereafter centrifuged at 1500 rpm for 5 minutes, and the concentration of IL-6 contained in the supernatant was measured by the FRET method (Cisbio Bioassay. Inc).

Figure 10:
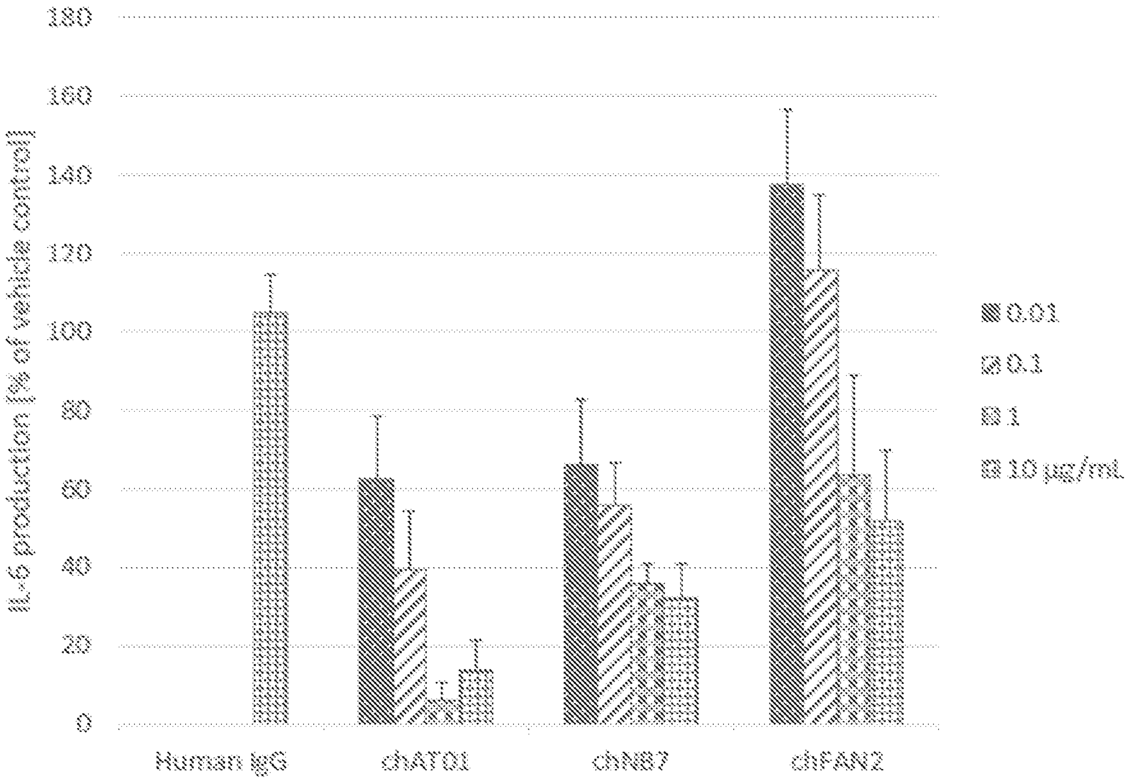
FIG. 10 is a graph showing that cAT01, cNB7, and cFAN2, which are chimeric anti-human TLR7 antibodies, suppress the production of IL-6 from human PBMCs treated with CL-264 in a concentration dependent manner.

FIG. 10 shows that the chimeric anti-human TLR7 antibody suppresses the production of IL-6 from the human PBMCs treated with CL-264 depending in a concentration dependent manner. The antibodies cAT01, cNB7, and cFAN2 inhibited the production of IL-6 from the human PBMCs depending on the concentration added. The half-inhibitory concentrations ($IC_{50}$) of the antibodies cAT01, cNB7 and cFAN2 were 35 ng/mL, 196 ng/mL, 10000 ng/mL or more, respectively, which were calculated from the concentrations of the two values, which are either side of the 50% inhibitory activity, and the inhibitory activity when each of the two concentrations were added.

Meanwhile, inhibition was not observed in the human IgG control antibody even at a concentration of 10 μg/mL.

Example 6

Production of Humanized Anti-Human TLR7 Antibody

6)-1 Humanized Design of Anti-Human TLR7 Antibody

6)-1-1 Molecular Modeling of Antibody Variable Regions

The molecular modeling of the variable regions was performed by a method known as homology modeling (Methods in Enzymology, 203, 121-153, (1991)) using a commercially available protein three-dimensional structure analysis program, BioLuminate (Schrodinger K.K). The template used was a structure registered in the Protein Data Bank (Nuc. Acid Res. 35, D301-D303 (2007)) having high sequence identity to the variable regions of the heavy and light chains.

6)-1-2 Design of Humanized Amino Acid Sequence

A technique known as CDR grafting (Proc. Natl. Acad. Sci. USA 86, 10029-10033(1989)) was used for humanization. Acceptors having high identity were selected from the consensus sequences defined in Kabat et al. (Sequences of Proteins of Immunological Interest, 5th Ed. Public Health Service National Institutes of Health, Bethesda, MD. (1991)) and the human germline sequences registered in IMGT® (THE INTERNATIONAL IMMUNOGENETICS INFORMATION SYSTEM, www.imgt.org), and donor residues to be transferred onto the acceptors were selected by analyzing the three-dimensional models with reference to the standards given by Queen et al. (Proc. Natl. Acad. Sci. USA 86, 10029-10033 (1989)).

6)-1-3 Design of Humanized Amino Acid Sequence of AT01 Antibody

The consensus sequences of human gamma-chain subgroup 1 and kappa-chain subgroup 1 having high identity to the framework regions of cAT01 were selected as the acceptors of cAT01. In the molecular modeling of the variable regions, a known structure (PDB ID: 1E4W) was used as a template.

6)-1-3-1 Humanization of AT01 Antibody Heavy Chain (1) the Heavy Chain Designed was Named huAT01_H1_IgG1LALA. huAT01_H1_IgG1LALA comprises the amino acid sequence set forth in SEQ ID NO: 45 including the signal sequence as a heavy-chain full-length amino acid sequence. The sequence is shown in FIG. 11. In the sequence, the amino acid sequence at positions 1 to 19 is the signal sequence, the amino acid sequence at positions 20 to 135 is the variable region, and the amino acid sequence at positions 136 to 465 is the constant region. Further, the amino acid sequence at positions 45 to 54 is CDRH1, the amino acid sequence at positions 69 to 78 is CDRH2, and the amino acid sequence at positions 118 to 124 is CDRH3.

The nucleotide sequence encoding the amino acid sequence of SEQ ID NO: 45 comprises the sequence set forth in SEQ ID NO: 67. Further, the nucleotide sequence encoding the heavy-chain variable region comprises the sequence set forth in SEQ ID NO: 77.

(2) the Heavy Chain Designed was Named huAT01_H3_IgG1LALA. huAT01_H3_IgG1LALA including the signal sequence as a heavy-chain full-length amino acid sequence comprises the amino acid sequence set forth in SEQ ID NO: 46. The sequence is shown in FIG. 12. In the sequence, the amino acid sequence at positions 1 to 19 is the signal sequence, the amino acid sequence at positions 20 to 135 is the variable region, and the amino acid sequence at positions 136 to 465 is the constant region. Further, the amino acid sequence at positions 45 to 54 is CDRH1, the amino acid sequence at positions 69 to 78 is CDRH2, and the amino acid sequence at positions 118 to 124 is CDRH3.

The nucleotide sequence encoding the amino acid sequence of SEQ ID NO: 46 comprises the sequence set forth in SEQ ID NO: 68. Further, the nucleotide sequence encoding the heavy-chain variable region comprises the sequence set forth in SEQ ID NO: 78.

(3) the Heavy Chain Designed was Named huAT01_H3_IgG4Pro. huAT01_H3_IgG4Pro including the signal sequence as a heavy-chain full-length amino acid sequence comprises the amino acid sequence set forth in SEQ ID NO: 47. The sequence is shown in FIG. 13. In the sequence, the amino acid sequence at positions 1 to 19 is the signal sequence, the amino acid sequence at positions 20 to 135 is the variable region, and the amino acid sequence at positions 136 to 462 is the constant region. Further, the amino acid sequence at positions 45 to 54 is CDRH1, the amino acid sequence at positions 69 to 78 is CDRH2, and the amino acid sequence at positions 118 to 124 is CDRH3.

The nucleotide sequence encoding the amino acid sequence of SEQ ID NO: 47 comprises the sequence set forth in SEQ ID NO: 69. Further, the nucleotide sequence encoding the heavy-chain variable region comprises the sequence set forth in SEQ ID NO: 78.

FIG. 14 shows the comparison of the amino acid sequence (SEQ ID NO: 5) of the variable region of cAT01_H which is the heavy chain of chimeric antibody cAT01 (which will be hereinafter referred to as cAT01_H), the amino acid sequence (SEQ ID NO: 41) of the variable region of the humanized antibody heavy chain, huAT01_H1_IgG1LALA (which will be hereinafter referred to as huAT01_H1), and the amino acid sequence (SEQ ID NO: 42) of the variable region of huAT01_H3_IgG1LALA (which will be hereinafter referred to as huAT01_H3). In the sequences of huAT01_H1 and huAT01_H3, the symbol "·" represents the same amino acid residue as that of cAT01_H, and a substituted amino acid residue is shown in the site where the amino acid residue is described.

6)-1-3-2 Humanization of AT01 Antibody Light Chain

The light chain designed was named huAT01_L1. huAT01_L1 comprises the amino acid sequence set forth in SEQ ID NO: 48 including the signal sequence as a light-chain full-length amino acid sequence. The sequence is shown in FIG. 15. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

The nucleotide sequence encoding the amino acid sequence of SEQ ID NO: 48 comprises the sequence set forth in SEQ ID NO: 70. Further, the nucleotide sequence encoding the light-chain variable region comprises the sequence set forth in SEQ ID NO: 79.

The light chain designed was named huAT01_L2. huAT01_L2 comprises the amino acid sequence set forth in SEQ ID NO: 49 including the signal sequence as a light-chain full-length amino acid sequence. The sequence is shown in FIG. 16. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

The nucleotide sequence encoding the amino acid sequence of SEQ ID NO: 49 is set forth in SEQ ID NO: 71. Further, the nucleotide sequence encoding the light-chain variable region comprises the sequence set forth in SEQ ID NO: 80.

FIG. 17 shows the comparison of the amino acid sequence (SEQ ID NO: 11) of the variable region of cAT01_L, which is the light chain of chimeric antibody cAT01 (which will be hereinafter referred to as cAT01_L), the amino acid sequence (SEQ ID NO: 43) of the variable region of humanized antibody light chain huAT01_L1 (which will be hereinafter referred to as huAT01_L1), and the amino acid sequence (SEQ ID NO: 44) of the variable region of huAT01_L2 (which will be hereinafter referred to as huAT01_L2). In the sequences of huAT01_L1 and huAT01_L2, the symbol "·" represents the same amino acid residue as that of cAT01_L, and a substituted amino acid residue is shown in the site where the amino acid residue is described.

6)-1-4 Design of Humanized Amino Acid Sequence of NB7

Human germline sequences IGHV4-30-4*02 and IGHJ6*01 having high identity to the framework regions of cNB7 were selected as the acceptors of cNB7. In the molecular modeling of the variable regions, a known structure (PDB ID: 3CDF) was used as a template.

6)-1-4-1 Humanization of NB7 Antibody Heavy Chain (1) the Heavy Chain Designed was Named huNB7_H3_IgG1LALA. huNB7_H3_IgG1LALA comprises the amino acid sequence set forth in SEQ ID NO: 52 including the signal sequence as a heavy-chain full-length amino acid sequence. The sequence is shown in FIG. 18. In the sequence, the amino acid sequence at positions 1 to 19 is the signal sequence, the amino acid sequence at positions 20 to 141 is the variable region, and the amino acid sequence at positions 142 to 471 is the constant region. Further, the amino acid sequence at positions 45 to 55 is CDRH1, the amino acid sequence at positions 70 to 78 is CDRH2, the amino acid sequence at positions 118 to 130 is CDRH3.

The nucleotide sequence encoding the amino acid sequence of SEQ ID NO: 52 is set forth in SEQ ID NO: 72. Further, the nucleotide sequence encoding the heavy-chain variable region comprises the sequence set forth in SEQ ID NO: 81.

(2) the Heavy Chain Designed was Named huNB7_H3_IgG4Pro.

huNB7_H3_IgG4Pro comprises the amino acid sequence set forth in SEQ ID NO: 54 including the signal sequence as a heavy-chain full-length amino acid sequence. The sequence is shown in FIG. 19. In the sequence, the amino acid sequence at positions 1 to 19 is the signal sequence, the amino acid sequence at positions 20 to 141 is the variable region, and the amino acid sequence at positions 142 to 468 is the constant region. Further, the amino acid sequence at positions 45 to 55 is CDRH1, the amino acid sequence at positions 70 to 78 is CDRH2, the amino acid sequence at positions 118 to 130 is CDRH3.

The nucleotide sequence encoding the amino acid sequence of SEQ ID NO: 54 is set forth in SEQ ID NO: 73. Further, the nucleotide sequence encoding the heavy-chain variable region comprises the sequence set forth in SEQ ID NO: 81.

FIG. 20 shows the comparison of the amino acid sequence (SEQ ID NO: 7) of the variable region of cNB7_H, which is the heavy chain of chimeric antibody cNB7 (which will be hereinafter referred to as cNB7_H) and the amino acid sequence (SEQ ID NO: 50) of the variable region of humanized antibody heavy chain huNB7_H3_IgG1LALA (which will be hereinafter referred to as huNB7_H3). In huNB7_H3, the symbol "·" represents the same amino acid residue as that of cNB7_H, and a substituted amino acid residue is shown in the site where the amino acid residue is described.

6)-1-4-2 Humanization of NB7 Antibody Light Chain

The light chain designed was named huNB7_L3. huNB7_L3 comprises the amino acid sequence set forth in SEQ ID NO: 53 including the signal sequence as a light-chain full-length amino acid sequence. The sequence is shown in FIG. 21. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

The nucleotide sequence encoding the amino acid sequence of SEQ ID NO: 53 is set forth in SEQ ID NO: 74. Further, the nucleotide sequence encoding the light-chain variable region comprises the sequence set forth in SEQ ID NO: 82.

FIG. 22 shows the comparison of the amino acid sequence (SEQ ID NO: 13) of the variable region of cNB7_L, which is the light chain of chimeric antibody cNB7 (which will be hereinafter referred to as cNB7_L) and the amino acid sequence (SEQ ID NO: 51) of the variable region of humanized antibody light chain huNB7_L3 (which will be hereinafter referred to as huNB7_L3). In huNB7_L3, the symbol "·" represents the same amino acid residue as that of cNB7_L, and a substituted amino acid residue is shown in the site where the amino acid residue is described.

6)-2 Design of Humanized Antibody by Combining Heavy and Light Chains

6)-2-1 Design of Humanized AT01 Anti-TLR7 Antibody (1) An antibody comprising huAT01_H1_IgG1LALA consisting of the amino acid sequence at positions 20 to 465 in SEQ ID NO: 45 as the heavy chain and huAT01_L1 consisting of the amino acid sequence at positions 21 to 233 in SEQ ID NO: 48 as the light chain was named "huAT01_H1L1_IgG1LALA antibody" or "huAT01_H1L1_IgG1LALA".

(2) An antibody comprising huAT01_H3_IgG1LALA consisting of the amino acid sequence at positions 20 to 465 in SEQ ID NO: 46 as the heavy chain and huAT01_L1 consisting of the amino acid sequence at positions 21 to 233 in SEQ ID NO: 48 as the light chain was named "huAT01_H3L1_IgG1LALA antibody" or "huAT01_H3L1_IgG1LALA".

(3) An antibody comprising huAT01_H3_IgG1LALA consisting of the amino acid sequence at positions 20 to 465 in SEQ ID NO: 46 as the heavy chain and huAT01_L2 consisting of the amino acid sequence at positions 21 to 233 in SEQ ID NO: 49 as the light chain was named "huAT01_H3L2_IgG1LALA antibody" or "huAT01_H3L2_IgG1LALA".

(4) An antibody comprising huAT01_H3_IgG4Pro consisting of the amino acid sequence at positions 20 to 462 in SEQ ID NO: 47 as the heavy chain and huAT01_L2 consisting of the amino acid sequence at positions 21 to 233 in SEQ ID NO: 49 as the light chain was named "huAT01_H3L2_IgG4Pro antibody" or "huAT01_H3L2_IgG4Pro".

6)-2-2 Design of Humanized NB7 Anti-TLR7 Antibody (1) An antibody consisting of huNB7_H3_IgG1LALA consisting of the amino acid sequence at positions 20 to 471 in SEQ ID NO: 52 as the heavy chain and huNB7_L3 consisting of the amino acid sequence at positions 21 to 233 in SEQ ID NO: 53 as the light chain was named "huNB7_H3L3_IgG1LALA antibody" or "huNB7_H3L3_IgG1LALA".

(2) An antibody consisting of huNB7_H3_IgG4Pro consisting of the amino acid sequence at positions 20 to 468 in SEQ ID NO: 54 as the heavy chain and huNB7_L3 consisting of the amino acid sequence at positions 21 to 233 in SEQ ID NO: 53 as the light chain was named "huNB7_H3L3_IgG4Pro antibody" or "huNB7_H3L3_IgG4Pro".

6)-3 Production of Humanized Anti-Human TLR7 Antibody

6)-3-1 Construction of Humanized IgG1LALA Type Heavy-Chain Expression Vector, pCMA-G1LALA pCMA-G1LALA was constructed in the same manner as in Example 4)-1-2 using DNA fragments comprising the nucleotide sequences encoding the amino acid sequences of the human heavy-chain signal sequence and the human IgG1LALA constant region (SEQ ID NO: 75).

6)-3-2 Construction of Humanized IgG4Pro Type Heavy-Chain Expression Vector, pCMA-G4Pro pCMA-G4Pro was constructed in the same manner as in Example 4)-1-2 using DNA fragments comprising the nucleotide sequences encoding the amino acid sequences of the human heavy-chain signal sequence and the human IgG4Pro constant region (SEQ ID NO: 76).

6)-3-3 Construction of AT01 Humanized Heavy-Chain Expression Vector

6)-3-3-1 Construction of huAT01_H1_IgG1LALA Expression Vector

A DNA fragment represented by nucleotides 36 to 422 in the nucleotide sequence of huAT01_H1_IgG1LALA set forth in SEQ ID NO: 46 was synthesized (Geneart AG). The DNA fragment synthesized was inserted into the site where pCMA-G1LALA was cut with a restriction enzyme, BlpI, using an In-Fusion HD PCR cloning kit (Clontech Laboratories, Inc.), thereby constructing a huAT01_H1_IgG1LALA expression vector.

6)-3-3-2 Construction of huAT01_H3_IgG1LALA Expression Vector

A DNA fragment represented by nucleotides 36 to 422 in the nucleotide sequence of huAT01_H3_IgG1LALA set forth in SEQ ID NO: 68 was synthesized (Geneart AG). A huAT01_H3_IgG1LALA expression vector was constructed in the same manner as in Example 6)-3-3-1.

6)-3-3-3 Construction of huAT01_H3_IgG4Pro Expression Vector

A DNA fragment represented by nucleotides 36 to 422 in the nucleotide sequence of huAT01_H3_IgG4Pro set forth in SEQ ID NO: 69 was synthesized (Geneart AG). The DNA fragment synthesized was inserted into the site where pCMA-G4Pro was cut with a restriction enzyme, BlpI, using an In-Fusion HD PCR cloning kit (Clontech Laboratories, Inc.), thereby constructing a huAT01_H3_IgG4Pro expression vector.

6)-3-4 Construction of AT01 Humanized Light-Chain Expression Vector

6)-3-4-1 Construction of huAT01_L1 Expression Vector

A DNA fragment represented by nucleotides 37 to 399 in the nucleotide sequence of huAT01_L1 set forth in SEQ ID NO: 70 was synthesized (Geneart AG). The DNA fragment synthesized was inserted into the site where pCMA-LK was cut with a restriction enzyme, BsiWI, using an In-Fusion HD PCR cloning kit (Clontech Laboratories, Inc.), thereby constructing a huAT01_L1 expression vector.

6)-3-4-2 Construction of huAT01_L2 Expression Vector

A DNA fragment represented by nucleotides 37 to 399 in the nucleotide sequence of huAT01_L2 set forth in SEQ ID NO: 71 was synthesized (Geneart AG). A huAT01_L1 expression vector was constructed in the same manner as in Example 6)-3-4-1 using an In-Fusion HD PCR cloning kit (Clontech Laboratories, Inc).

6)-3-5 Construction of NB7 Humanized Heavy-Chain Expression Vector

6)-3-5-1 Construction of huNB7_H3_IgG1LALA Expression Vector

A DNA fragment represented by nucleotides 36 to 440 in the nucleotide sequence of huNB7_H3_IgG1LALA set forth in SEQ ID NO: 72 was synthesized (Geneart AG). A huNB7_H3_IgG1LALA expression vector was constructed in the same manner as in Example 6)-3-3-1.

6)-3-5-2 Construction of huNB7_H3_IgG4Pro Expression Vector

A DNA fragment represented by nucleotides 36 to 440 in the nucleotide sequence of huNB7_H3_IgG4Pro set forth in SEQ ID NO: 73 was synthesized (Geneart AG). A huNB7_H3_IgG4Pro expression vector was constructed in the same manner as in Example 6)-3-3-3.

6)-3-6 Construction of NB7 Humanized Light-Chain Expression Vector

6)-3-6-1 Construction of huNB7_L3 Expression Vector

A DNA fragment represented by nucleotides 37 to 399 in the nucleotide sequence of huNB7_L3 set forth in SEQ ID NO: 74 was synthesized (Geneart AG). A huNB7_L3 expression vector was constructed in the same manner as in Example 6)-3-4-1 using an In-Fusion HD PCR cloning kit (Clontech Laboratories, Inc).

6)-3-7 Preparation of Humanized Antibodies

6)-3-7-1 Production of Humanized Antibodies

Humanized antibodies of huAT01_H1L1_IgG1LALA, huAT01_H3L1_IgG1LALA, huAT01_H3L2_IgG1LALA, huAT01_H3L2_IgG4Pro, huNB7_H3L3_IgG1LALA, and huNB7_H3L3_IgG4Pro were produced by the combination of the heavy and light chains designed in Example 6)-2, using the expression vectors constructed in Examples 6)-3-1 to 6)-3-6, in the same manner as in Example 4)-2.

6)-3-7-2 Purification of Humanized Antibodies

The culture supernatant obtained in Example 6)-3-7-1 was purified by a two-step process of rProtein A affinity chromatography and ceramic hydroxyapatite.

The culture supernatant was applied to a column (GE Healthcare Bioscience) filled with MabSelectSuRe equilibrated with PBS, and thereafter the column was washed with PBS in a volume of twice or more the column volume. Next, each antibody was eluted with a 2M arginine hydrochloride solution (pH 4.0).

The fraction containing the antibody was subjected to buffer replacement with PBS by dialysis (Slide-A-Lyzer Dialysis Cassette, Thermo Scientific), diluted 5-fold with a 5 mM sodium phosphate/50-mM MES/pH 7.0 buffer, and applied to a ceramic hydroxyapatite column (Japan Bio-Rad Laboratories, Inc., Bio-Scale CHT Type-1 Hydroxyapatite Column) equilibrated with a 5-mM NaPi/50-mM MES/30 mM NaCl/pH 7.0 buffer.

Linear concentration gradient elution with sodium chloride was performed, and a fraction containing the antibody was collected. The fraction was subjected to buffer replacement with HBSor (25 mM histidine/5% sorbitol, pH 6.0) by dialysis (Slide-A-Lyzer Dialysis Cassette, Thermo Scientific). The antibody was concentrated with a Centrifugal UF Filter Device, VIVASPIN20 (fraction molecular weight UF10K, Sartorius AG), to prepare the IgG at a concentration of 50 mg/mL. Finally, filtration was carried out with a Minisart-Plus filter (Sartorius AG), to give a purified sample.

Example 7

In Vitro Activity of Humanized Anti-Human TLR7 Antibody

7)-1 Inhibitory Activity of Humanized Anti-Human TLR7 Antibody on Cytokine Production Human PBMCs were purchased from Cellular Technology Limited as a frozen product and thawed according to the instructions for use.

The PBMCs suspended at a concentration of $2.5\times10^6$ cells/mL in RPMI1640 (Life Technologies Corp.) containing 10% FBS, 1 mM Sodium Pyruvate (Life Technologies Corp.), 0.1 mM MEM Non-Essential Amino Acids (Life Technologies Corp.), 50 μM 2-Mercaptoethanol (Life Technologies Corp.), 50 U/mL Penicillin, and 50-μg/mL Streptomycin (Life Technologies Corp.) were seeded in a 96-well cell culture plate at 100 μL each, and the humanized anti-human TLR7 antibody, huAT01_H1L1_IgG1LALA, huAT01_H3L1_IgG1LALA, huAT01_H3L2_IgG1LALA, huAT01_H3L2_IgG4Pro, huNB7_H3L3_IgG1LALA, or huNB7_H3L3_IgG4Pro, or a human IgG control antibody (Eureka Therapeutics) was added thereto at 80 μL/well, followed by pretreatment in an incubator at 37° C. for 4 hours.

Thereafter, 1 mg/mL CL-264 (InvivoGen) was added thereto at 20 μL/well, and the mixture was stirred well, followed by culturing at 37° C. for about 20 hours under 5% $CO_2$.

The plate was stirred well and thereafter centrifuged at 1500 rpm for 5 minutes, and the concentration of IL-6 contained in the supernatant was measured by the FRET method (Cisbio Bioassay. Inc).

Figure 23:
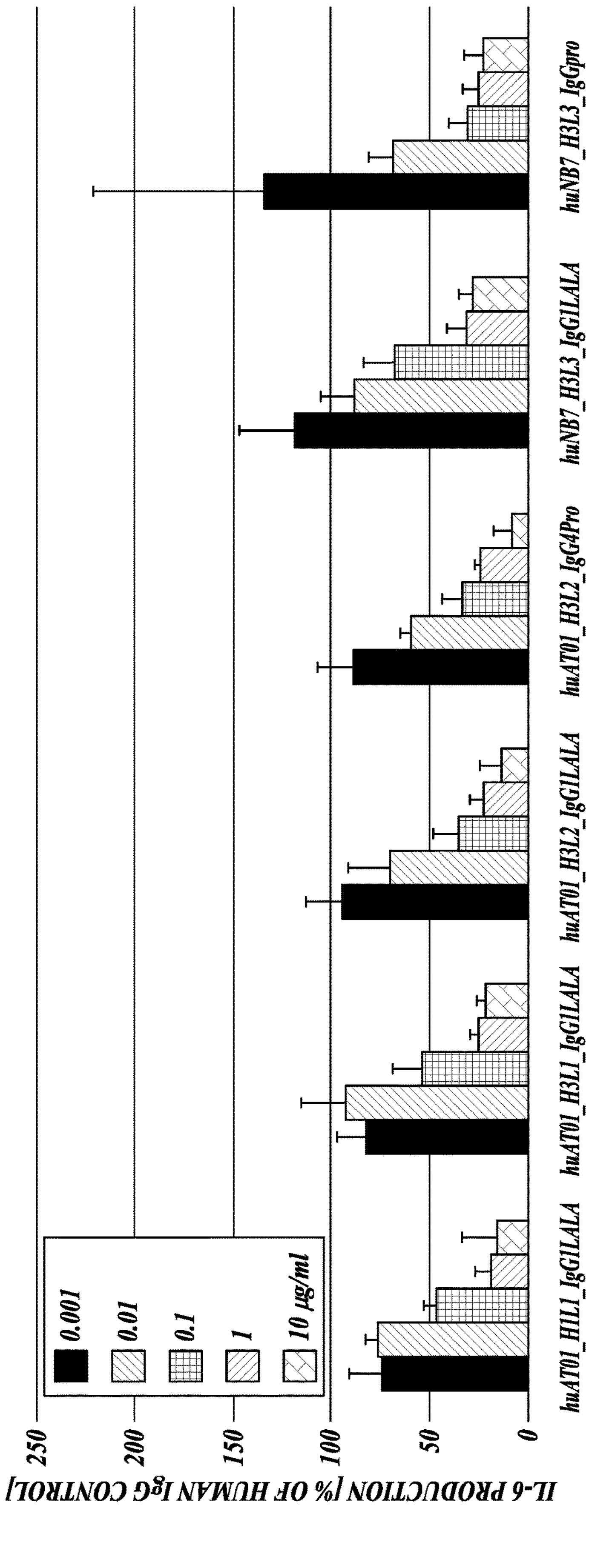
FIG. 23 is a graph showing that humanized anti-human TLR7 antibodies (huAT01_H1L1_IgG1LALA, huAT01_H3L1_IgG1LALA, huAT01_H3L2_IgG1LALA, huAT01_H3L2_IgG4Pro, huNB7_H3L3_IgG1LALA, and huNB7_H3L3_IgG4Pro) suppress the production of IL-6 from human PBMCs treated with CL-264 in a concentration dependent manner.
Figure 25:
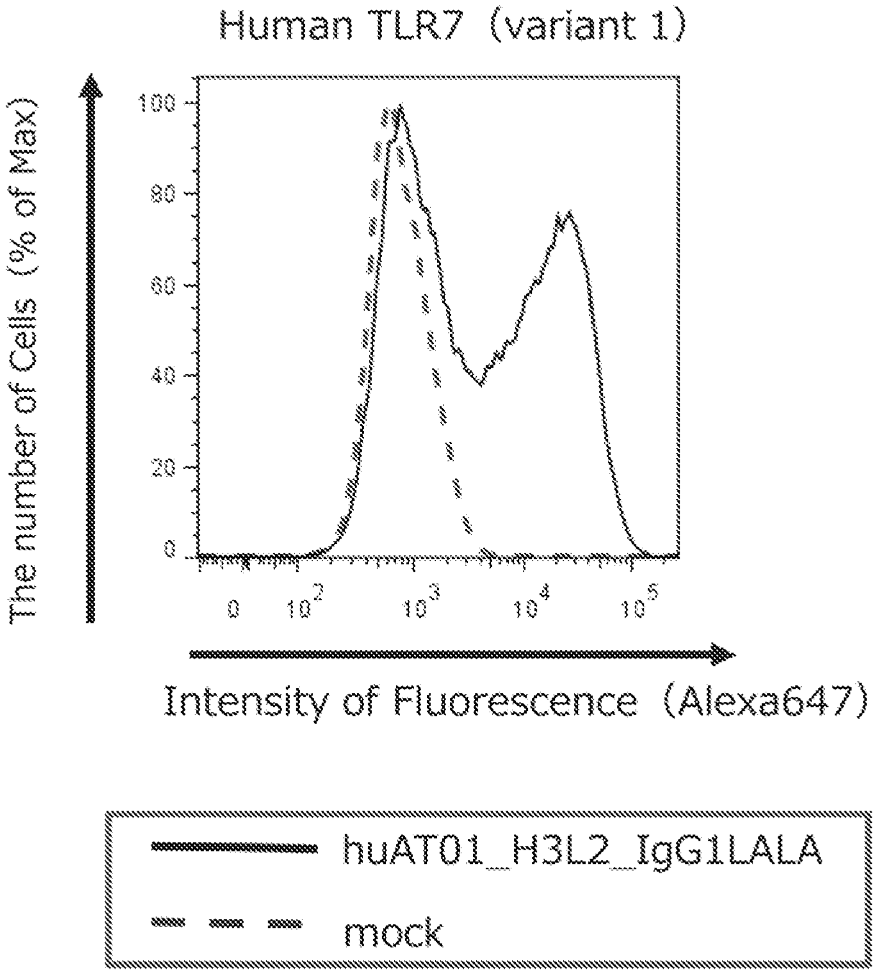
FIG. 25 shows the results of a flow cytometry analysis on binding to an antigen (human TLR7: variant 1) of humanized anti-human TLR7 antibody (huAT01_H3L2_IgG1LALA) and is a graph showing specific binding to the antigen.
Figure 26:
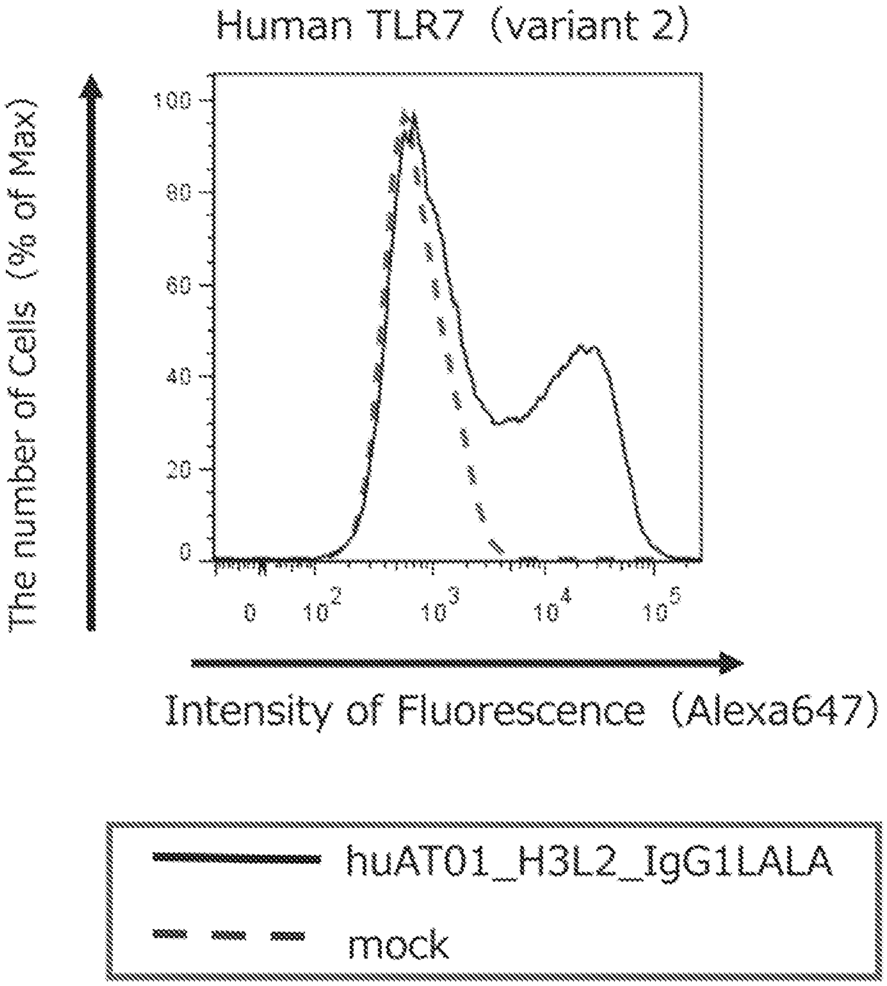
FIG. 26 shows the results of a flow cytometry analysis on binding to an antigen (human TLR7: variant 2) of humanized anti-human TLR7 antibody (huAT01_H3L2_IgG1LALA) and is a graph showing specific binding to the antigen.
Figure 27:
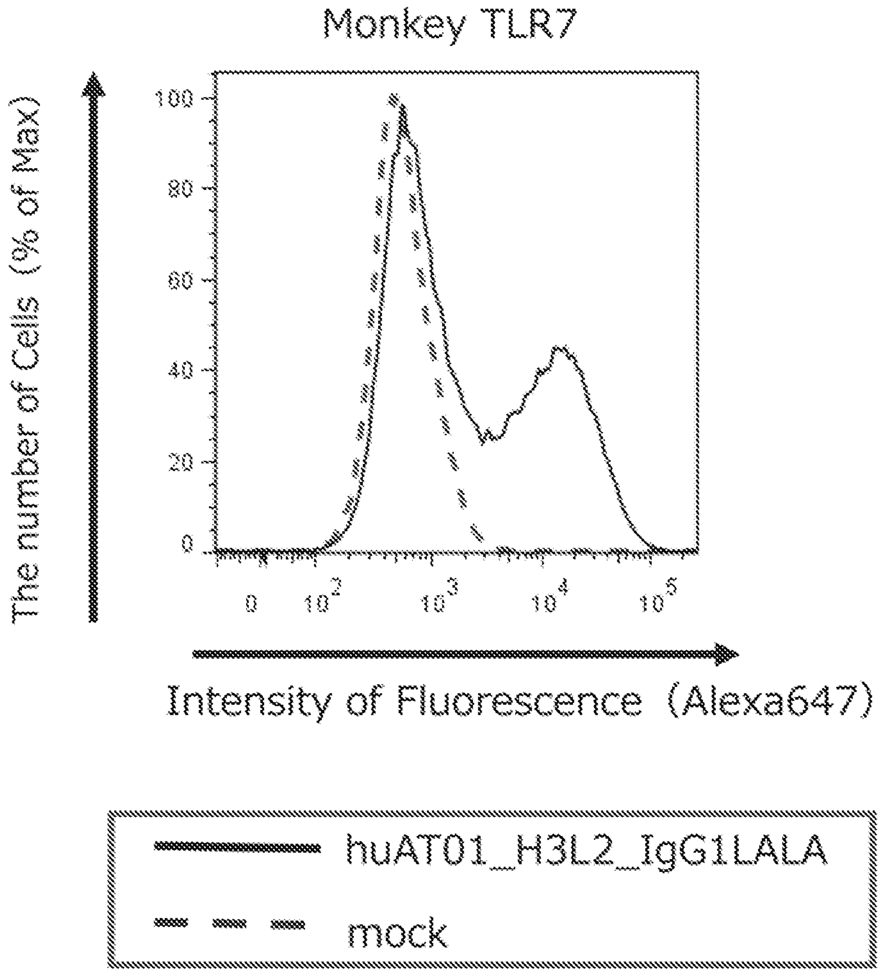
FIG. 27 shows the results of a flow cytometry analysis on binding to an antigen (monkey TLR7) of humanized anti-human TLR7 antibody (huAT01_H3L2_IgG1LALA) and is a graph showing specific binding to the antigen.
Figure 28:
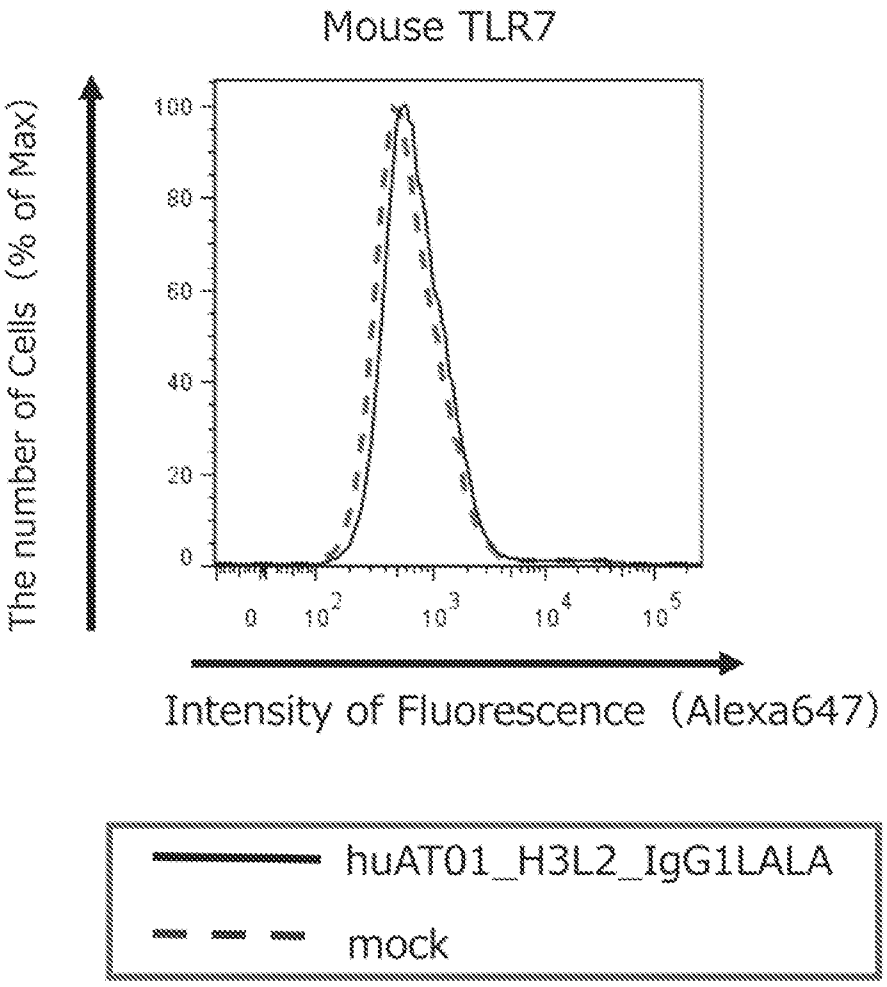
FIG. 28 shows the results of a flow cytometry analysis on binding to an antigen (mouse TLR7) of humanized anti-human TLR7 antibody (huAT01_H3L2_IgG1LALA) and is a graph showing non-binding to the antigen.
Figure 29:
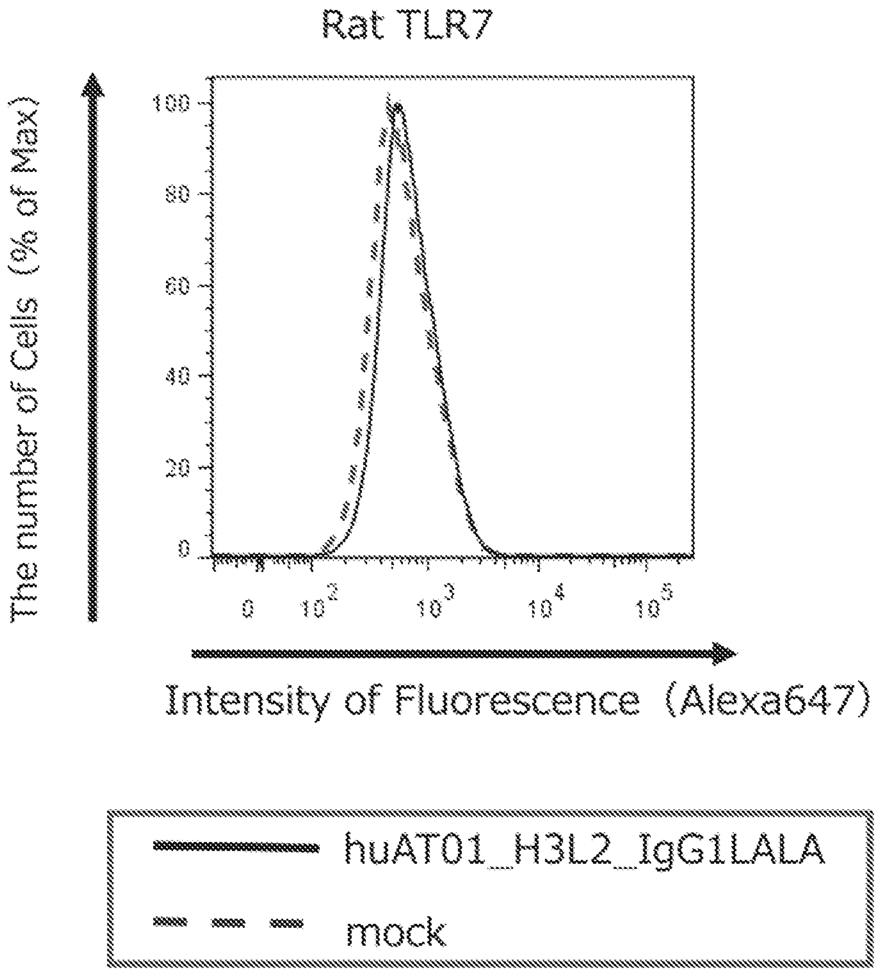
FIG. 29 shows the results of a flow cytometry analysis on binding to an antigen (rat TLR7) of humanized anti-human TLR7 antibody (huAT01_H3L2_IgG1LALA) and is a graph showing non-binding to the antigen.

FIG. 23 shows that the humanized anti-human TLR7 antibody suppresses the production of IL-6 from the human PBMCs treated with CL-264 in a concentration dependent manner.

The antibodies huAT01_H1L1_IgG1LALA, huAT01_H3L1_IgG1LALA, huAT01_H3L2_IgG1LALA, huAT01_H3L2_IgG4Pro, huNB7_H3L3_IgG1LALA, and huNB7_H3L3_IgG4Pro inhibited the production of IL-6 from the human PBMCs in a concentration dependent manner.

The half-inhibitory concentrations ($IC_{50}$) of the antibodies huAT01_H1L1_IgG1LALA, huAT01_H3L1_IgG1LALA, huAT01_H3L2_IgG1LALA, huAT01_H3L2_IgG4Pro, huNB7_H3L3_IgG1LALA and huNB7_H3L3_IgG4Pro were 74 ng/mL, 138 ng/mL, 38 ng/mL, 24 ng/mL, 307 ng/mL and 31 ng/mL, respectively, which were calculated from the concentrations of the two values, which are either side of the 50% inhibitory activity, and the inhibitory activity when each of the two concentrations were added.

Example 8

Confirmation of Antigen Binding to Humanized Anti-Human TLR7 antibody

8)-1 Preparation of HEK293 Cells Expressing Human TLR7 (Variant 1)-Flag

LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50 U/mL Penicillin, and 50 μg/mL Streptomycin (Life Technologies Corp.) under conditions of 37° C. and 5% $CO_2$.

On the next day, plasmids expressing pcDNA3.1-human TLR7 (variant 1)-Flag, produced by GenScript Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression plasmid-introduced cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that human TLR7 was expressed in the cells transfected with the plasmids expressing pcDNA3.1-human TLR7 (variant 1)-Flag, by flow cytometry (Miltenyi Biotec K.K.) using an anti-Flag-PE antibody (BioLegend, Inc.) or an isotype control antibody (BioLegend, Inc.) as a negative control.

The amino acid sequence of human TLR7 (variant 1) and a polynucleotide sequence encoding the amino acid sequence are set forth in SEQ ID NOs: 2 and 1 in the Sequence Listing, respectively.

8)-2 Preparation of HEK293 Cells Forcibly Expressing Human TLR7 (Variant 2)-Flag LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50 U/mL Penicillin, and 50-μg/mL Streptomycin (Life Technologies Corp.) under conditions of 37° C. and 5% $CO_2$.

On the next day, plasmids expressing pcDNA3.1-human TLR7 (variant 2)-Flag, produced by GenScript Biotech Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression vector-transfected cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that human TLR7 was expressed in the cells transfected with the plasmids expressing pcDNA3.1-human TLR7 (variant 2)-Flag, by flow cytometry (Miltenyi Biotec K.K.) using an anti-Flag-PE antibody (BioLegend, Inc.) or an isotype control antibody (BioLegend, Inc.) as a negative control.

8)-3 Preparation of HEK293 Cells Expressing Monkey TLR7-Flag

LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50 U/mL Penicillin, and 50-μg/mL Streptomycin (Life Technologies Corp.) under conditions of 37° C. and 5% $CO_2$.

On the next day, plasmids expressing pcDNA3.1-monkey TLR7-Flag, produced by GenScript Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression vector-transfected cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that monkey TLR7 was expressed in the cells transfected with the plasmids expressing pcDNA3.1-monkey TLR7-Flag, by flow cytometry (Miltenyi Biotec K.K.), using an anti-Flag-PE antibody (BioLegend, Inc.) or an isotype control antibody (BioLegend, Inc.) as a negative control.

8)-4 Preparation of HEK293 Cells Expressing Mouse TLR7-Flag

LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50-U/mL Penicillin, and 50-μg/mL Streptomycin (Life Technologies Corp.) under conditions of 37° C. and 5% $CO_2$.

On the next day, plasmids expressing pcDNA3.1-mouse TLR7-Flag, produced by GenScript Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression vector-transfected cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that mouse TLR7 was expressed in the cells transfected with the plasmids expressing pcDNA3.1-mouse TLR7-Flag by flow cytometry (Miltenyi Biotec K.K.), using an anti-Flag-PE antibody (BioLegend, Inc.) or an isotype control antibody (BioLegend, Inc.) as a negative control.

8)-5 Preparation of HEK293 Cells Expressing Rat TLR7-Flag

LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50 U/mL Penicillin, and 50-μg/mL Streptomycin (Life Technologies Corp.) under conditions of 37° C. and 5% $CO_2$.

On the next day, plasmids expressing pcDNA3.1-rat TLR7-Flag, produced by GenScript Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression vector-transfected cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that rat TLR7 was expressed in the cells transfected with the plasmids expressing pcDNA3.1-rat TLR7-Flag by flow cytometry (Miltenyi Biotec K.K.), using an anti-Flag-PE antibody (BioLegend, Inc.) or an isotype control antibody (BioLegend, Inc.) as a negative control.

8)-6 Evaluation of Binding Selectivity of Humanized Anti-Human TLR7 Antibody by Flow Cytometry The HEK293 cells expressing human TLR7 (variant 1)-Flag prepared in 8)-1, the HEK293 cells expressing human TLR7 (variant 2)-Flag prepared in 8)-2, the HEK293 cells expressing monkey TLR7-Flag prepared in 8)-3, the HEK293 cells expressing mouse TLR7-Flag prepared in 8)-4, and the HEK293 cells expressing rat TLR7-Flag prepared in 8)-5 were immobilized/subjected to membrane permeation with a Fixation and Permeabilization Solution (Becton, Dickinson and Company) and thereafter stained using huAT01_H3L2_IgG1LALA, which is one of the humanized anti-human TLR7 antibodies, and ALEXA FLUOR® 647 AffiniPure Goat anti-human IgG+IgM (H+L) (Jackson ImmunoResearch Inc.), which is the secondary antibody.

The binding of the humanized anti-human TLR7 antibody to human TLR7 was detected based on flow cytometry (Miltenyi Biotec K.K.), and the data was analyzed using software (Flowjo) which analyzes the data of flow cytometry.

The results indicate that huAT01_H3L2_IgG1LALA, which is one of the humanized anti-human TLR7 antibodies, bound specifically to human TLR7 (variant 1), human TLR7 (variant 2), or monkey TLR7, and did not bind to mouse TLR7 or rat TLR7. FIGS. 25 to 29 show the results.

Example 9 Evaluation of In Vivo Inhibitory Effects of Anti-Human TLR7 Antibody 9-1) Establishment of Human TLR7 Transgenic/Mouse TLR7 Knockout Mice 9-1-1) Preparation of Human TLR7 Transgenic Mouse ROSA26 locus was targeted in murine embryonic stem (ES) cells to generate human TLR7 transgenic mice.

Namely, human TLR7 plasmids were produced by incorporating human TLR7 gene (SEQ ID NO:3) into CTV (CAG-STOP-eGFP-ROSA26TV) plasmid (Addgene) by using GIBSON ASSEMBLY® systems (New England BioLabs Inc.).

Next, the human TLR7 plasmids produced above were introduced into JM8. A3 (KOMP), which is ES cells derived from C57BL/6N mice, by electroporation.

The ES cells in which human TLR7 plasmids were introduced were then selected by using neomycin.

From ES cell clones resistant to neomycin, clones in which homologous recombination occurred were selected by Southern blotting.

The selected ES cell clones were injected into mouse embryos derived from C57BL/6N mice (Japan SLC, Inc.) and the said embryos were transplanted into C57BL/6N mice (Japan SLC, Inc.) which were foster parent mice, and chimeric mice were produced.

9-1-2) Preparation of Mouse TLR7 Knockout Mice

Mouse TLR7 knockout mice were generated by using known genetic modification techniques.

That is, a guide RNA (gaacaguuggccaaucucucagg: SEQ ID NO: 87) targeting the sequence on exon 5 of the mouse TLR7 gene (SEQ ID NO:56) and a hCas9 protein (S.p. Cas9 Nuclease V3:IDT) were injected into fertilized eggs obtained from pregnant mice by mating C57BL/6N mice (Japan SLC, Inc.) to perform gene editing for deleting 4 bases on exon 5 of the mouse TLR7 gene.

Subsequently, the said fertilized eggs were transplanted into C57BL/6N mice (Japan SLC, Inc.) which were foster parent mice.

DNA was extracted from the tail of the offspring of the foster parent mice, and the said offspring of the foster parent mice was genotyped by the PCR method, and consequently the individual in which 4 bases on exon 5 of the mouse TLR7 gene were deleted, was recognized.

The said individual was confirmed to be a mouse TLR7 knockout mouse without expressing normal mouse TLR7 protein by frameshift.

9-1-3) Mating of Human TLR7 Transgenic Mice and Mouse TLR7 Knockout Mice

Human TLR7 transgenic mice produced in 9-1-1) and mouse TLR7 knockout mice produced in 9-1-2) were mated, and human TLR7 transgenic/mouse TLR7 knockout mice were established.

9-2) Evaluation of Inhibitory Effects of Anti-Human TLR7 Antibody Using Human TLR7 Transgenic/Mouse TLR7 Knockout Mice 9-2-1) Antibody Administration, R848 Administration, and Blood Sampling Human TLR7 transgenic/mouse TLR7 knockout mice established in 9-1-3) were administered 500 μg of a control antibody that does not bind human TLR7 or a humanized anti-human TLR7 antibody (huAT01_H3L2_IgG1LALA) obtained in Example 6)-3-7 intraperitoneally.

Seven days after the administration of the said antibodies, 20 μg of R848 (InvivoGen), which is a ligand of TLR7 was administered intraperitoneally for activating TLR7 function.

Blood was collected from mice of each treatment group after 6 hours from R848 administration. After blood collection, centrifugation was performed at 10,000 rpm for 15 minutes, and sera were collected.

9-2-2) Measurement of IL-6 Production Using Sera

Amount of IL-6 production was measured by ELISA kits (Thermo Fisher Scientific) using sera collected in 9-2-1).

Figure 30:
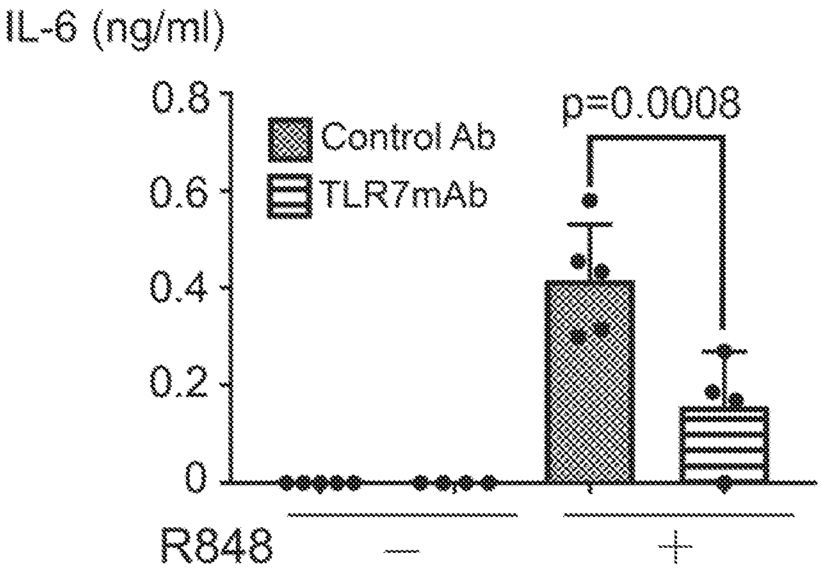
FIG. 30 shows the results of evaluation of in vivo inhibitory effects of anti-human TLR7 antibody using human TLR7 transgenic/mouse TLR7 knockout mice. Amount of IL-6 production was measured by ELISA kits using sera collected from mice treated with the control antibody or the humanized anti-human TLR7 antibody (huAT01_H3L2_IgG1LALA) and then with a ligand of TLR7 (R848).

The result is shown in FIG. 30.

Compared with the group of mice treated with the control antibody, the group of mice treated with the humanized anti-human TLR7 antibody significantly reduced the amount of IL-6 production (p=0.0008).

INDUSTRIAL APPLICABILITY

The humanized anti-TLR7 antibody of the present invention has a human TLR7 function-inhibitory activity-suppressing action and thus can be an agent for treating or preventing immune inflammation-related diseases and the like.

SEQUENCE LISTING

SEQ ID NO: 1: Nucleotide sequence encoding human TLR7 (variant 1)
SEQ ID NO: 2: Amino acid sequence of human TLR7 (variant 1)
SEQ ID NO: 3: Nucleotide sequence encoding human TLR7 (variant 2)
SEQ ID NO: 4: Amino acid sequence of human TLR7 (variant 2)
SEQ ID NO: 5: Amino acid sequence of heavy-chain variable region of AT01 antibody
SEQ ID NO: 6: Nucleotide sequence encoding heavy-chain variable region of cAT01 antibody
SEQ ID NO: 7: Amino acid sequence of heavy-chain variable region of NB7 antibody
SEQ ID NO: 8: Nucleotide sequence encoding heavy-chain variable region of cNB7 antibody
SEQ ID NO: 9: Amino acid sequence of heavy-chain variable region of FAN2 antibody
SEQ ID NO: 10: Nucleotide sequence encoding heavy-chain variable region of cFAN2 antibody
SEQ ID NO: 11: Amino acid sequence of light-chain variable region of AT01 antibody
SEQ ID NO: 12: Nucleotide sequence encoding light-chain variable region of cAT01 antibody
SEQ ID NO: 13: Amino acid sequence of light-chain variable region of NB7 antibody
SEQ ID NO: 14: Nucleotide sequence encoding light-chain variable region of cNB7 antibody
SEQ ID NO: 15: Amino acid sequence of light-chain variable region of FAN2 antibody
SEQ ID NO: 16: Nucleotide sequence encoding light-chain variable region of cFAN2 antibody
SEQ ID NO: 17: Amino acid sequence of CDRH1 of AT01 antibody
SEQ ID NO: 18: Amino acid sequence of CDRH2 of AT01 antibody
SEQ ID NO: 19: Amino acid sequence of CDRH3 of AT01 antibody
SEQ ID NO: 20: Amino acid sequence of CDRL1 of AT01 antibody
SEQ ID NO: 21: Amino acid sequence of CDRL2 of AT01 antibody
SEQ ID NO: 22: Amino acid sequence of CDRL3 of AT01 antibody
SEQ ID NO: 23: Amino acid sequence of CDRH1 of NB7 antibody
SEQ ID NO: 24: Amino acid sequence of CDRH2 of NB7 antibody
SEQ ID NO: 25: Amino acid sequence of CDRH3 of NB7 antibody
SEQ ID NO: 26: Amino acid sequence of CDRL1 of NB7 antibody
SEQ ID NO: 27: Amino acid sequence of CDRL2 of NB7 antibody
SEQ ID NO: 28: Amino acid sequence of CDRL3 of NB7 antibody
SEQ ID NO: 29: Amino acid sequence of CDRH1 of FAN2 antibody
SEQ ID NO: 30: Amino acid sequence of CDRH2 of FAN2 antibody
SEQ ID NO: 31: Amino acid sequence of CDRH3 of FAN2 antibody
SEQ ID NO: 32: Amino acid sequence of CDRL1 of FAN2 antibody
SEQ ID NO: 33: Amino acid sequence of CDRL2 of FAN2 antibody
SEQ ID NO: 34: Amino acid sequence of CDRL3 of FAN2 antibody
SEQ ID NO: 35: Amino acid sequence of heavy chain of AT01 chimeric anti-human TLR7 antibody (cAT01)
SEQ ID NO: 36: Amino acid sequence of light chain of AT01 chimeric anti-human TLR7 antibody (cAT01)
SEQ ID NO: 37: Amino acid sequence of heavy chain of NB7 chimeric anti-human TLR7 antibody (cNB7)
SEQ ID NO: 38: Amino acid sequence of light chain of NB7 chimeric anti-human TLR7 antibody (cNB7)
SEQ ID NO: 39: Amino acid sequence of heavy chain of FAN2 chimeric anti-human TLR7 antibody (cFAN2)
SEQ ID NO: 40: Amino acid sequence of light chain of FAN2 chimeric anti-human TLR7 antibody (cFAN2)
SEQ ID NO: 41: Amino acid sequence of heavy-chain variable region of huAT01_H1_IgG1LALA
SEQ ID NO: 42: Amino acid sequence of heavy-chain variable region of huAT01_H3_IgG1LALA
SEQ ID NO: 43: Amino acid sequence of light-chain variable region of huAT01_L1
SEQ ID NO: 44: Amino acid sequence of light-chain variable region of huAT01_L2
SEQ ID NO: 45: Amino acid sequence of huAT01_H1_IgG1LALA
SEQ ID NO: 46: Amino acid sequence of huAT01_H3_IgG1LALA
SEQ ID NO: 47: Amino acid sequence of huAT01_H3_IgG4Pro
SEQ ID NO: 48: Amino acid sequence of huAT01_L1
SEQ ID NO: 49: Amino acid sequence of huAT01_L2

SEQ ID NO: 50: Amino acid sequence of heavy-chain variable region of huNB7_H3_IgG1LALA SEQ ID NO: 51: Amino acid sequence of light-chain variable region of huNB7_L3

SEQ ID NO: 52: Amino acid sequence of huNB7_H3_IgG1LALA

SEQ ID NO: 53: Amino acid sequence of huNB7_L3

SEQ ID NO: 54: Amino acid sequence of huNB7_H3_IgG4Pro

SEQ ID NO: 55: Nucleotide sequence of human Unc93B1 gene

SEQ ID NO: 56: Nucleotide sequence of mouse TLR7 gene

SEQ ID NO: 57: Nucleotide sequence of rat TLR7 gene

SEQ ID NO: 58: Nucleotide sequence of monkey TLR7 gene

SEQ ID NO: 59: Nucleotide sequences of DNA fragments comprising nucleotide sequences encoding human light-chain signal sequence and human kappa-chain constant region SEQ ID NO: 60: Nucleotide sequences of DNA fragments comprising nucleotide sequences encoding human heavy-chain signal sequence and human IgG1 constant region SEQ ID NO: 61: Nucleotide sequence encoding heavy chain of cAT01 antibody SEQ ID NO: 62: Nucleotide sequence of DNA fragment comprising nucleotide sequence encoding light chain of cAT01 antibody SEQ ID NO: 63: Nucleotide sequence encoding heavy chain of cNB7 antibody SEQ ID NO: 64: Nucleotide sequence of DNA fragment comprising nucleotide sequence encoding light chain of cNB7 antibody SEQ ID NO: 65: Nucleotide sequence encoding heavy chain of cFAN2 antibody SEQ ID NO: 66: Nucleotide sequence of DNA fragment comprising nucleotide sequence encoding cFAN2 antibody light chain SEQ ID NO: 67: Nucleotide sequence encoding huAT01_H1_IgG1LALA SEQ ID NO: 68: Nucleotide sequence encoding huAT01_H3_IgG1LALA SEQ ID NO: 69: Nucleotide sequence encoding huAT01_H3_IgG4Pro SEQ ID NO: 70: Nucleotide sequence encoding huAT01_L1

SEQ ID NO: 71: Nucleotide sequence encoding huAT01_L2

SEQ ID NO: 72: Nucleotide sequence encoding huNB7_H3_IgG1LALA

SEQ ID NO: 73: Nucleotide sequence encoding huNB7_H3_IgG4Pro

SEQ ID NO: 74: Nucleotide sequence encoding huNB7_L3

SEQ ID NO: 75: Nucleotide sequences of DNA fragments comprising nucleotide sequences encoding human heavy-chain signal sequence and human IgG1LALA constant region SEQ ID NO: 76: Nucleotide sequences of DNA fragments comprising nucleotide sequences encoding human heavy-chain signal sequence and human IgG4Pro constant region SEQ ID NO: 77: Nucleotide sequence encoding heavy-chain variable region of huAT01_H1

SEQ ID NO: 78: Nucleotide sequence encoding heavy-chain variable region of huAT01_H3

SEQ ID NO: 79: Nucleotide sequence encoding light-chain variable region of huAT01_L1

SEQ ID NO: 80: Nucleotide sequence encoding light-chain variable region of huAT01_L2

SEQ ID NO: 81: Nucleotide sequence encoding heavy-chain variable region of huNB7_H3

SEQ ID NO: 82: Nucleotide sequence encoding light-chain variable region of huNB7_L3

SEQ ID NO: 83: Amino acid sequence of mouse TLR7

SEQ ID NO: 84: Amino acid sequence of rat TLR7

SEQ ID NO: 85: Amino acid sequence of monkey TLR7

SEQ ID NO: 86: Nucleotide sequence of human Unc93B1 D34A mutant-HA×2 gene

SEQ ID NO: 87: guide RNA targeting the sequence on exon 5 of the mouse TLR7 gene

The invention claimed is:

1. A method for treating a disease caused by a function of human TLR7 by inhibiting the function of human TLR7, comprising administering to an individual at least one of an antibody or an antigen-binding fragment of the antibody having CDRH1 consisting of the amino acid sequence set forth in SEQ ID NO: 17, CDRH2 consisting of the amino acid sequence set forth in SEQ ID NO: 18, and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21, and CDRL3 consisting of the amino acid sequence set forth in SEQ ID NO: 22, as complementarity determining regions in the light chain.

2. A method for treating a disease caused by a function of human TLR7 by inhibiting the function of human TLR7, comprising simultaneously, separately or sequentially administering to an individual (a) an immunosuppressant, an anti-inflammatory drug, an anti-allergic agent, an anti-infective agent or an anticancer agent and (b) at least one of an antibody or an antigen-binding fragment having CDRH1 consisting of the amino acid sequence set forth in SEQ ID NO: 17, CDRH2 consisting of the amino acid sequence set forth in SEQ ID NO: 18, and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21, and CDRL3 consisting of the amino acid sequence set forth in SEQ ID NO: 22, as complementarity determining regions in the light chain.

3. The treatment method according to claim 1, wherein the disease caused by a function of human TLR7 is an immune inflammation-related disease, an allergic disease, an infection or a cancer.

4. The treatment method according to claim 3, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

5. The treatment method according to claim 3, wherein the immune inflammation-related disease is systemic lupus erythematosus.

6. The treatment method according to claim 2, wherein the disease caused by a function of human TLR7 is an immune inflammation-related disease, an allergic disease, an infection or a cancer.

7. The treatment method according to claim 6, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

8. The treatment method according to claim 6, wherein the immune inflammation-related disease is systemic lupus erythematosus.

9. The treatment method according to claim 1, wherein the antibody or the antigen-binding fragment of the antibody comprises:

(a) a heavy-chain variable region consisting of the amino acid sequence set forth in SEQ ID NO: 41 and a light-chain variable region consisting of the amino acid sequence set forth in SEQ ID NO: 43;

(b) a heavy-chain variable region consisting of the amino acid sequence set forth in SEQ ID NO: 41 and a light-chain variable region consisting of the amino acid sequence set forth in SEQ ID NO: 44;

(c) a heavy-chain variable region consisting of the amino acid sequence set forth in SEQ ID NO: 42 and a light-chain variable region consisting of the amino acid sequence set forth in SEQ ID NO: 43; or (d) a heavy-chain variable region consisting of the amino acid sequence set forth in SEQ ID NO: 42 and a light-chain variable region consisting of the amino acid sequence set forth in SEQ ID NO: 44.

10. The treatment method according to claim 9, wherein the antibody or the antigen-binding fragment of the antibody comprises a heavy-chain variable region consisting of the amino acid sequence set forth in SEQ ID NO: 42 and a light-chain variable region consisting of the amino acid sequence set forth in SEQ ID NO: 44.

11. The treatment method according to claim 9, wherein the antibody or the antigen-binding fragment of the antibody comprises:

(a) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48;

(b) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 49;

(c) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48;

(d) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49;

(e) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 48; or (f) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49.

12. The treatment method according to claim 11, wherein the antibody or the antigen-binding fragment of the antibody comprises a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

13. The treatment method according to claim 12, wherein one amino acid is deleted at the carboxyl terminus in each of the two heavy chains.

14. The treatment method according to claim 2, wherein the antibody or the antigen-binding fragment of the antibody comprises:

(a) a heavy-chain variable region consisting of the amino acid sequence set forth in SEQ ID NO: 41 and a light-chain variable region consisting of the amino acid sequence set forth in SEQ ID NO: 43;

(b) a heavy-chain variable region consisting of the amino acid sequence set forth in SEQ ID NO: 41 and a light-chain variable region consisting of the amino acid sequence set forth in SEQ ID NO: 44;

(c) a heavy-chain variable region consisting of the amino acid sequence set forth in SEQ ID NO: 42 and a light-chain variable region consisting of the amino acid sequence set forth in SEQ ID NO: 43; or (d) a heavy-chain variable region consisting of the amino acid sequence set forth in SEQ ID NO: 42 and a light-chain variable region consisting of the amino acid sequence set forth in SEQ ID NO: 44.

15. The treatment method according to claim 14, wherein the antibody or the antigen-binding fragment of the antibody comprises a heavy-chain variable region consisting of the amino acid sequence set forth in SEQ ID NO: 42 and a light-chain variable region consisting of the amino acid sequence set forth in SEQ ID NO: 44.

16. The treatment method according to claim 14, wherein the antibody or the antigen-binding fragment of the antibody comprises:

(a) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48;

(b) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 49;

(c) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48;

(d) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49;

(e) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 48; or (f) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49.

17. The treatment method according to claim 16, wherein the antibody or the antigen-binding fragment of the antibody comprises a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

18. The treatment method according to claim 17, wherein one amino acid is deleted at the carboxyl terminus in each of the two heavy chains.

* * * * *